United States Patent
Richardson et al.

(10) Patent No.: US 8,409,627 B2
(45) Date of Patent: Apr. 2, 2013

(54) PARTICULATE WOOD PRESERVATIVE AND METHOD FOR PRODUCING THE SAME

(75) Inventors: H. Wayne Richardson, Sumter, SC (US); Robert L. Hodge, Sumter, SC (US)

(73) Assignee: Osmose, Inc., Buffalo, NY (US)

( * ) Notice: Subject to any disclaimer, the term of this patent is extended or adjusted under 35 U.S.C. 154(b) by 416 days.

(21) Appl. No.: 12/458,522

(22) Filed: Jul. 15, 2009

(65) Prior Publication Data

US 2009/0280185 A1  Nov. 12, 2009

Related U.S. Application Data

(63) Continuation of application No. 10/868,967, filed on Jun. 17, 2004, now abandoned.

(60) Provisional application No. 60/478,820, filed on Jun. 17, 2003, provisional application No. 60/478,825, filed on Jun. 17, 2003, provisional application No. 60/478,827, filed on Jun. 17, 2003, provisional application No. 60/478,822, filed on Jun. 17, 2003, provisional application No. 60/571,535, filed on May 17, 2004.

(51) Int. Cl.
*A01N 59/00* (2006.01)
*A01N 59/20* (2006.01)

(52) U.S. Cl. .......... 424/630; 424/633; 424/634

(58) Field of Classification Search .......... 424/630, 424/633, 634
See application file for complete search history.

(56) References Cited

U.S. PATENT DOCUMENTS

| | | | |
|---|---|---|---|
| 1,388,513 A * | 8/1921 | Chandler | 427/291 |
| 1,999,458 A | 4/1935 | Hollister | |
| 2,558,304 A | 6/1951 | Marcot et al. | |
| 3,007,844 A | 11/1961 | Schulz | |
| 3,087,936 A | 4/1963 | Le Suer et al. | |
| 3,231,464 A | 1/1966 | Dettwiler et al. | |
| 3,254,025 A | 5/1966 | Le Suer et al. | |
| 3,443,881 A | 5/1969 | Hudson | |
| 3,535,423 A | 10/1970 | Ordas | |
| 3,622,377 A | 11/1971 | Conner | |
| 3,816,307 A | 6/1974 | Woods | |
| 3,837,875 A | 9/1974 | Murphy | |
| 3,874,891 A | 4/1975 | Grobmann et al. | |
| 3,945,835 A | 3/1976 | Clarke et al. | |
| 3,957,494 A | 5/1976 | Oberley | |
| 3,968,276 A | 7/1976 | Allen | |
| 4,003,994 A | 1/1977 | Downer et al. | |
| 4,058,607 A | 11/1977 | Hennart et al. | |
| 4,062,991 A | 12/1977 | Kyte et al. | |
| 4,075,326 A | 2/1978 | Kuyama et al. | |
| 4,089,999 A | 5/1978 | Mondt et al. | |
| 4,142,009 A | 2/1979 | Kyte | |
| 4,172,904 A | 10/1979 | Young et al. | |
| 4,220,688 A | 9/1980 | Mitchell et al. | |
| 4,310,590 A | 1/1982 | Petigara | |
| 4,313,976 A | 2/1982 | Leach | |
| 4,339,617 A | 7/1982 | Imai et al. | |
| 4,404,169 A | 9/1983 | Ploss et al. | |
| RE31,576 E | 5/1984 | Hilditch | |
| 4,456,486 A | 6/1984 | Bernhard | |
| 4,507,152 A | 3/1985 | Collins et al. | |
| 4,539,047 A | 9/1985 | Crockatt et al. | |
| 4,596,694 A | 6/1986 | Rozmus | |
| 4,597,730 A | 7/1986 | Rozmus | |
| 4,622,248 A * | 11/1986 | Leach et al. | 427/440 |
| RE32,329 E | 1/1987 | Paszner | |
| 4,649,065 A | 3/1987 | Hein et al. | |
| 4,650,792 A | 3/1987 | Underwood | |
| 4,663,364 A | 5/1987 | Iwasaki et al. | |
| 4,670,430 A | 6/1987 | Imamura | |
| 4,698,099 A | 10/1987 | Nakamura et al. | |
| 4,702,776 A | 10/1987 | Hoffner et al. | |
| 4,720,514 A | 1/1988 | Needham | |
| 4,737,491 A | 4/1988 | Leppavuori et al. | |
| 4,741,971 A | 5/1988 | Beck | |
| 4,750,934 A * | 6/1988 | Metzner et al. | 106/18 |
| 4,752,297 A | 6/1988 | Leach | |
| 4,808,406 A | 2/1989 | Brinkman | |

(Continued)

FOREIGN PATENT DOCUMENTS

| | | |
|---|---|---|
| AU | 646732 | 10/1992 |
| AU | B-15117/92 | 10/1992 |

(Continued)

OTHER PUBLICATIONS

Liu et al. ,Journal of Applied Polymer Science,2002, vol. 86, 596-607.*

(Continued)

*Primary Examiner* — Fereydoun G Sajjadi
*Assistant Examiner* — Courtney Brown
(74) *Attorney, Agent, or Firm* — Covington & Burling LLP; Einar Stole; Jessica L. Parezo

(57) ABSTRACT

A wood preservative includes injectable particles comprising one or more sparingly soluble copper salts. The copper-based particles are sufficiently insoluble so as to not be easily removed by leaching but are sufficiently soluble to exhibit toxicity to primary organisms primarily responsible for the decay of the wood. Exemplary particles contain for example copper hydroxide, basic copper carbonate, copper carbonate, basic copper sulfates including particularly tribasic copper sulfate, basic copper nitrates, copper oxychlorides, copper borates, basic copper borates, and mixtures thereof. The particles typically have a size distribution in which at least 50% of particles have a diameter smaller than 0.25 μm, 0.2 μm, or 0.15 μm. At least about 20% and even more than 75% of the weight of the particles may be composed of the substantially crystalline copper salt. Wood or a wood product may be impregnated with copper based particles of the invention.

35 Claims, 3 Drawing Sheets

U.S. PATENT DOCUMENTS

| | | | |
|---|---|---|---|
| 4,857,214 A | 8/1989 | Papay et al. |
| 4,857,365 A | 8/1989 | Hirao et al. |
| 4,872,916 A | 10/1989 | Latosky |
| 4,897,427 A | 1/1990 | Barnavon et al. |
| 4,923,894 A | 5/1990 | Kanda et al. |
| 4,950,221 A | 8/1990 | Gordon |
| 4,961,865 A | 10/1990 | Pennartz |
| 4,986,851 A | 1/1991 | Dietz et al. |
| 4,988,545 A | 1/1991 | Laks |
| 5,030,285 A | 7/1991 | Vallvey et al. |
| 5,049,677 A | 9/1991 | Prout |
| 5,098,472 A | 3/1992 | Watkins et al. |
| 5,110,822 A | 5/1992 | Sherba et al. |
| 5,130,463 A | 7/1992 | Haubennestel et al. |
| 5,145,684 A | 9/1992 | Liversidge et al. |
| 5,147,686 A | 9/1992 | Ichimura |
| 5,151,218 A | 9/1992 | Haubennestel et al. |
| 5,186,947 A | 2/1993 | Goettsche et al. |
| 5,196,407 A | 3/1993 | Goletz et al. |
| 5,198,133 A | 3/1993 | Papay |
| 5,200,421 A | 4/1993 | Ludwig et al. |
| 5,207,823 A | 5/1993 | Shiozawa |
| 5,277,979 A | 1/1994 | Kielbania, Jr. et al. |
| 5,304,376 A | 4/1994 | Friedrichs et al. |
| 5,342,438 A | 8/1994 | West |
| 5,360,783 A | 11/1994 | Itoh et al. |
| 5,424,077 A | 6/1995 | Lajoie |
| 5,426,121 A | 6/1995 | Bell |
| 5,438,034 A | 8/1995 | Walker |
| 5,462,589 A | 10/1995 | Nicholas et al. |
| 5,462,931 A | 10/1995 | Shaber et al. |
| 5,470,585 A | 11/1995 | Gilchrist |
| 5,478,598 A | 12/1995 | Shiozawa |
| 5,484,934 A | 1/1996 | Ikeda |
| 5,527,384 A | 6/1996 | Williams et al. |
| 5,527,423 A | 6/1996 | Neville et al. |
| 5,527,816 A | 6/1996 | Shaber et al. |
| 5,536,305 A | 7/1996 | Yu |
| 5,552,378 A | 9/1996 | Trinh et al. |
| 5,582,638 A | 12/1996 | Coutelle et al. |
| 5,624,916 A | 4/1997 | Shaber et al. |
| 5,635,217 A | 6/1997 | Goettsche et al. |
| 5,667,795 A | 9/1997 | Fraley et al. |
| 5,693,644 A * | 12/1997 | Teramae et al. ............... 514/269 |
| 5,714,507 A | 2/1998 | Valcke et al. |
| 5,763,364 A | 6/1998 | Frisch et al. |
| 5,833,741 A | 11/1998 | Walker |
| 5,855,662 A | 1/1999 | Brand et al. |
| 5,874,025 A | 2/1999 | Heuer et al. |
| 5,874,456 A | 2/1999 | McDade |
| 5,874,476 A | 2/1999 | Hsu et al. |
| 5,916,356 A | 6/1999 | Williams et al. |
| 5,961,843 A | 10/1999 | Hayakawa et al. |
| 5,972,266 A | 10/1999 | Fookes |
| 5,990,043 A | 11/1999 | Kugler |
| 6,033,648 A | 3/2000 | Candau |
| 6,074,986 A | 6/2000 | Mulqueen et al. |
| 6,110,263 A | 8/2000 | Goettsche et al. |
| 6,123,756 A | 9/2000 | Poppen |
| 6,139,879 A | 10/2000 | Taylor |
| 6,143,318 A | 11/2000 | Gilchrist et al. |
| 6,250,350 B1 | 6/2001 | Muraki et al. |
| 6,274,199 B1 | 8/2001 | Preston et al. |
| 6,303,183 B1 | 10/2001 | Wilczynski et al. |
| 6,306,201 B1 | 10/2001 | Makino |
| 6,306,202 B1 | 10/2001 | West |
| 6,306,939 B1 | 10/2001 | Gupta et al. |
| 6,342,556 B1 | 1/2002 | Batdorf et al. |
| 6,352,583 B1 | 3/2002 | Goettsche et al. |
| 6,471,969 B1 | 10/2002 | Schlachter et al. |
| 6,475,631 B1 | 11/2002 | Yamamoto et al. |
| 6,482,814 B1 * | 11/2002 | Bath et al. ..................... 514/184 |
| 6,485,790 B2 | 11/2002 | Walker et al. |
| 6,503,306 B1 | 1/2003 | Watkins |
| 6,514,512 B1 | 2/2003 | Puterka |
| 6,521,288 B2 | 2/2003 | Laks et al. |
| 6,537,670 B1 | 3/2003 | Sassi |
| 6,541,038 B1 | 4/2003 | Tanaka et al. |
| 6,558,685 B1 | 5/2003 | Kober |
| 6,572,788 B2 | 6/2003 | Walker et al. |
| 6,576,661 B1 | 6/2003 | Bruck et al. |
| 6,579,354 B1 | 6/2003 | West |
| 6,585,989 B2 | 7/2003 | Herbst |
| 6,593,260 B2 | 7/2003 | Nomura |
| 6,596,246 B2 | 7/2003 | Huato et al. |
| 6,646,147 B2 | 11/2003 | Richardson et al. |
| 6,686,056 B2 | 2/2004 | Roos et al. |
| 6,689,731 B2 | 2/2004 | Esselborn et al. |
| 6,699,818 B1 | 3/2004 | Walter et al. |
| 6,700,006 B2 | 3/2004 | Thames et al. |
| 6,753,035 B2 | 6/2004 | Laks et al. |
| 6,770,674 B1 | 8/2004 | Young |
| 6,830,822 B2 | 12/2004 | Yadav |
| 6,843,837 B2 | 1/2005 | Zhang et al. |
| 6,849,276 B1 | 2/2005 | Dufau et al. |
| 6,867,250 B1 | 3/2005 | Gupta et al. |
| 6,887,400 B1 | 5/2005 | Wei et al. |
| 6,905,531 B2 | 6/2005 | Richardson et al. |
| 6,905,532 B2 | 6/2005 | Richardson et al. |
| 7,105,136 B2 | 9/2006 | Ploss et al. |
| 7,238,654 B2 | 7/2007 | Hodge et al. |
| 7,316,738 B2 | 1/2008 | Richardson et al. |
| 7,426,948 B2 | 9/2008 | Richardson et al. |
| 7,449,130 B2 | 11/2008 | Lloyd |
| 7,674,481 B2 | 3/2010 | Leach et al. |
| 8,158,208 B2 | 4/2012 | Richardson et al. |
| 2001/0021711 A1 | 9/2001 | Beilfuss et al. |
| 2001/0051175 A1 | 12/2001 | Strom et al. |
| 2002/0003179 A1 | 1/2002 | Verhoff et al. |
| 2002/0047058 A1 | 4/2002 | Verhoff et al. |
| 2002/0051892 A1 * | 5/2002 | Laks et al. .................... 428/541 |
| 2002/0055046 A1 | 5/2002 | Ono et al. |
| 2002/0110692 A1 | 8/2002 | Suzuki et al. |
| 2002/0128367 A1 | 9/2002 | Daisey, Jr. et al. |
| 2003/0010956 A1 | 1/2003 | Las et al. |
| 2003/0013799 A1 | 1/2003 | Crooks et al. |
| 2003/0017565 A1 * | 1/2003 | Echigo et al. ................. 435/189 |
| 2003/0040569 A1 | 2/2003 | Curry et al. |
| 2003/0060504 A1 | 3/2003 | Yoshida et al. |
| 2003/0077219 A1 | 4/2003 | Ploss et al. |
| 2003/0086979 A1 | 5/2003 | Ghosh |
| 2003/0108759 A1 | 6/2003 | Roos et al. |
| 2003/0127023 A1 | 7/2003 | Grandidier et al. |
| 2003/0170317 A1 | 9/2003 | Curzon et al. |
| 2004/0024099 A1 | 2/2004 | Narayanan et al. |
| 2004/0050298 A1 | 3/2004 | Giger et al. |
| 2004/0051084 A1 | 3/2004 | Wessling et al. |
| 2004/0063847 A1 | 4/2004 | Curry et al. |
| 2004/0176477 A1 | 9/2004 | Davison et al. |
| 2004/0258767 A1 * | 12/2004 | Leach et al. .................. 424/630 |
| 2004/0258768 A1 | 12/2004 | Richardson et al. |
| 2004/0258838 A1 | 12/2004 | Richardson et al. |
| 2005/0013939 A1 | 1/2005 | Venden |
| 2005/0107467 A1 | 5/2005 | Richardson |
| 2005/0118280 A1 | 6/2005 | Leach et al. |
| 2005/0130866 A1 | 6/2005 | Richardson et al. |
| 2005/0152994 A1 | 7/2005 | Leach et al. |
| 2005/0182152 A1 | 8/2005 | Nonninger et al. |
| 2005/0249812 A1 | 11/2005 | Leach et al. |
| 2005/0252408 A1 | 11/2005 | Richardson et al. |
| 2005/0255251 A1 | 11/2005 | Hodge et al. |
| 2005/0256026 A1 | 11/2005 | Hodge et al. |
| 2005/0265893 A1 | 12/2005 | Leach et al. |
| 2006/0062926 A1 | 3/2006 | Richardson |
| 2006/0075921 A1 | 4/2006 | Richardson et al. |
| 2006/0075923 A1 | 4/2006 | Richardson |
| 2006/0078686 A1 | 4/2006 | Hodge et al. |
| 2006/0086284 A1 | 4/2006 | Zhang et al. |
| 2006/0086841 A1 | 4/2006 | Richardson et al. |
| 2006/0112850 A1 | 6/2006 | Zhang et al. |
| 2006/0147632 A1 | 7/2006 | Zhang et al. |
| 2006/0257578 A1 | 11/2006 | Zhang et al. |
| 2006/0288904 A1 | 12/2006 | Leach et al. |
| 2007/0021385 A1 | 1/2007 | Zhang et al. |
| 2007/0131136 A1 | 6/2007 | Zhang et al. |
| 2007/0193473 A1 | 8/2007 | Zhang et al. |
| 2007/0259016 A1 | 11/2007 | Hodge et al. |

| | | | |
|---|---|---|---|
| 2008/0199525 | A1 | 8/2008 | Leach et al. |
| 2008/0199535 | A1 | 8/2008 | Taylor et al. |
| 2008/0210121 | A1 | 9/2008 | Zhang et al. |
| 2008/0213608 | A1 | 9/2008 | Richardson et al. |
| 2008/0260841 | A1 | 10/2008 | Leach et al. |
| 2008/0286380 | A1 | 11/2008 | Zhang et al. |
| 2009/0028917 | A1 | 1/2009 | Leach et al. |
| 2009/0035564 | A1 | 2/2009 | Leach et al. |
| 2009/0092683 | A1 | 4/2009 | Leach et al. |
| 2009/0143478 | A1 | 6/2009 | Richardson et al. |

FOREIGN PATENT DOCUMENTS

| | | | |
|---|---|---|---|
| CA | 2103470 | | 8/1994 |
| CA | 2251534 | | 10/1997 |
| DE | 2531895 | A1 | 2/1977 |
| DE | 3542441 | A1 | 6/1987 |
| DE | 3930687 | A1 | 4/1991 |
| DE | 4112652 | A1 | 10/1992 |
| EP | 0173964 | A2 | 3/1986 |
| EP | 0256427 | A2 | 2/1988 |
| EP | 0472973 | A1 | 3/1992 |
| EP | 0499299 | A2 | 8/1992 |
| EP | 0577952 | A1 | 1/1994 |
| EP | 1034903 | | 9/2000 |
| EP | 1649749 | A1 | 4/2006 |
| GB | 222268 | | 10/1924 |
| GB | 812408 | | 4/1959 |
| GB | 822869 | | 11/1959 |
| GB | 822869 | A | 11/1959 |
| GB | 1491330 | | 11/1977 |
| GB | 1491330 | A | 11/1977 |
| GB | 1531868 | A | 11/1978 |
| GB | 1531868 | A1 | 11/1979 |
| JP | 60-155403 | | 8/1985 |
| JP | S61-244502 | | 10/1986 |
| JP | 61-246002 | | 11/1986 |
| JP | 62039201 | | 2/1987 |
| JP | 62116102 | | 5/1987 |
| JP | 10-26401 | | 1/1989 |
| JP | 8-183010 | | 7/1996 |
| JP | 10-272610 | | 10/1998 |
| JP | 2000-102907 | | 4/2000 |
| JP | 2000-141316 | | 5/2000 |
| JP | 2000141316 | * | 5/2000 |
| JP | 2000141316 | A | 5/2000 |
| JP | 2001-121512 | | 8/2001 |
| JP | 2003/266406 | A | 9/2003 |
| NZ | 225428 | | 3/1991 |
| NZ | 280716 | | 2/1999 |
| NZ | 304884 | | 3/1999 |
| PL | 169344 | | 5/1994 |
| SE | 379167 | | 9/1975 |
| SU | 642166 | | 1/1979 |
| SU | 0642166 | A1 | 1/1979 |
| WO | 85/00040 | | 1/1985 |
| WO | WO-87/04696 | A1 | 8/1987 |
| WO | WO-92/19429 | A1 | 11/1992 |
| WO | WO 92/14929 | | 12/1992 |
| WO | 95/27600 | | 10/1995 |
| WO | WO-98/05206 | A1 | 2/1998 |
| WO | 9955505 | | 11/1999 |
| WO | 00/05955 | | 2/2000 |
| WO | 00/24259 | | 5/2000 |
| WO | 00/24528 | | 5/2000 |
| WO | WO-00/60940 | A1 | 10/2000 |
| WO | 00/78281 | | 12/2000 |
| WO | WO 01/91925 | A1 | 12/2001 |
| WO | 02/06417 | | 1/2002 |
| WO | WO-02/00196 | A2 | 1/2002 |
| WO | WO-03/025303 | A1 | 3/2003 |
| WO | 03/103392 | | 12/2003 |
| WO | 2004091875 | | 10/2004 |
| WO | WO-2004/091875 | A2 | 10/2004 |
| WO | WO-2005/104841 | A1 | 11/2005 |
| WO | WO-2005/110692 | A2 | 11/2005 |
| WO | WO-2005/115704 | A2 | 12/2005 |
| WO | 2006044218 | | 4/2006 |
| WO | WO-2006/042128 | A2 | 4/2006 |
| WO | WO-2006/042129 | A1 | 4/2006 |

OTHER PUBLICATIONS 5.1 Inorganic Fungicides—5.1.1 Metal Salts, Pesticide Chemistry, pp. 272-486, 1988.

American Wood Preservers' Association (AWPA) Standard E10-1, "Standard Method of Testing Wood Preservatives by Laboratory Soil-Block Cultures," 2005.

American Wood Preservers' Association (AWPA) Standard E7-01, "Standard Method of Evaluating Wood Preservatives by Field Tests with Stakes," 2006.

Backman, P.A. et al., The Effects of Particle Size and Distribution on Performance of the Fungicide Chlorothalonil, Phytopathology, St. Paul, MN, US, vol. 66, No. 10, 1 Jan. 1, 1976, pp. 1242-1245, XP009062911.

Barnes, H. M., et al., The Impact of Test Site and Oil Content on the Performance of Pentachlorophenol-treated Wood, Forest Products Journal, vol. 56, No. 5, pp. 43-47, May 2006.

Borkow, Gadi, et al., Copper as a Biocidal Tool, Proceedings, Ninety-Fifth Annual Meeting of the American Wood-Preservers' Association, vol. 95, May 16-19, 1999.

Crusberg, T.C., et al., Biomineralization of Heavy Metals, pp. 409-417, 2004.

Davis, Food Storage and Preservative-Treated Wood, Alaska Science Forum (Mar. 10, 1980) [online] [retrieve on Nov. 10, 2008]. URL: http://www.gi.alaska.edu/Science Forum/ASF3/380.htm/.

Hawley's Condensed Chemical Dictionary, 14th edition; John Wiley & Sons, Inc., 2001, p. 86.

Humar, M., et al., Changes of the pH of Impregnated Wood During Exposure to Wood-Rotting Fungi, Holz als Roh-und Werkstoff 59 (2001) 288-293.

Humar, M., et al., Effect of Oxalic, Acetic Acid, and Ammonia on Leaching of Cr and Cu from Preserved Wood, Wood Sci Technol 37 (2004) 463-473.

Humar, M., et al., Influence of Moisture Content on EPR Parameters of Copper in Impregnated Wood, Holz als Roh-und Werkstoff 59 (2001) 254-255.

International Society of Soil Science. (http://www.clays.org.au/mins.htm).

Kartal, S. N., et al., Do the Unique Properties of Nanometals Affect Leachability or Efficacy Against Fungi and Termines? International Biodeterioration & Biodegradation 63 (2009) 490-495.

Kubel, H., et al., The Chemistry and Kinetic Behaviour of Cu—Cr—As/B Wood Preservatives—Part 5. Reactions of CCB and Cellulose, Lignin and their Simple Model Compounds, Holzforschung und Holzverwertung 34 (1982) 4, pp. 75-83.

Lebow, Stan, et al., Fixation Effects on the Release of Copper, Chromium and Arsenic From CCA-C Treated Marine Piles, Report Prepared for American Wood-Preservers' Association Subcommittee P-3, Piles, Aug. 1999, pp. 168-174.

Lide; "Characteristics of Particles and Particle Dispersoids"; Handbook of Chemistry and Physics; 75th Edition; 1994; Florida: CRC Press, pp. 15-38.

Morrell, J. J. Wood Pole Maintenance Manual (1996 Edition), Research Contribution 15, Oct. 1996, p. 22.

Pizzi, A., et al., The Chemistry and Kinetic Behaviour of Cu—Cr—As/B Wood Preservatives—Part 6. Fixation of CCB in Wood and Physical and Chemical Comparison of CCB and CCA, Holzforschung and Holzverwertung 34 (1982) 5, pp. 80-86.

Ratajczak, Izabela, et al., Fixation of Copper(II)-Protein Formulation in Wood: Part 1. Influence of Tannic Acid on Fixation of Copper in Wood, Holzforschung, vol. 62, pp. 294-299, 2008.

Rathore, H. S., et al., Fungicide and Herbicide Residues in Water, Handbook of Water Analysis, pp. 608-654, Handbook of Water Analysis, 2000.

Resch, Helmuth, Location of Pentachlorophenol by Electron Microscopy and Other Techniques in Cellon Treated Douglas-Fir, Forest Products J. 21/1, pp. 38-43, Jan. 1971.

S.E.A. McCallan, "The Nature of the Fungicidal Action of Copper and Sulfur," The Botanical Review, Symposium on Chemicals for Agriculture, American Chemical Society, Washington, D.C., Aug. 30, 1948.

Schultz, T.P., et al., A Brief Overview of Non-Arsenical Wood Preservative, American Chemical Society, Chapter 26, pp. 420-429, 2003.

Shaw; www.fda.gov/ohrms/dockets/ac/01/slides/3763s2_09_shaw.ppt; 2001.

STN online, file SCISEARCH, Acc. No. 1993:540390 (Siegfried, Comparative Toxicity of Pyrethroid Insecticides to Terrestial and Aquatic Insects, Environmental Toxicology and Chemistry (1993), vol. 12, No. 9, pp. 1683-1689, Abstract.

Superior Court of New Jersey, Decision After Trial, *Phibro-Tech, Inc. v. Osmose Holding, Inc.*, Docket No. C-365-05, Jun. 25, 2007.

Supplementary European Search Report for PCT/US2005/016503 dated Feb. 2, 2009.

Supplementary European Search Report for PCT/US2005/037303 dated Feb. 5, 2009.

The Merck Index (12th Ed. 1996) Merck & Co., Inc., pp. 1555-1556.

Thompson, R., CBE, The Chemistry of Wood Preservation, Feb. 28-Mar. 1, 1991.

Wapnir, Raul A., Copper Absorption and Bioavailability, Am J Clin Nutr 1998; 67 (suppl.): 1054S-60S.

Request for Inter Partes Reexamination of U.S. Patent No. 7,674,481 filed by Arch Wood Protection, Inc. with the United States Patent and Trademark Office on Aug. 13, 2010 and a draft of the Request.

Bailey, Irving W., "The Preservative Treatment of Wood, II. The Structure of the Pit Membranes in the Tracheids of Conifers and their Relation to the Penetration of Gases, Liquids, and Finely Divided Solids into Green and Seasoned Wood," Forest Quarterly, 11:12-20, p. 15 (1913).

Merriam-Webster's Collegiate Dictionary, 10th ed., 1993.

"Defendants' Answer to Plaintiff's Amended Complaint and Defendants' Counterclaims," May 30, 2010, *Osmose, Inc. v. Arch Chemicals, et al.*, USDC, Eastern District of VA, Norfolk Division Case No. C.A. No. 2:10 cv 108-JBF/FBS.

"Osmose's Answer to Defendants' Counterclaims," Jun. 21, 2010, *Osmose, Inc. v. Arch Chemicals, et al.*, USDC, Eastern District of VA, Norfolk Division Case No. C.A. No. 2:10 cv 108-JBF/FBS.

American Wood-Preservers' Association (AWPA) Standard A3-00, 2003.

Statutory Declaration of Dr. Robin Nicholas Wakeling, in the matter of Australian Patent Acceptance No. 2004230950 and Opposition thereto, dated Sep. 20, 2010.

Notice of Opposition to a European Patent (Application No. EP04776802.3/Patent No. EP1651401), filed by Dr. David Elsy on Apr. 21, 2010.

Amended Notice of Opposition and Statement of Case filed Aug. 23, 2010 filed by Mattersmiths Holdings Limited; Notice of Opposition to Grant of Patent (Section 21) (Application No. 542889) filed by Mattersmiths Holdings Limited on Jun. 22, 2010.

Statement of Grounds and Particulars filed by Arch Wood Protection Pty Ltd. with the Commissioner of Patents on Dec. 18, 2009, In the Matter of Australian Patent Application No. 2004230950 in the name of Osmose, Inc.

Proceedings of the Fourth International Congress of Pesticide Chemistry (IUPAC), Article VII-23, 1978.

"Defendants' Supplemental Response to Interrogatory No. 12 and its Subparts," Aug. 26, 2010, *Osmose, Inc. v. Arch Chemicals, et al.*, USDC Eastern District of VA, Norfolk Division Case No. C.A. No. 2:10 cv 108-JBF.

"Fungicides, Biocides and Preservatives for Industrial and Agricultural Applications," by Ernest W. Flick, 1987, Noyes Publications, p. 184.

Opinion and Order dated Jan. 28, 2011, *Osmose, Inc. v. Arch Chemicals, Inc., et al.*, USDC Eastern District of VA, Norfolk Division, Case No. C.A. No. 2:10 cv 108.

Expert Report of Dr. Frank Beall, Ph.D. Concerning the Invalidity of U.S. Patent No. 7,674,481, USDC Eastern District of Virginia, Norfolk Division, Civil Action No. 2:10cv108, Jan. 21, 2011.

Supplemental Expert Report of Dr. Frank Beall, Ph.D. Concerning the Invalidity of U.S. Patent No. 7,674,481, Feb. 11, 2011, USDC Eastern District of Virginia, Norfolk Division, Civil Action No. 2:10cv108.

Rebuttal Expert Report of John Ruddick, USDC Eastern District of Virginia, Norfolk Division, Civil Action No. 2:10cv108, Feb. 22, 2011 (redacted).

American Wood Preservers' Association (AWPA) Standard E10-06, "Standard Method of Testing Wood Preservatives by Laboratory Soil-Block Cultures," 2007.

American Wood Preservers' Association (AWPA) Standard E10-09, "Standard Method of Testing Wood Preservatives by Laboratory Soil-Block Cultures," 2010.

American Wood Preservers' Association (AWPA) Standard E11-06, "Standard Method of Determining the Leachability of Wood Preservatives," 2007.

American Wood Preservers' Association (AWPA) Standard E22-09, "Standard Accelerated Laboratory Method for Testing the Efficacy of Preservatives Against Wood Decay Fungi Using Compression Strength," 2010.

ASTM D5664, "Standard Test Method for Evaluating the Effects of Fire-Retardant Treatments and Elevated Temperatures on Strength Properties of Fire Retardant Treated Lumber," 2002.

"Preservation of Timber with Zinc Chloride by the Steeping Process," Technical Notes, Forest Products Laboratory, U.S. Forest Service.

Freeman, Mike H., et al., "A Comprehensive Review of Copper-Based Wood Preservatives," Forest Products Journal, vol. 58, No. 11, pp. 6-27, Nov. 2008.

Stirling, Rod, et al., "Micro-Distribution of Micronized Copper in Southern Pine," The International Research Group on Wood Protection, 39th Annual Meeting, May 25-28, 2008.

The Federal Circuit Bar Association Model Patent Jury Instructions, last edited Feb. 18, 2010.

Liese, W., "Fine Structure of Bordered Pits in Softwoods," Cellular Ultrastructure of Woody Plants, pp. 271-290, 1965.

Graph, "Fine Structure of Bordered Pits in Softwoods".

Response to Office Action by Patent Owner in Inter Partes Reexamination under 37 CFR § 1.945, USPTO Reexamination Control No. 95/001,418, filed by Osmose, Inc., Dec. 21, 2010.

Third Party Comments After Patent Owner Response, USPTO Reexamination Control No. 95/001,418, filed by Arch Wood Protection, Inc., Jan. 20, 2011.

Koch, "Synthesis of Nanostructured Materials by Mechanical Milling: Problems and Opportunities," Nanostructured Materials vol. 9, pp. 13-22, 1997.

Rudd et al., "The Influence of Ultaviolet Illumination on Passive Behavior of Zinc," J. of Electrochemical Society, 147 (4), pp. 1401-1407, 2000.

Liu et al., "Use of Nanoparticles for Controlled Release of Biocides in Solid Wood," J. Appl. Polym. Sci., 79:458-465 (2001).

Liu et al., "Use of Nanoparticles for the Controlled Release of Biocides in Pressure Treated Solid Wood," Presentation at American Checical Society, Las Vegas, NV Oct. 1997.

Laks et al., "Polymer Nanoparticles as a Carrier System for Wood Preservatives," PowerPoint Presentation to Rohm & Hass under confidentiality agreement, Oct. 30, 1998.

AJ Panshin and Carl De Zeeuw, Textbook of Wood Technology, $4^{th}$ ed. pp. 112-113 (1980).

F. Cui and K. J. Archer "Treatment of lumbar with preservative/water repellant emulsions—The significance of shear stability on penetration," The International Research Group on Wood Preservation, IRG/WP 97-20124, paper prepared for the $28^{th}$ Annual Meeting, Whistler, British Columbia, Canada, May 25-30, 1997.

*Phibro-Tech, Inc. v. Osmose Holdings, Inc. et al.*, Civil Action C365-05, Superios Court of New Jersey, Chancery Division, Bergen County.

AR Zahora and CM Rector, "Water repellent additives for pressure treatments," Proceeding of the Eleventh Annual Meeting of the Canadian Wood Preservation Association, Toronto, Ontario, 11:22-41 (Nov. 6 and 7, 1990).

Liu et al., "Use of Nanoparticles for Controlled Release of Biocides in Pressure-Treated Solid Wood," Polymer Preprints 38(2):624 and 625, 1997.

Liu et al., "Use of Polymeric Nanoparticles for Controlled Release of Biocides in Solid Wood," Abstract, GG3.4, Symposium GG Polymeric Materials—Drugs, Delivery and Devices Nov. 30-Dec. 1, 1998, Proceedings published as vol. 550 of the Materials Research Society Symposium Proceedings Series.

Liu, "Use of Polymer Nanoparticles as Carriers for the Controlled Release of Biocides in Solid Wood," Dissertation fro the Degree of Ph.D., Michigan Technological University, 1999.

Nano Technology in brief, Feb. 20, 2004, available at http://nanotechweb.org/articles/news/3/2/12/1.

Nasibulin et al., "Copper and Copper Oxide Nanoparticle Formation by Chemical Vapor Nucleation From Copper (II) Acetylacetonate," Journal of Nanoparticle Research, 3(5-6):383-398, 2001.

Fojutowski, A.; Lewandowski O., Zesz. Probl. Postepow Nauk Roln. No. 209: 197-204, 1978.

"A New Approach to Non-Toxic, Wide-Spectrum, Ground-Contact Wood Preservatives, Part I. Approach and reaction Mechanisms," Holzforschung vol. 47, No. 3, 1993, pp. 253-260.

Feist and Mraz, Forest Products Lab Madison, Wisconsin, "Wood Finishing: Water Repellents and Water-Repellent Preservatives," Revision, Report No. FSRN-FPL-0124-Rev (NTIS 1978).

"The Copper Champs! Unique Copper Hydroxide Formulations," (Brochure), Nufarm Americas Inc. (2002).

"Thermal Conductivity of Heterogenous Two-Component Systems," Ind. & Engr. Chem. Fund., 1, 187-191 (1962), R. L. Hamilton and O.K. Cosse.

Dev et al. "Termite Resistance and Permanency Tests on Zinc-Borate—An Environmental Friendly Preservative," Timb. Dev. Assoc. (India) vol. XLIII, No. 2, Apr. 1997.

Laks et al. "Anti-Sapstain efficacy of borates against *Aureobasidium pullulans*," Forest Products Journal 43(1):33-34 (1993).

Shchiol "Some Properties of Zinc and Cadmium Borates" Russian Journal of Inorganic Chemistry, 913-915 (1959).

Tsunoda "Effects of zinc borate on the properties of medium density fiberboard. (Composites and Manufactured Products)." Forest Products Journal (Nov. 1, 2002).

Wang JZ, DeGroot R "Treatability and durability of heartwood" In: Ritter, M.A.; Duwadi, S.R.; Lee, P.Dh., ed(s). National conference on wood transportation structures; Oct. 23-25, 1996; Madison, WI. Gen. Tech. Rep. FPL-GTR-94, Madison, WI: U.S. Department of Agriculture, Forest Service, Forest Products Laboratory pp. 252-260.

Superior Court of New Jersey, Chancery Division, Final Judgment, *Phibro-Tech, Inc.* v. *Osmose Holdings, Inc., Osmose, Inc.*, docket No. C-365-05, Aug. 14, 2007.

Liu, Y., et al., Michigan Technical Univ., Dept. of Chemistry, Houghton, MI, Use of Polymeric Nanoparticles for Controlled Release of Biocides in Solid Wood, Materials Research Society Symposium Proceedings Series; 1998, vol. 550, Abstract GG3.4.

Lewis Sr., R. J., "Antineoplastic," Hawley's Condensed Chemical Disctionary, 14th Edition, John Wiley & Son, Inc., 2001, p. 86.

A. Pizzi, "A New Approach to Non-Toxic, Wild-Spectrum, Ground-Contact Wood Preservatives. Pat II. Accelerated and Long-term Field Tests," Holzforschung 47 (1993) 343-348.

Supplementary European Search Report dated Apr. 21, 2009 for PCT/US2005/035946.

Hungarian Search Report dated Jul. 15, 2010 for Singaporean Patent Application No. 200717645-6.

Australian Patent Office Examination Report dated Jun. 1, 2010 for Singaporean Patent Application No. 200717652-2.

Notice of Opposition to Grant of Patent (Section 21) (Application No. 542889) filed by Mattersmiths Holdings Limited on Jun. 22, 2010.

Liu, Y., et al., "Use of Nanoparticles for the Controlled Release of Biocides in Pressure-treated Solid Wood"; Presentation at the American Chemical Society, Las Vegas, Oct. 1997.

First Office Action issued Oct. 21, 2010 in Inter Partes Reexamination Control No. 95/001,418.

Action Closing Prosecution issued Apr. 29, 2011 in Inter Partes Reexamination Control No. 95/001,418.

Patent Owner's Response Under 37 CFR 1.951(a) to the Action Closing Prosecution in Inter Partes Reexamination Control 95/001,418. May 27, 2011.

Declaration of Dr. John N.R. Ruddick Under 37 CFR 1.132, in Inter Partes Reexamination Control No. 95/001,418. May 26, 2011.

* cited by examiner

Milled                          Unmilled

Figure 1A                 Figure 1B

Sliced interior section of a wood block untreated, treated at 0.22 pounds per cubic foot with injected copper salt particulates, and treated and developed.

PARTICULATE WOOD PRESERVATIVE AND METHOD FOR PRODUCING THE SAME

CROSS-REFERENCE TO RELATED APPLICATIONS

This application is a continuation of U.S. application Ser. No. 10/868,967, filed Jun. 17, 2004 which claims priority to the following U.S. Provisional applications 60/478,822, 60/478,827, 60/478,825, and 60/478,820, all of which were filed on Jun. 17, 2003, and also to U.S. Provisional application 60/571,535 filed on May 17, 2004, each of which is incorporated herein by reference.

FIELD OF THE INVENTION

The present invention relates to wood preservatives, particularly wood preservatives comprising particles including one or more copper compounds. More particularly, the invention relates to a wood preservative comprising injectable particles of sparingly soluble copper salts, as well as methods to prepare the wood preservative, and methods of preserving wood using the wood preservatives.

BACKGROUND OF THE INVENTION

The production of wood which has been treated to inhibit biological decomposition is well known. Decay is caused by fungi that feed on cellulose or lignin of wood. Such organisms causing wood decomposition include: basidiomycetes such as *Gloeophyllum trabeum* (brown rot), *Trametes versicolor* (white rot), *Serpula lacrymans* (dry rot) and *Coniophora puteana*. Soft rot attacks the surface of almost all hard and softwoods, and it favors wet conditions. Most of these fungi require food and moisture, e.g., moisture contents in wood of greater than 20% are conducive to fungal growth. Dry rot is tenacious, as it can grow in dry wood. Insects are also major causes of wood deterioration. Exemplary organisms causing wood decomposition include coleopterans such as *Anobium punctatum* (furniture beetle), *Hylotrupes bajulus* (house longhorn) and *Xestobium rufovillorum* (death watch beetle); hymenopterans such as termites and carpenter ants; and also by marine borers and/or wasps. Finally, termites are ubiquitous, and termite damage is estimated in the United States alone to be about $2 billion per year The production of wood based composite products has increased dramatically in recent years. Oriented strandboard (OSB) production exceeded that of plywood in 2000. The use of medium density fiberboard and hardboard panel products likewise has increased dramatically over the last couple of decades. However, these products are typically used in interior applications where attack from insects or decay fungi is limited, because it has been found that these products are particularly susceptible to attack by biological agents such as decay fungi and termites.

Preservatives are used to treat wood to resist insect attack and decay. The commercially used preservatives are separated into three basic categories, based primarily on the mode of application-waterborne, creosote, and oil borne preservatives. Waterborne preservatives include chromated copper arsenate (CCA), ammoniacal copper quat (ACQ, which is believed to be Copper-MEA-Carbonate and a quaternary amine), ammoniacal copper zinc arsenate (ACZA), and ammoniacal copper arsenate (ACA). Wood treated with these chemicals sometimes turns green or grey-green because of a chemical reaction between copper in the preservative and the sun's ultraviolet rays. The preservatives leach into the soil over time, especially those made without chromium, when exposed to weather. Creosote does not easily leach into soil, and it is not corrosive to metals, but it can not be painted and it leaves a dark, oily surface that has a strong odor. Oil borne preservatives are made of certain compounds dissolved in light petroleum oils, including pentachlorophenol (commonly known as "penta"), copper naphthenate, and copper-8-quinolinolate. These preservatives leave a surface that often is non-paintable, and the surface of the wood can be dark and unnaturally colored.

Modern organic biocides are considered to be relatively environmentally benign and not expected to pose the problems associated with CCA-treated lumber. Biocides such as tebuconazole are quite soluble in common organic solvents, while others such as chlorothalonil possess only low solubility. The solubility of organic biocides affects the markets for which the biocide-treated wood products are appropriate. Biocides with good solubility can be dissolved at high concentrations in a small amount of organic solvents, and that solution can be dispersed in water with appropriate emulsifiers to produce an aqueous emulsion. The emulsion can be used in conventional pressure treatments for lumber and wood treated in such a manner, and can be used in products such as decking where the treated wood will come into contact with humans. Biocides which possess low solubility must be incorporated into wood in a solution of a hydrocarbon oil, such as AWPA P9 Type A, and the resulting organic solution is used to treat wood directly. Wood treated in this way can be used only for industrial applications, such as utility poles and railway ties, because the oil is irritating to human skin.

The primary preserved wood product has historically been southern pine lumber treated with chromated copper arsenate (CCA). Most of this treated lumber was used for decks, fencing and landscape timbers. There has recently been raised concerns about the safety and health effects of CCA as a wood preservative, primarily relating to the arsenic content but also to the chromium content. In 2003/2004, due in part to regulatory guidelines and to concerns about safety, there has been a substantial cessation of use of CCA-treated products. A new generation of copper containing wood preservatives uses a form of copper that is soluble. Known preservatives include copper alkanolamine complexes, copper polyaspartic acid complex, alkaline copper quaternary, copper azole, copper boron azole, copper bis(dimethyldithiocarbamate), ammoniacal copper citrate, copper citrate, and the copper ethanolamine carbonate. In practice, the principal criterion for commercial acceptance, assuming treatment efficacy, is cost. Of the many compositions listed above, only two soluble copper containing wood preservatives have found commercial acceptance: 1) the copper ethanolamine carbonate manufactured for example according to the process disclosed in U.S. Pat. Nos. 6,646,147 and 2) copper boron azole. There are, however, several problems with these new copper-containing preservatives.

The soluble copper containing wood preservatives are very leachable, compared to CCA. One study has shown that as much as 80 percent of the copper from a copper amine carbonate complex is removed in about 10 years under a given set of field conditions. Under severe conditions, such as the those used for the American Wood Preserving Association's standard leaching test, these products are quickly leached from the wood. For example, we found that 77% by weight of a Cu-monoethanolamine preservative was leached from the preserved wood in 14 days. This leaching is of concern for at least two reasons: 1) removal of the copper portion of the pesticide from the wood by leaching will compromise the long term efficacy of the formulation and 2) the leached copper causes concern that the environment will be contaminated. While most animals tolerate copper, copper is extremely toxic to certain fish at sub-part per million levels. Common ranges for $EC_{50}$ for copper are between 2 and 12 micrograms per liter. Another study reported following the Synthetic Precipitation Leaching Procedure. The study results showed that the leachate from CCA-treated wood contained about 4 mg copper per liter; leachate from copper boron azole-treated wood contained about 28 mg copper per liter; leachate from copper bis(dimethyldithiocarbamate) treated wood had 7 to 8 mg copper per liter; leachate from alkaline copper quaternary treated wood had 29 mg copper per liter; and leachate from copper citrate treated wood had 62 mg copper per liter. However, copper concentrations depend in part on copper concentration, and CCA had about 7% of total copper leach, the alkaline copper quaternary preservative had about 12% of the total copper leach, while the copper boron azole had about 22% of the total copper leach during the Synthetic Precipitation Leaching Procedure. Copper leaching is such a problem that some states do not allow use of wood treated with the soluble copper containing wood preservatives near waterways.

Another concern with soluble copper preservative products generally is that most preservative materials are manufactured at one of several central locations but are used in disparate areas and must be shipped, sometimes substantial distances. The cost of providing and transporting the liquid carrier for these soluble products can be considerable, and the likelihood of an extreme biological impact is very high if transported soluble copper wood preservative material is spilled or accidentally released near a waterway.

Further, unlike CCA, all of these soluble copper containing wood preservatives require a second organic biocide to be effective against some biological species. Therefore, wood preserved with these soluble copper containing wood preservatives also contains a second biocide that is efficacious against one or more particularly troublesome species. Oil-soluble biocides such as a copper(II)-sulfited tannin extract complex (epicatechins) can be dissolved in light oils, emulsified in water, and injected into the wood, as is disclosed in U.S. Pat. No. 4,988,545. Alternatively, the second biocide is often slightly water soluble or emulsified, and may be composed of a triazole group or a quaternary amine group or a nitroso-amine group, and this biocide can be simply added to the fluid used for pressure treating the wood.

One attempt to improve soluble copper containing wood preservatives was to incorporate other salts. PCT patent application WO 92/19429, published Nov. 12, 1992, in Example 2, describes a method of treating an article of prepared wood by immersing it for 20 minutes in a bath of 1800 C linseed oil containing a drying agent, or drier, of 0.07% lead, 0.003% manganese and 0.004% calcium naphthenate, 0.3% copper naphthenate, and 0.03 zinc naphthenates as an insecticide and fungicide. Others have tried alternative metal-compounds, including silver. None of these have found commercial acceptance.

Fojutowski, A.; Lewandowski, 0, Zesz. Probl. Postepow Nauk Roln. No. 209: 197-204 (1978), describes fungicides comprising fatty acids with copper compounds, applied by dipping hardboard heated to 1200 C into a bath of the fungicide, also maintained at 1200 C. This is not practicable for a variety of reasons. In "A New Approach To Non-Toxic, Wide-Spectrum, Ground-Contact Wood Preservatives, Part 1. Approach And Reaction Mechanisms," HOLZFORSCHUNG Vol. 47, No. 3, 1993, pp. 253-260, it is asserted that copper soaps, made with the carboxylic acid groups from unsaturated fatty acids of non-toxic vegetable oils, rosin, and from synthetic unsaturated polyester resins have effectiveness and long-term durability as ground contact wood preservatives for use against termites and fungal attack. These are not yet in widespread use, and are expected to have high leach rates and the bio-available fatty acids are expected to encourage some molds.

The solubility of copper preservatives can be controlled by using, for example, an oil barrier. But these oils can unfavorably change the color, appearance, and burning properties of the wood, and can be strong irritants. Oil-soaked wood containing oil-soluble biocides like chlorothalonil, e.g., utility poles, are highly resistant to leaching and biological attack, but the appearance of this wood is not acceptable for most uses. Japanese Patent Application 08183,010 JP, published in 1996, describes a modified wood claimed to have mildew-proofing and antiseptic properties and ant-proofing properties, made by treating wood with a processing liquid containing a copper salt and linseed oil or another liquid hardening composition. U.S. Pat. No. 3,837,875 describes as a composition for cleaning, sealing, preserving, protecting and beautifying host materials such as wood a mixture of boiled linseed oil, turpentine, pine oil, a dryer and 28 parts per million of metallic copper. Feist and Mraz, Forest Products Lab Madison Wis., Wood Finishing: Water Repellents and Water-Repellent Preservatives. Revision, Report Number-FSRN-FPL-0124-Rev (NTIS 1978) discloses preservatives containing a substance that repels water (usually paraffin wax or related material), a resin or drying oil, and a solvent such as turpentine or mineral spirits. Addition of a preservative such as copper naphthenate to the water repellent is asserted to protect wood surfaces against decay and mildew organisms. Soviet Union Patent No. SU 642166 describes a wood surface staining and preservation treatment, carried out by impregnating wood with an aqueous copper salt solution, followed by thermal treatment in boiling drying oil containing 8-hydroxyquinoline dye. U.S. published application 20030108759 describes injecting a copper ammonium acetate complex and a drying oil as a wood preservative. Again, oil is not favored as it can alter burning characteristics of wood, can be staining and/or discoloring, and can be an irritant. It is also difficult to work with and to inject into wood. None of the above methods of preserving wood have met commercial acceptance.

U.S. Pat. No. 6,521,288 describes adding certain organic biocides to polymeric nanoparticles (particles), and claims benefits including: 1) protecting the biocides during processing, 2) having an ability to incorporate water-insoluble biocides, 3) achieving a more even distribution of the biocide than the prior art method of incorporating small particles of the biocide into the wood, since the polymer component acts as a diluent, 4) reducing leaching with nanoparticles, and 5) protecting the biocide within the polymer from environmental degradation. The application states that the method is useful for biocides including chlorinated hydrocarbons, organometallics, halogen-releasing compounds, metallic salts, organic sulfur compounds, and phenolics, and preferred embodiments include copper naphthenate, zinc naphthenate, quaternary ammonium salts, pentachlorophenol, tebuconazole, chlorothalonil, chlorpyrifos, isothiazolones, propiconazole, other triazoles, pyrethroids, and other insecticides, imidichloprid, oxine copper and the like, and also nanoparticles with variable release rates that incorporate inorganic preservatives as boric acid, sodium borate salts, zinc borate, copper salts and zinc salts. The only examples used the organic biocides tebuconazole and chlorothalonil incorporated in polymeric nanoparticles. There is no enabling disclosure relating to any metal salts. While data was presented showing efficacy of tebuconazole/polymeric nanoparticle formulations and chlorothalonil/polymeric nanoparticle formulations in wood, the efficacy of these treatments was not compared to those found when using other methods of injecting the same biocide loading into wood. Efficacy/leach resistance data was presented on wood product material, where it was found that the nanoparticle/biocide treated wood had the same properties as the wood product treated with a solution of the biocide, i.e., the polymeric nanoparticles had no effect. Finally, it is known in the art that transport of preservative material is a large cost item, and diluents will merely exacerbate this problem.

We have discussed the problems with current systems, e.g., they add undesired oil; they increase corrosion; they are dilute; they are expensive, especially when the metal-based biocides must be combined with large quantities of organic biocides; the high copper leach rates are both a serious environmental problem in itself and will almost certainly decrease the longevity of treatment below that obtained with CCA. However, cost is a primary factor in the selection of a wood preservative. The market is accustomed to the low cost and effectiveness of CCA, and the market is not ready to bear the incremental costs of large amounts of expensive biocides and other materials such as polymeric nanoparticles.

SUMMARY OF THE INVENTION

The principal aspect of the invention is the copper-based particulate preservative treatment for wood and wood products. One embodiment of this invention is an effective, long-lasting, environmentally responsible, non-staining/coloring, inexpensive, non-corrosion inducing, injectable, substantially crystalline (or amorphous sparingly soluble), copper-based particulate preservative treatment for wood and wood products that is substantially free of hazardous material. Yet another embodiment of the invention is an effective, long-lasting, environmentally responsible, non-staining/coloring, inexpensive, non-corrosion-inducing, injectable, substantially crystalline (or amorphous sparingly soluble), zinc-based particulate preservative treatment for wood and wood products that is substantially free of hazardous material. This zinc-based particulate composition can be used independently of the copper-based particulates, but in preferred embodiments is used in combination with one or more copper-based particulates. In preferred embodiments, the substantially crystalline (or amorphous sparingly soluble) copper- and/or zinc-based particulates are injected in a formulation comprising one or more organic biocides. As used herein, the term "organic biocide" also includes organometallic biocides.

One aspect of the present invention relates to a preservative that may be used to preserve wood and wood products. In one embodiment, a preservative of the invention is a copper-based preservative. In a preferred embodiment, the copper-based preservative comprises copper-based particles. Exemplary particles comprise, for example, copper hydroxide, a copper salt, and a copper oxide.

In one embodiment, the copper-based particles comprise a substantially crystalline copper compound. At least about 20%, 30%, 50%, or 75% of the weight of the copper-based particles may be composed of the substantially crystalline copper compound. In another embodiment, essentially all of the weight of the copper-based particles is composed of substantially crystalline copper compound. The substantially crystalline copper compound may comprise, for example, at least one of copper hydroxide (such as $Cu(OH)_2$), a copper salt, and a copper oxide (such as CuO).

Exemplary copper-based particles of the invention are sufficiently small to be present within wood without a substantial reduction in the original strength of the wood. For example, substantially all of the copper-based particles may be sized to occupy pores or vesicles of wood. In one embodiment, wood or a wood product may be impregnated with copper-based particles of the invention.

Copper or copper-based particles present within wood or wood products is preferably less mobile than copper present in a liquid without copper-based particles of the invention. Preferably, the copper-based particles are sufficiently insoluble so as to not be easily removed by leaching but are sufficiently soluble to exhibit toxicity to primary organisms primarily responsible for the decay of the wood. Exemplary copper-based particles of the invention are sufficiently small to be present within wood without a substantial reduction in the original strength of the wood. For example, substantially all of the copper-based particles may be sized to occupy pores or vesicles of wood. In one embodiment, exemplary wood preservatives comprise copper-based particles having a size distribution in which at least 50% of particles have a diameter smaller than 0.25 µm, 0.2 µm, or 0.15 µm. A preferred particle sizing technique is a sedimentation or centrifugation technique based on Stoke's Law.

Another embodiment of this invention is an effective, long-lasting, environmentally responsible, non-staining/coloring, inexpensive, less-corrosion-inducing, injectable, sparingly soluble copper salt-containing particulate preservative treatment for wood and wood products that is substantially free of hazardous material. Generally, crystalline salts are preferred because they have lower rates of dissolution than do their amorphous analogs. However, amorphous salts are equally effective, and particulates made from amorphous salts can be treated with one or more coatings, or can be made of a particular size, such that the amorphous material may easily have release and leach characteristics like the substantially crystalline salts. Substantially crystalline salts should be considered a preferred variant of the invention, as the same disclosure is generally equally applicable to amorphous sparingly soluble copper salts, or substantially amorphous sparingly soluble copper salts. A "sparingly soluble salt" has, for example, a $K_{sp}$ less than about 1 E-8, preferably between about 1 E-IO to about 1 E-21.

DETAILED DESCRIPTION OF THE INVENTION

Figure 1:
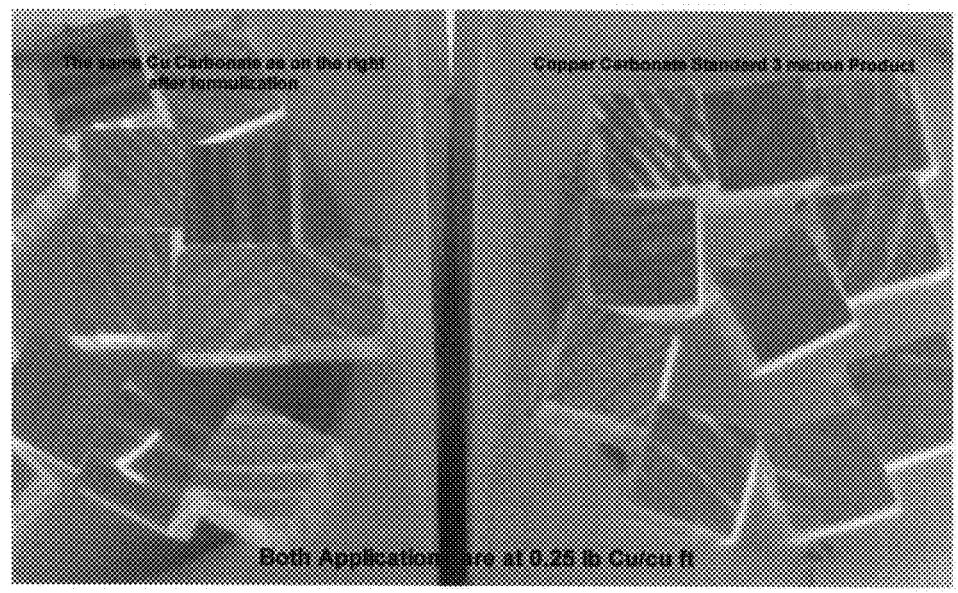
FIG. 1 is a photograph of wood injected with the composition of this invention compared to wood injected by a prior art composition.

The copper-based particulates can comprise or consist essentially of any sparingly soluble substantially crystalline (or sparingly soluble amorphous) copper salts. In one embodiment the substantially crystalline (or amorphous sparingly soluble) copper salts in the copper-based particulates comprise or consist essentially of one or more copper salts selected from copper hydroxides; copper carbonates (e.g., "yellow" copper carbonate); basic (or "alkaline") copper carbonates; basic copper sulfates including particularly tribasic copper sulfate; basic copper nitrates; copper oxychlorides (basic copper chlorides); copper borates; basic copper borates; copper ferricyanate; copper fluorosilicate; copper thiocyanate; copper diphosphate or copper pyrophosphate, copper cyanate; and mixtures thereof. In one embodiment, the copper based particles comprise a substantially crystalline copper compound. At least about 20%, 30%, 50%, or 75% of the weight of the copper-based particles may be composed of the substantially crystalline copper compound(s).

In a preferred embodiment the substantially crystalline (or amorphous sparingly soluble) copper salts in the copper-based particulates comprise or consist essentially of one or more copper salts selected from copper hydroxides; copper carbonates, basic (or "alkaline") copper carbonates; basic copper sulfates including particularly tribasic copper sulfate; basic copper nitrates; copper oxychlorides (basic copper chlorides); copper borates, basic copper borates, and mixtures thereof. In one embodiment, the copper-based particles comprise a substantially crystalline copper compound. At least about 20%, 30%, 50%, or 75% of the weight of the copper-based particles may be composed of the substantially crystalline copper compound.

In another embodiment the substantially crystalline (or amorphous sparingly soluble) copper salts in the copper-based particulates in a wood preservative formulation can comprise or consist essentially of a plurality of sparingly soluble substantially crystalline (or amorphous sparingly soluble) copper salts selected from copper oxide, copper hydroxides; copper carbonates, alkaline (or "basic") copper carbonates; alkaline copper sulfates; alkaline copper nitrates; copper oxychlorides; copper borates, basic copper borates, and mixtures thereof, with the proviso that at least one of the substantially crystalline (or amorphous sparingly soluble) copper salts is not a copper oxide. Of the copper oxides, $Cu_2O$ is preferred over CuO. In a variant of this, the copper-based particulate material can comprise or consist essentially of one or more sparingly soluble substantially crystalline copper salts selected from copper hydroxides; copper carbonates, alkaline (or "basic") copper carbonates; alkaline copper nitrates; alkaline copper sulfates; copper oxychlorides; copper borates, basic copper borates, and mixtures thereof. In one embodiment, the copper-based particles comprise a substantially crystalline copper compound. At least about 20%, 30%, 50%, or 75% of the weight of the copper-based particles may be composed of the substantially crystalline copper compound(s).

In any of the above, the substantially crystalline (or amorphous sparingly soluble) copper composition can have a substantial amount of one or more of magnesium, zinc, or both, wherein these cations are either dispersed within the substantially crystalline (or amorphous sparingly soluble) copper composition or a separate phase within a particulate. In preferred embodiments of the invention, at least some particulates comprise copper hydroxide, basic copper carbonate, or both. In more preferred embodiments, the copper hydroxide comprises between 6 and 20 parts of magnesium per 100 parts of copper, for example between 9 and 15 parts of magnesium per 100 parts of copper. Alternatively, in another more preferred embodiments, the copper hydroxide comprises between 6 and 20 parts total of magnesium and zinc per 100 parts of copper, for example between 9 and 15 parts total of magnesium and zinc per 100 parts of copper. In some embodiments, the basic copper carbonate comprises between 6 and 20 parts of magnesium per 100 parts of copper, for example between 9 and 15 parts of magnesium per 100 parts of copper, or alternatively between 6 and 20 parts total of magnesium and zinc per 100 parts of copper, for example between 9 and 15 parts total of magnesium and zinc per 100 parts of copper.

Alternatively or additionally, in a preferred embodiment, the copper hydroxide and/or basic copper carbonate comprises between about 0.01 and about 5 parts of phosphate per 100 parts of copper, for example between 9 and 15 parts of phosphate per 100 parts of copper.

In another preferred embodiment, the slurry comprises sparingly soluble copper salt particulates and also comprises zinc borate particulates. Preferably, at least some of the sparingly soluble copper salt-based particulates comprise copper borate. It is known to use a two stage process where a zinc or copper salt is injected into the wood followed by a second step wherein the borax is injected and the insoluble metal borate is formed in situ. Such a complicated, time-consuming, and therefore expensive process in not sufficiently cost-effective. As the solubility of copper borate is very pH sensitive, in a preferred embodiment the sparingly soluble copper salts comprise an alkaline material, e.g., copper hydroxide or copper carbonate, to reduce the solubility of the copper borate. The zinc borate loading can range from 0.025% to 0.5%, for example, independent of the copper loading in the wood.

In any of the above-described embodiments, the substantially crystalline copper composition in copper-based particulates and/or copper-based particulate material can further comprise one or more soluble substantially crystalline copper salts, for example copper sulfate, copper fluoroborate; copper fluoride, or mixtures thereof, where the soluble substantially crystalline copper salts phase is stabilized against dissolution.

In any of the above-described embodiments, the substantially crystalline copper composition in copper-based particulates and/or copper-based particulate material can further comprise the substantially insoluble copper salt copper phosphate, $Cu_3(PO_4)_2$. In any of the above-described embodiments, the copper composition in copper-based particulates and/or copper-based particulate material can further comprise the insoluble copper salt copper 8-quinolinolate. In any of the above-described embodiments, the composition can further comprise copper quinaldate, copper oxime, or both in particulate form. If there are copper-based particulates substantially comprising $Cu_3(PO_4)_2$ and/or copper oxide and/or copper 8-quinolinolate, the particulates should be exceedingly small, e.g., less than about 0.07 microns, preferably less than about 0.05 microns, to provide maximum surface area to help dissolution of the particles, and the wood treatment should contain another type of substantially crystalline (or amorphous sparingly soluble) copper-based particulates, e.g., basic copper carbonate, basic copper borate, tribasic copper sulfate, copper hydroxides, and the like.

The zinc analogs of the above are useful for the zinc-based particulates of the alternate embodiments of the invention. In one embodiment the copper-based particulate material can further comprise one or more of crystalline zinc salts selected from zinc hydroxide; zinc oxides; zinc carbonate; zinc oxychloride; zinc fluoroborate; zinc borate, zinc fluoride, or mixture thereof. The zinc salts may be in a separate salt phase, or may be mixed CU/Zn salts, or combinations thereof. In preferred embodiments the particle comprises at least about 40%, preferably at least about 60%, and more preferably at least about 80% by weight of one or more substantially crystalline (or amorphous sparingly soluble) copper salts, crystalline zinc salts, or mixtures or combinations thereof.

In one embodiment the copper-based particulate preservative treatment for wood can further comprise zinc-based particulates comprising one or more of crystalline zinc salts selected from zinc hydroxide; zinc oxides; zinc carbonate; zinc oxychloride; zinc fluoroborate; zinc borate, zinc fluoride, or mixture thereof. The preferred zinc-based substantially crystalline material are zinc hydroxide, zinc borate, zinc carbonate, or mixture thereof, which may be doped with other cations, e.g., from 0.1 to 10% copper, from 0.1 to 10% magnesium, or both, for example, based on the total weight of the cations in the substantially crystalline (or amorphous sparingly soluble) material. In preferred embodiments the particle comprises at least about 40%, preferably at least about 60%, and more preferably at least about 80% by weight of one or more crystalline zinc salts.

Preferred embodiments of the invention comprise particles comprising one or more of copper hydroxide, alkaline copper carbonate, alkaline copper oxychloride, tribasic copper sulfate, copper borate, or mixtures thereof. The most preferred embodiments of the invention comprise particles comprising copper hydroxide, alkaline copper carbonate, copper borate, alkaline copper borate, or mixtures thereof.

Metal salt-based preservatives require added organic biocides to have the efficacy of the traditional CCA treatments. It is believed that certain organic biocides are very effective against most (but not all) undesired bio-organisms, and is also long-lasting. A principal function of the copper in such a system is to inhibit growth of those bio-organisms that degrade the organic biocides and/or that are resistant to the organic biocides. The most preferred embodiments of this invention have copper-based particulates and optionally one or more of zinc-based particulates and tin-based particulates, and further comprise between about 0.01% to about 20% by weight total of one or more organic biocides. In addition, in some embodiments, the particulates provide a carrier to carry the organic biocides into the wood and help ensure the biocide is well-distributed throughout the wood. Preferred embodiments of the invention are an injectable copper-based particulate preservative treatment for wood that further comprises one or more injectable organic biocides attached to particulates.

Other aspects of this invention include methods to prepare the copper-based particulates, methods of formulating the injectable wood treatment compositions that comprise the copper-based particulates and optionally one or more organic biocides, methods of transporting the injectable wood treatments, methods of mixing and injecting the copper-based particulate wood preservative composition, and also wood and wood products treated with the copper-based particulate preservative treatment compositions.

We believe our combination of manufacture, pretreatment, formulation and injection into wood of basic ("sparingly soluble") crystalline copper compounds injected as particulates represent a significant discovery. The slurries of this invention are essentially unaffected by the use of hard water in the application. The CMC material used in the prior art precipitates an objectionable residue of calcium and magnesium carbonates onto the surface of the wood. Injection of the present formulation uses the standard operating procedure that is commonly practiced in the industry. No changes are needed. The present formulation eliminates the nitrogen content of the prior art products; and we believe the nitrogen is associated with the enhanced rate of sapstain growth which presently necessitates the use of expensive sapstain control agents. Removal of the fraction of particles having a diameter greater than 1 micron (1000 nanometers), accomplished with a component of this technology, means the slurries are stable—slurry particles settle over the course of days or even weeks. This is a desirable application feature. The copper should be relatively non-leachable, being comparable with the rates associated with the CCA products. Due to lower leach rates, the product should be usable underground, near waterways, and also in marine applications. The cost per pound of copper is estimated to be between $0.20 to $0.50 less than present copper-MEA-carbonate products. We believe that corrosivity of the product will be less than that associated with the copper-MEA-carbonate products. Freight should be only one third that associated with the copper-MEA-carbonate products.

Unless otherwise specified, all compositions are given in "percent", where the percent is the percent by weight based on the total weight of the entire component, e.g., of the particle, or to the injectable composition. In the event a composition is defined in "parts" of various components, this is parts by weight, wherein the total number of parts in the composition is between 90 and 110.

Effective—

By "effective" we mean the preservative treatment is sufficiently distributable through the wood product, and is sufficiently soluble and available so as to provide a bio-active concentration of copper ions in the wood matrix. By "bio-active" we mean the preservative treatment is sufficiently biocidal to one or more of fungus, mold, insects, and other undesired organisms which are normally the target of copper-containing wood preservatives such that these organisms avoid and/or can not thrive in the treated wood. It is known that copper arsenate ($Cu_3(AsO_4)_2$) injected as a molecular layer is an effective biocide. Therefore, the particulate preservative treatment should provide a copper concentration roughly similar (for example, about the same to about two times as high) as that provided by the chromated copper arsenate (CCA) treatment. Too low a solubility, and the copper is not bioactive. At the same time, the injectable copper-based wood preservative treatment of this invention is intended to have one or more organic-based biocides incorporated therewith in amounts the same as are currently being used with soluble copper preservatives, and efficacy is based on the combination of the copper (and/or zinc) component in combination with the organic biocides.

Long-Lasting—

By "long-lasting" we mean the preservative treatment has an effective life of at least about the same as a traditional CCA-treated product, alternatively, the treatment lasts at least about 20 years under normal outdoor ground-contact use, for example. Too high a solubility of the particulates, and the copper is leached out of the wood at too fast a rate. Such fast leaching creates environmental problems, i.e., the leached copper contaminates the environment, and also longevity problems, i.e., so much copper may be leached from the wood that the remaining treatment can no longer provide a bio-active concentration of copper ions.

Leaching is a function of particle size and the solubility of the substantially crystalline (or amorphous sparingly soluble) copper-containing material. Larger size particles have lower leach rates, while particles in a size range from 1 to 10 nanometers under certain circumstances will not have a leach rate much different than that of an injected copper salt solution. In preferred embodiments of this invention, at least 50% by weight of the copper-containing particulates have a size greater than 40 nanometers. In more preferred embodiments, at least 50% by weight of the copper-containing particulates have a size greater than 80 nanometers. In one preferred embodiment, at least 80% by weight of the copper-containing particulates have a size between 0.05 microns and 0.4 microns.

Leaching is not the only mechanism whereby material can be flushed from wood. Because the material is in particulate form, there is a possibility that particulates will be flushed from the wood. Evidence suggests that very small substantially spherical nanoparticles, i.e., spherical particles of size 5 to 20 nanometers, can migrate freely through a wood matrix.

United States Patent Application 20030077219 teaches a variant of the precipitation method of forming nanoparticles from micro-emulsions, the invention apparently relating to a block polymer used to stabilize the micro-emulsions. This publication claims that nanoparticles penetrate more easily and more deeply into the wood layers under treatment due to their "quasi atomic size," thus eliminating or reducing the need for pressure impregnation. Immersion of wood into a copper hydroxide micro-emulsion showed the copper hydroxide penetrated to a depth of more than 10 to 298 mm. However, while said particles are easy to inject, they are also clearly easily transported through wood and would be easily flushed from the wood. These wood preservative treatments would not be long-lasting. Therefore, in preferred embodiments of the invention the material is substantially free of substantially spherical particulates, wherein the size of the spherical particulates is less than about 20 nanometers, particularly less than 15 nanometers.

Generally, the leaching rate from dispersed particulates is controlled by 1) diffusion and boundary layer effects around the limited surface area available to water; 2) the activation energy needed to disrupt the crystal and to thereby cause dissolution, and 3) the absolute solubility of the material. Solubility is not an easy parameter to control; the solubility of copper itself in compositions containing hydroxyl groups and carbonates is about 0.01 ppm at pH 10, 2 ppm at pH 7, but is 640 ppm at pH 4. Wood itself has a "pH" between 4 and 5, but there is essentially no buffering capacity. Therefore, copper hydroxides are a component of the preferred substantially crystalline (or amorphous sparingly soluble) copper material, as the hydroxides will raise the pH of the water in the wood.

Leaching will be discussed extensively infra. Advantageously, the particulates of the present invention provide at 240 hours into an AWPA E11-97 leach test a total leached copper value that is within a factor of two above, to within a factor of five below, preferably within a factor of three below, the total leached copper value obtained by a wood sample treated with CCA and subjected to the same test.

Substantially Free of Hazardous Material—

By "substantially free of hazardous material" we mean the preservative treatment is substantially free of materials such as lead, arsenic, chromium, and the like. By substantially free of lead we mean less than 0.1% by weight, preferably less than 0.01% by weight, more preferably less than 0.001% by weight, based on the dry weight of the wood preservative. By substantially free of arsenic we mean less than 5% by weight, preferably less than 1% by weight, more preferably less than 0.1% by weight, for example less than 0.01% by weight, based on the dry weight of the wood preservative. By substantially free of chromium we mean less than 0.5% by weight, preferably less than 0.1% by weight, more preferably less than 0.01% by weight, based on the dry weight of the wood preservative.

Environmentally Responsible—

By "environmentally responsible" we mean the wood preservative (including co-biocide) has a bioactive effectiveness that is at least about one half that of CCA, preferably at least three quarters of that of CCA, for example, about equal to that of CCA, for specified organism based on the weight percent of the wood preservative material in the wood. If, for instance, the wood preservative has a bioactive effectiveness equal to that of CCA, then wood treated with a selected concentration of the wood preservative will have substantially similar bioactivity as wood treated with the same concentration of CCA.

Additionally, the environmentally responsible material is substantially free of small nanoparticles which can be readily flushed from wood. Therefore, in preferred embodiments of the invention the environmentally responsible material is substantially free of substantially spherical particulates, wherein the size of the spherical particulates is less than about 20 nanometers, particularly less than 5 nanometers. More preferably, in preferred embodiments of the invention the environmentally responsible material is substantially free of particulates having a size less than about 20 nanometers, particularly less than 5 nanometers. Nanoparticle-sized metal particulates may be toxic to certain aquatic life, though the data is very preliminary.

Additionally, environmentally responsible wood preservatives are beneficially substantially free of organic solvents. By substantially free we mean the treatment comprises less than 10% organic solvents, preferably less than 5% organic solvents, more preferably less than 1% organic solvents, for example free of organic solvents, based on the weight of the copper in the wood preservative.

Injectable—

By "injectable" we mean the wood preservative particulates are able to be pressure-injected into wood, wood products, and the like to depths normally required in the industry, using equipment, pressures, exposure times, and procedures that are the same or that are substantially similar to those currently used in industry. Pressure treatment is a process performed in a closed cylinder that is pressurized, forcing the chemicals into the wood. Copper loading, also called copper retention is a measure of the amount of preservative that remains in the wood after the pressure is released. It is given as "pcf," or pounds of preservative per cubic foot of wood. Retention levels that must be reached are dependent on three variables: the type of wood used, the type of preservative used, and the use of the wood after treatment. The sparingly soluble copper-salt particulates of this invention are typically expected to be added to wood in an amount equal to or less than 0.25 pounds as copper per cubic foot. In preferred embodiments of the invention incising is not expected to be required to inject the slurries of the present invention into lumber having thicknesses of 6 to 10 inches.

Injectability requires the particulates be substantially free of the size and morphology. that will tend to accumulate and form a filter cake, generally on or near the surface of the wood, that results in undesirable accumulations on wood in one or more outer portions of the wood and a deficiency in an inner portion of the wood. Injectability is generally a function of the wood itself, as well as the particle size, particle morphology, particle concentration, and the particle size distribution.

The requirements of injectability for substantially round, e.g., the diameter is one direction is within a factor of two of the diameter measured in a different direction, rigid particles generally are 1) that substantially all the particles, e.g., greater than 98% by weight, have a particle size with diameter equal to or less than about 0.5 microns, preferably equal to or less than about 0.3 microns, for example equal to or less than about 0.2 microns, and 2) that substantially no particles, e.g., less than 0.5% by weight, have a diameter greater than about 1.5 microns, or an average diameter greater than about 1 micron, for example. We believe the first criteria primarily addresses the phenomena of bridging and subsequent plugging of pore throats, and the second criteria addresses the phenomena of forming a filter cake. Once a pore throat is partially plugged, complete plugging and undesired buildup generally quickly ensues.

However, there are minimum preferred particulate diameters for the wood treatment, which depend somewhat on the copper salt(s) that are in the particulates. If the salts have a high solubility, very small particulates having a large surface to mass ratio will result in too high a copper ion concentration, and too fast a copper leaching, compared to preferred embodiments of this invention. Further, very small particulates, especially for example small spherical particles of diameter between about 0.003 to about 0.02 microns, are readily flushed from the wood. Generally, it is preferred that at least 80% by weight of the particles be above 0.01 microns in diameter, preferably greater than 0.03 microns, for example greater than 0.06 microns in diameter.

By injectable, unless otherwise specified, we mean injectable into normal southern pine lumber. This invention also encompasses injecting the particulates into other woods as well as into for example heartwood. Selected other woods and heartwood may require a smaller substantially lower criteria on particle dimensions for injectability, and such formulations can be made as discussed herein, but the formulation most of interest is a commercially operative formulation developed for normal Southern Pine. Such a formulation will typically be useful for all other woods, with the possible exception of selected heartwood. Such problems with heartwood are normally not a substantial concern, as the injected particulate material may form a partial protective filter cake around heartwood that protects the heartwood without causing unsightly accumulations of preservative on the wood, and also heartwood is naturally substantially resistant to attack by many bioorganisms and therefore may require less copper to constitute sufficient protection.

We have found three methods to improve injectability and/or to maintain injectability of particulates. These methods improve particle size distribution and/or morphology by wet milling, and chemically and physically stabilize the particulates by coating the particulates with selected materials.

Non-Staining/Non-Coloring—

By "non-staining/non-coloring" we mean the wood preservative does not impart undesired color to the wood. Large particulates, or large agglomerations of smaller particulates, impose a visible and undesired color to the treated wood, which is generally bluish or greenish. Surprisingly, coloring is usually indicative of poor injectability. Individual particles of diameter less than about 1 micron, preferably less than 0.5 microns, that are widely dispersed in a matrix do not color a wood product to any substantial degree. Filter cake forms unsightly coloring. An aggregation of particles, similar to filter-cake, could contribute un-wanted color. Preferably 100% by weight of the particles have an average diameter of less than 1 micron, where an average diameter is the diameter measured by Stokes law settling (which may be assisted by centrifugation), or by preferably by dynamic light (X-ray) scattering or by Doppler light scattering. Even particulates having a size greater than 0.5 microns can impart very visible color, and agglomerates of similar size have the same effect as do large particles. In a preferred embodiment of the invention, at least about 95%, e.g., at least about 99% by weight of the particulates/aggregates are smaller than 0.5 microns in average diameter. More preferably, at least about 95%, e.g., at least about 99% by weight of the particulates/aggregates are smaller than 0.35 microns in average diameter. Even more preferably, at least about 95%, e.g., at least about 99% by weight of the particulates/aggregates are smaller than 0.3 microns in average diameter. Generally, it is preferred that at least 90% by weight of the particles be above 0.01 microns in diameter, preferably greater than 0.03 microns, for example greater than 0.06 microns. Certain compounds, particularly basic copper carbonate, copper hydroxide, and copper oxychloride are preferred because they impart less color than do other particles of comparable size. Additionally, the presence of a zinc salt, a magnesium salt, or both either as a separate phase or as a mixed phase may also reduce color.

Inexpensive—

By "inexpensive" we mean the wood preservative is prepared using techniques so that the cost of the wood treatment is competitive with, for example, copper-ethanolamine-complex treatments and other commonly used treatments. As the cost of copper is substantially constant regardless of the source, inexpensive relates primarily to the costs of manufacture, separation, sizing, and preservation of the particulate material. There are many techniques to create very small nanoparticles, but most of these processes are far too costly to be useful in the mass production of a copper-based wood preservative treatment. Generally, the term "inexpensive" means at a processed cost less than or equal to the current costs of the soluble copper-co-biocide treatments, alternately within about 20% of the cost of prior art CCA treatments.

The preferred method of production is a precipitation process, in the absence of organic solvents and the like. Preferably the reactants are of standard industrial quality, as opposed to higher levels of purity. The particles start with certain characteristics including size distribution and morphology, e.g., at least 2% by weight of the particles have a diameter greater than 1 micron, usually greater than 1.5 microns, and generally must undergo subsequent treatment, e.g., milling, to make sure the particle size and particle size distribution are favorable for injection. Particles made by other processes, particularly emulsion precipitation processes and fuming processes, are not sufficiently cost effective to manufacture commercially acceptable copper particulates for wood preservation.

It is known that nanoparticles can be formed for example by micro-emulsion (or micelle) precipitation, and the like. The micelle system, where emulsions of small and uniformly sized micelles are used as nanoreactors in which the deposition of the metal salt is carried out, are known in the art. For example, it is known to make nickel and nickel/copper (7/3) carbonate particles via water in oil (hexane/hexanol) microemulsions. Two separate microemulsions with the metal salt and ammonium bicarbonate, respectively, were prepared and mixed rapidly to form metal carbonate nanoparticles of 6 to 7 nm diameter with a small diameter distribution. Such processes, while useful in forming very small particulates, are not useful in forming commercially acceptable wood preservative. The associated costs of adding and removing the solvents used to form the emulsions makes these processes economically un-usable for the purpose of forming a copper-containing injectable particulate wood preservation material.

It is known that nanoparticles can be formed for example by forming fumed copper salts via a vapor process or an aerosol oxidation process. The authors of Copper and Copper Oxide Nanoparticle Formation by Chemical Vapor Nucleation From Copper (II) Acetylacetonate by Albert G. Nasibulin, P. Petri Ahonen, Olivier Richard, Esko I describe methods of forming e.g., 2 nm to 20 nm in diameter nanoparticles. Generally, fuming processes are limited to producing the oxides of copper, as these authors produced. Again, the cost of obtaining such small size (and narrow particle distribution) is not justified by any increase in efficacy of the particles for most copper salts of this invention.

The cost of polymeric nanoparticles to act as a carrier for the copper salts is similarly not justifiable.

Less-Corrosion-Inducing—

The commercial soluble copper containing wood preservatives often result in increased metal corrosion, for example of nails within the wood. Preserved wood products are often used in load-bearing out-door structures such as decks. Traditional fastening material, including aluminum and standard galvanized fittings, are not suitable for use with wood treated with these new preservatives. Many regions are now specifying that hardware, e.g., fittings, nails, screws, and fasteners, be either galvanized with 1.85 ounces zinc per square foot (a G-185 coating) or require Type 304 stainless steel. Generally, the presence of any salt will induce corrosion. By "less-corrosion-inducing" we mean the wood preservative has a reduced tendency, compared to a similar concentration of copper obtained from the soluble copper treatments such as the amine-copper-complex treatments and alkanolamine-copper-complex treatments in use today, to corrode metal that contacts the wood. The degree of corrosion will depend in large part on the salts selected, as well as on adjuvants, in particular amines.

We believe that the amines present in the treatments used in soluble copper treatments-alkanolamines, ammonia, and the like—are corrosive to metals. We also believe that another problem with the new soluble complexed copper preservatives is that they are, or they eventually turn into, biodegradable material that can encourage certain biological attacks, particularly mildew. The commonly used soluble copper compounds provide nitrogen-containing nutrients (amines) which are believed to act as food-stuff and causes an increase in the presence of sapstain molds, therefore requiring additional biocides effective on sapstain molds to be added to protect the external appearance of the wood. When there is also bio-available carbon sources, in addition to bio-available nitrogen, the problem is made worse. Advantageously, the wood preservative is substantially free of any amines other than certain selected amines that may be used as a supplemental biocide. By substantially free we mean the treatment comprises less than 10% amines, preferably less than 5% amines, more preferably less than 1% amines, for example free of amines, based on the weight of the copper in the wood preservative. Alternatively, the term means there is less than one amine molecule or moiety per four copper atoms, preferably less than one amine molecule or moiety per ten copper atoms. Again, amines that are used as supplemental biocides, if any, are excluded from this limitation. While basic copper nitrate is a useful sparingly soluble copper salt for use in this invention, in most embodiments of the invention the wood preservative is also substantially free of nitrates.

In other embodiments of the invention an injectable copper-based particulate preservative treatment for wood that is substantially free of bio-available nitrogen, and even more preferably substantially free of bio-available nitrogen and bio-available carbon is provided. By substantially free of bio-available nitrogen we mean the treatment comprises less than 10% of nitrates and organic nitrogen, preferably less than 5% of nitrates and organic nitrogen, more preferably less than 1% of nitrates and organic nitrogen, for example less than 0.1% of nitrates and organic nitrogen, based on the weight of the copper in the wood preservative. In most of the soluble or complexed copper treatments, there are between 1 and 4 atoms of organic nitrogen that act as a complexer or carrier for one atom of copper. In the preferred embodiments of this invention, there is less than 0.3 atoms, preferably less than 0.1 atoms, for example less than 0.05 atoms of organic nitrogen per atom of copper in the wood preservative treatment. Again, organic nitrogen-containing compounds that are used specifically as supplemental biocides are excluded from this limitation. By substantially free of bio-available carbon we mean the treatment comprises less than 30% of bio-available organic material (defined as material that is degradable or that will during the lifespan of the treatment will become degradable), preferably less than 10% of bio-available organic material, more preferably less than 1% of bio-available organic material, based on the weight of the copper in the wood preservative. Again, organic compounds that are used as supplemental biocides, if any, are excluded from this limitation. It is believed that the presence of bio-available organic carbon may encourage the growth of certain molds.

In one embodiment, the copper-based particles are substantially free of polymers, such as organic polymers. For example, copper-based particles of the invention may be substantially free of one or more of polyvinylpyridine, polymethacrylate, polystyrene, polyvinylpyridine/styrene copolymers, polyesters, polyethylene, polypropylene, polyvinylchloride, blends of the above homopolymers with acrylic acid and the like. By substantially free, it is meant that the copper-based particles are less than about 50% by weight polymer. The copper-based particles may be less than about 35% by weight polymer, for example, less than 25% by weight polymer, such as less than 15% by weight polymer. In one embodiment, the copper-based particles are essentially free of polymer, by which it is meant the copper-based particles comprise less than about 5% by weight polymer. In one embodiment, the copper-based particles comprise less than about 2.5% by weight polymer. In one embodiment, the copper-based particles are free of polymer.

In one embodiment of the invention, the copper-based particles may comprise a polymer. In this embodiment, the ratio of the weight of copper present in the particles to polymer present in the particles may be at least about 1 to 1, for example at least about 2 to 1, 4 to 1, 5 to 1, 7 to 1, or at least about 10 to 1. For example, if ratio of the weight of copper present in the particles to the weight of polymer present in the particles is at least about 2 to 1, the particles comprise at least about twice as much copper by weight as polymer.

Substantially Crystalline—

By "substantially crystalline" we mean, for example, greater than about 30%, preferably greater than about 50%, by weight of the material of interest (copper salt, zinc salt, and the like) is crystalline. A material is substantially crystalline if the material gives the distinctive X-ray diffraction patterns of the crystalline entity (relating to d spacing, not present in the amorphous material). A convenient technique for assessing the crystallinity relative to the crystallinity of known crystalline salts is the comparison of the relative intensities of the peaks of their respective X-ray powder diffraction patterns. The degree of crystallinity can be determined by, for example, determining the sum of the X-ray diffraction peak heights (for the same sample size), in terms of arbitrary units above background, and comparing the summed peak heights of the substantially crystalline material in, for example, the copper-based particulates with the corresponding peak heights of the known crystalline material. This procedure utilizes, for example, only the strongest 4 peaks. When, for example, the numerical sum of the peak heights of the material in a particulate is 30 percent of the value of the sum of the peak heights of the same known crystalline copper salt, then the product is 30 percent crystalline and is substantially crystalline. The preferred method for determining crystallinity is by calorimetry, by measuring the heat of dissolution of the sample in a solvent and comparing this heat with the measured heats of amorphous and crystalline standard of the same salt, provided the dissolution of the crystalline salt is substantially different than the dissolution of the corresponding amorphous salt.

As crystallinity is difficult to measure, the following exemplary compounds meet the requirements for substantially crystalline copper compounds: copper(II) borate; copper boride ($Cu_3B_2$); yellow copper(I) carbonate; basic copper carbonate; copper(II) carbonate dihydroxide ($CuCO_3 \times Cu(OH)_2$); copper(II) carbonate dihydroxide ($2CuCO_3 \times Cu(OH)_2$); copper (I and II) chloride; copper(II) chloride$\times 2H_2O$; copper oxychloride ($CuCl_2 \times Cu(OH)_2$); copper(I and II) cyanide; copper(I and II) fluoride; copper(II) formate; copper(I and II) oxide; copper phosphate$\times 3$ water; copper(I and II) sulfate; tribasic copper sulfate; and copper(I) thiocyanate. The term (I and II) means the copper(I) salt and the copper(II) salt. These salts are considered substantially crystalline with as much as 20% by weight based on the weight of the copper being substituted with magnesium, zinc, or both. The following exemplary compounds meet the requirements for substantially crystalline zinc compounds: zinc carbonate; zinc chloride; zinc cyanide; zinc diphosphate; zinc fluoride; zinc fluoride$\times 4$ water; zinc hydroxide; zinc oxide; zinc phosphate; and zinc sulfate. These salts are typically substantially crystalline with as much as 20% by weight based on the weight of the zinc being substituted with magnesium, copper, or both. The following exemplary compounds meet the requirements for substantially crystalline tin compounds: tin(II) chloride; tin(II) chloride$\times 2$ water; tin(II and IV) oxide; tin(II) diphosphate (pyrophosphate); tin(II) phosphate ($Sn_3(PO_4)_2$); and tin(II) sulfate.

In preferred embodiments, at least about 20%, 30%, 50%, or 75% of the weight of the copper-based particles may be composed of the substantially crystalline (or amorphous sparingly soluble) copper compound. The substantially crystalline (or amorphous sparingly soluble) copper compound may comprise, and in preferred embodiments does comprise, one or more cations in addition to copper, for example, magnesium and/or zinc. In another embodiment, essentially all of the weight of the copper-based particles is composed of substantially crystalline (or amorphous sparingly soluble) copper compound.

Several of the copper salts described herein are available in crystalline and in amorphous phases. Generally crystallinity is preferred, as the lattice energy of the crystal is expected to slow down dissolution. However, amorphous copper salts are useful in the invention, and for the less soluble salts the amorphous phases may be preferred over crystalline phases. Phosphate-stabilized copper hydroxide, a preferred sparingly soluble copper salt used in embodiments of this invention, is typically substantially amorphous. One embodiment of this invention is an effective, long-lasting, environmentally responsible, non-staining/coloring, inexpensive, non-corrosion-inducing, injectable, amorphous or substantially amorphous copper based, zinc-based, or tin-based particulate preservative treatment for wood and wood products that is substantially free of hazardous material. Amorphous sparingly soluble salts are equally effective, and they can be treated with one or more coatings, or can be made of a particular size, or of more insoluble salts, such that the amorphous material may easily have release and leach characteristics like the substantially crystalline salts. Substantially crystalline sparingly soluble salts should be considered a preferred variant of the invention, as the same disclosure is generally equally applicable to amorphous material, or substantially amorphous material.

Copper-Based Particulate—

As used herein, the term "copper-based particulate" means a particle having a size between about 0.7 microns and about 0.01 microns that comprises at least one substantially crystalline (or amorphous sparingly soluble) copper salt. The term "particle" is used interchangably with the term "particulate," while the term "nanoparticle" refers to particles having a size less than about 0.01 microns in diameter. The term "copper" includes, unless specifically stated otherwise, the cuprous ion, the cupric ion, or mixtures thereof, or combinations thereof. The term "copper-based" means the particle comprises at least about 20%, 30%, 50%, or 75% by weight of one or more substantially crystalline (or amorphous sparingly soluble) copper compounds. In another embodiment, essentially all (e.g., more than 95%) of the weight of the copper-based particles is composed of substantially crystalline (or amorphous sparingly soluble) copper compound.

Zinc-Based Particulate—

As used herein, the term "zinc-based particulate" means a particle having a size between about 0.5 microns and about 0.01 microns that comprises at least one substantially crystalline (or amorphous sparingly soluble) copper salt. The term "particle" is used interchangably with the term "particulate." The term "zinc-based" means the particle comprises at least about 20%, 30%, 50%, or 75% by weight of one or more substantially crystalline (or amorphous sparingly soluble) zinc compounds. In another embodiment, essentially all (e.g., more than 95%) of the weight of the zinc-based particles is composed of one or more substantially crystalline (or amorphous sparingly soluble) zinc compounds. The preferred substantially crystalline zinc-containing materials are zinc hydroxide, zinc borate ($Zn(BO_2)_2 \times H_2O$), and zinc carbonate. As for the copper-based particles and the tin-based particles, if the borate is used as the anion, preferably the composition also comprises one or more salts of carbonate or hydroxide (or hydroxide-containing) salts to maintain a slightly elevated pH within the wood matrix, to slow dissolution of the borate salts. If zinc-based particulates are used, they are advantageously used with copper-based particulates.

Tin-Based Particulate—

As used herein, the term "tin-based particulate" means a particle having a size between about 0.5 microns and about 0.01 microns that comprises at least one substantially crystalline (or amorphous sparingly soluble) tin salt. The term "particle" is used interchangably with the term "particulate." The term "tin-based" means the particle comprises at least about 20%, 30%, 50%, or 75% by weight of one or more substantially crystalline (or amorphous sparingly soluble) tin compounds. In another embodiment, essentially all (e.g., more than 95%) of the weight of the tin-based particles is composed of one or more substantially crystalline (or amorphous sparingly soluble) tin compounds. Generally, tin-based particulates are not preferred because tin does not have the desired bio-activity. Tin oxides are believed to be particularly inert, though Nanophase Technologies in February 2004 claimed, in "Nanotechnology in brief" making pilot quantities of 30 nm silver-doped nanocrystalline tin oxide for use in wood preservatives, speciality paints, polymer additives, conductive coatings, and electronic materials. The preferred substantially crystalline tin material are tin hydroxides, $Sn(OH)_2$ and $Sn(OH)_4$. If tin-based particulates are used, they are advantageously used with copper-based particulates.

It is recognized that some embodiments encompassed by this invention may not meet all of the objects or characteristics of the preferred embodiments of the invention as described above. In preferred embodiments of the invention, the injectable material will meet any and preferably most of the criteria listed above for the effective, long-lasting, environmentally responsible, non-staining/coloring, inexpensive, non-corrosion-inducing, injectable, substantially crystalline (or amorphous sparingly soluble), copper-based particulate preservative treatment for wood and wood products that is substantially free of hazardous material.

In preferred embodiments of the invention, the injectable copper-based particulates will meet any and preferably most of the criteria listed above for the effective, long-lasting, environmentally responsible, non-staining/coloring, inexpensive, less-corrosion-inducing, injectable, substantially crystalline (or amorphous sparingly soluble), copper-based particulate preservative treatment for wood and wood products that is substantially free of hazardous material.

The Substantially Crystalline Copper Composition in the Copper-Based Particulates.

The copper-based particulates can have a substantially homogenous substantially crystalline (or amorphous sparingly soluble) copper composition within each particle. Alternatively, the particles can comprise two or more separate substantially crystalline (or amorphous sparingly soluble) copper phases. Preferred particles comprise at least 30%, preferably at least 50%, more preferably at least 70%, for example between about 80% and about 98% by weight of total of copper hydroxides, copper oxides, basic copper carbonates, copper carbonates, copper oxychloride, tribasic copper sulfate, alkaline copper nitrate, copper borate, or mixtures thereof. Most comprise a basic copper salt, with the exception of copper borate and copper oxides. As a high pH suppresses the solubility of copper borate, advantageously, treatments that comprise particulates of copper borate also comprise a basic substantially crystalline (or amorphous sparingly soluble) copper-containing salts. Copper carbonate is a most preferred compound, as it is less visible than some other salts, and has excellent solubility characteristics.

In another embodiment of the invention, the various particles within a wood preservative can comprise different substantially crystalline (or amorphous sparingly soluble) copper compositions. For example, a treatment may contain particles that comprise crystalline copper borate, other particles that comprise alkaline copper carbonate, and even other particles that comprise copper oxide. The particles having different phases may in preferred embodiments be of different sizes, porosity, or morphology, depending on the crystalline copper material present.

In one embodiment, exemplary wood preservatives comprise copper-based salt particles having a size distribution in which at least 50% of particles have a diameter smaller than 0.5 μm, 0.25 μm, 0.2 μm, or 0.15 μm. A preferred particle sizing technique is a sedimentation or centrifugation technique based on Stoke's Law. An exemplary preservative of the invention comprises particles comprising a sparingly soluble copper salt, e.g., copper hydroxide, having an average particle diameter of less than about 500 nanometers, for example less than about 250 nanometers, or less than about 200 nanometers. In one embodiment, the average particle diameter is at least 25 nanometers, for example, at least 50 nanometers.

Method of Manufacture of Substantially Crystalline Copper-Containing Particles

Exemplary copper-based particles comprise one or more of copper metal, a copper oxide, a copper hydroxide, copper carbonate, and a copper salt that is sparingly soluble. Preferred wood preservatives comprise copper-based particles that comprise at least about 20%, for example, at least about 50%, 60%, 70%, or 75% by weight copper, based on the weight of the particle. An exemplary copper-based particle comprises about twice as much copper by weight as oxygen.

There are a large number of references describing how to make copper-containing "nanoparticles." These references generally can not be used to manufacture the particulates at the desired cost. The formation of 7 nanometer particles of any of CuO, $Cu_2O$, or mixed phase $CuO/Cu_2O$ is described for example in "Copper and Copper Oxide Nanoparticle Formation by Chemical Vapor Nucleation From Copper(II) Acetacetonate" was described in Journal of Nanoparticle Research, 3(5-6): 383-398, December 2001. Such particles are, or course, readily injectable into wood, and if injected they may provide a degree of biological activity. But they can not be used for the process because such particles are too expensive for use in wood treatment. R. L. Hamilton and O. K. Cosser described using 35 nm CuO or 10 nm Cu metal particles to enhance thermal conductivity of antifreeze in "Thermal Conductivity of Heterogenous Two-Component Systems", Ind. & Engr. Chem. Fund., 1, 187-191 (1962). Such particles would also be expected to be injectable into wood. United States Patent Application 20030077219 describes a method for producing copper salts from at least one cupriferous reactant and one additional reactant, where micro-emulsions are prepared from two reactants while employing at least one block polymer to obtain intermediate products with a particle size of less than 50 nm, preferably 5 to 20 nm. Material can be adjusted to specific applications through the appropriate doping of foreign ions. This application teaches wood treatment applications, stating copper compounds that have been produced pursuant to the present invention can penetrate more easily and more deeply into the wood layers under treatment due to their quasi atomic size. These improved properties can eliminate or reduce the need for pressure impregnation while ensuring prolonged protection against various organisms. Agglomerates characterized by a size of about 200 nanometers consist of a multitude of primary particles characterized by a size range of 5 to 20 nm. Example particle sizes were between 10 and 50 nm and agglomerate sizes between 100 and 300 nm. During the immersion of equivalent wood into the copper hydroxide micro-emulsion prepared pursuant to the invention, the copper hydroxide was not limited to the surface, but instead penetrated to a depth of more than 10 to 298 mm. The use of solvents makes such processes generally too expensive for use in wood preservatives, though this process can be useful provided the solvent serves a subsequent purpose of solvating one or more organic biocides, to partially bind the organic biocides to the particulate by partially or completely removing the solvent by evaporation. Modifying the process of this application to make particulates greater than 50 nanometers in diameter, for example between about 100 and about 200 nanometers in diameter, can be useful provided the solvent serves a subsequent purpose of solvating one or more organic biocides, to partially bind the organic biocides to the particulate by partially or completely removing the solvent by evaporation.

The method of U.S. Pat. No. 6,596,246 which requires rigorous removal of iron to make a copper hydroxide can be utilized. Such a process increases the cost of the product, however.

In one embodiment of the invention, copper-based particles are prepared, such as by precipitation, from a mixture comprising copper and an amine. The copper and amine may be present in the form of a copper-amine complex. The mixture may comprise at least one of copper monoethanolamine, copper diethanolamine, copper-ammonia, and/or copper ethylenediamine. The copper-amine complex is usually in an aqueous solution. Preferred precipitates comprise copper hydroxides. The particles may be prepared by modifying a pH of the mixture comprising copper and the amine. For example, the pH of a mixture comprising copper and an amine may be reduced to value sufficient to precipitate copper-based particles. In any event, the mixture comprising copper and the amine may be diluted with water to have a copper concentration of at least about 0.25, for example, at least about 0.5, such as at least about 1% by weight. The copper concentration may be less than about 2%, for example, less than about 1.5%. The pH of the mixture comprising copper and the amine, such as the diluted mixture, may be reduced using acid to prepare a precipitate comprising copper-based particles. The particles may comprise copper hydroxide. A dispersant may be added to the mixture, such as before obtaining the precipitate, upon obtaining the precipitate, or thereafter. A stable aqueous copper-amine complex solution may have a pH of 8 to 13. One method for preparing the precipitate comprises adjusting the pH of an aqueous mixture of the copper-amine complexes. In one embodiment, the pH is adjusted so that the pH is at least about 4, for example, at least about 5.5. The pH of the mixture may be adjusted to less than about 8, for example, to less than about 7.5, such as less than about 7. The pH may be adjusted to about 7. The pH is adjusted by adding an acid to the mixture. Alternatively, the pH may be adjusted by adding the mixture to acid. The solution of copper-amine complex may be prepared in the presence of acid. Suitable acids for adjusting the pH include, for example, sulfuric acid, nitric acid, hydrochloric acid, formic acid, boric acid, acetic acid, carbonic acid, sulfamic acid, phosphoric acid, phosphorous acid, and/or propionic acid. The anion of the acid used may be partially incorporated in the precipitated salt.

One embodiment of a method for preparing copper-based particles comprises precipitation of copper-based particles from a solution comprising (a) copper, such as in the form of a copper salt, and (b) a pH modifying agent, such as a hydroxide. Exemplary hydroxides may be selected from hydroxides of group 1a and/or group 2a elements, such as sodium and potassium hydroxide.

Copper salts useful in preparing copper-based particles of the invention preferably comprise water soluble salts of copper and another material. An exemplary copper salt may include at least one of a copper sulfate, a halogen-containing copper salt, such as copper chloride or copper bromide, a copper nitrate, a copper acetate, a copper formate, and a copper propionate. The one or more copper salts may be provided in the form of a solution, such as an aqueous solution, of a liquid and the copper salt.

U.S. Pat. No. 4,808,406, the disclosure of which is incorporated by reference, describes a useful method for producing finely divided stable cupric hydroxide compositions of low bulk density comprising contacting solutions of an alkali metal carbonate or bicarbonate and a copper salt, precipitating a basic copper carbonate-basic copper sulfate to a minimum pH in the range of greater than 5 to about 6, contacting the precipitate with an alkali metal hydroxide and converting basic copper sulfate to cupric hydroxide. Another method of manufacturing the copper compounds is the method described in U.S. Pat. No. 4,404,169, the disclosure of which is incorporated by reference. This patent describes a process of producing cupric hydroxides having stability in storage if phosphate ions are added to a suspension of copper oxychloride in an aqueous phase. The copper oxychloride is then reacted with alkali metal hydroxide or alkaline earth metal hydroxide, and the cupric hydroxide precipitated as a result of the suspension is washed and then re-suspended and subsequently stabilized by the addition of acid phosphate to adjust a pH value of 7.5 to 9. The suspended copper oxychloride is preferably reacted in the presence of phosphate ions in an amount of 1 to 4 grams per liter of the suspension and at a temperature of 20° to 25° C. and the resulting cupric hydroxide is stabilized with phosphate ions.

There are numerous methods of preparing very small particles of copper salts, and the above list is exemplary and not complete. The simplest and by far the least expensive method of producing small particles is a standard precipitation of admixing two solutions, one containing soluble copper and one containing the desired anion, and some particles resulting from slightly modified precipitation processes are of a size that may be injected into the wood. The most useful modification is simply adding small quantities of anion to a concentrated solution of the cation, or vice versa, with vigorous stirring. Examples in the prior art show an average particle size as low as 0.3 microns was obtainable. Such processes are also desirable because the cost of counter-ions (those ions that form the salts that are admixed, but that are not incorporated into the substantially crystalline (or amorphous sparingly soluble) copper material) is negligible. Standard materials such as chlorides, sulfates, ammonia, and the like are common counterions. Further, the material need not be ultra-pure. Indeed, it is desirable to have one or more "contaminants" in the precipitating solutions. Smaller diameters are obtained when the concentration of impurities such as Mg, Ca, Zn, Na, Al and Fe in the suspension is high. Fe present in the suspension acts especially strongly to prevent formation of large-diameter cuprous hydroxide particles. Fe concentration is preferably greater than 70 ppm to obtain smaller particles.

In one embodiment, copper and a hydroxide are combined to prepare a precipitate comprising copper. The copper and hydroxide may be combined with the copper in the form of a copper salt. For example, a solution comprising at least one copper salt and a solution comprising at least one hydroxide may be combined to precipitate copper-based particles. In one embodiment, the method includes precipitating copper-based particles from a solution comprising at least one other metal, such as a salt of at least one other metal. For example, copper-based particles of the invention may be precipitated from a solution comprising at least one of one or more group 2a metals such as magnesium or salts thereof. The metal or salt of the metal may be zinc. In one embodiment, (a) a solution comprising a copper salt and at least one other metal, which may be in the form of one or more salts, and (b) a solution comprising a hydroxide are combined in amounts sufficient to precipitate copper-based particles, such as particles comprising copper hydroxide.

In one embodiment, particles are prepared by adding a copper salt solution to a hydroxide solution comprising about 20% hydroxide by weight. The copper salt solution is added until a desired amount of copper-based particles are obtained. For example, the copper salt solution may be added until the pH of the hydroxide solution falls to at least about 11.5, 11, 10.5, or about 10. The precipitate comprising the precipitated copper-based particles may be used directly to protect wood or wood products, but are beneficially milled to reduce the fraction of particulates having a diameter above 1 micron.

Copper hydroxide is not particularly stable. Hydroxides can be changed to oxides by for example, a quick and exothermic reaction by exposure of the copper hydroxide particles to aqueous solution of glucose. Copper hydroxide may react with air, sugars, or other compounds to partially or completely form copper oxide. While this is generally of less concern with foliar fungicides, the conditions for conversion are highly favored during kiln-drying treated wood, which contains gluconuronic acids, which are sugar-like molecules, and heat and a dehydrating condition, create a high probability of such transformation occurring within the wood.

However, as taught by U.S. Pat. No. 3,231,464, the disclosure of which is incorporated herein by reference thereto, the presence of magnesium or magnesium and zinc can help stabilize cupric hydroxide from converting to copper oxide via the loss of a water molecule. The preferred copper hydroxide particles used in this invention are stabilized. U.S. Pat. No. 3,231,464 teaches stabilizing the copper hydroxide with added magnesium zinc, or both, at a Cu:Mg and/or Cu:Zn weight ratio of 8:1. Copper hydroxide prepared in a manner so as to contain significant magnesium and/or zinc hydroxides are more stable and resistant to degradation to copper oxides. The preferred copper hydroxide particle's comprise between 50% and 90% copper hydroxide, with the remainder comprising zinc hydroxide, magnesium hydroxide, or both. The process described in U.S. Pat. No. 3,231,464 is inexpensive, and with modifications produces particulates with a particle size distribution with a median particle size of a few tenths of a micron.

While such methods can provide small particles of selected substantially crystalline (or amorphous sparingly soluble) salts, these processes usually have a small fraction of particles that are unacceptably large. Generally, however, a few particles from a normal precipitation process are too big to be injectable. A very small fraction of particles having a particle size above about 1 micron causes, in injection tests on wood specimens, severely impaired injectability. Large particles, e.g., greater than about 1 micron in diameter, should be removed. Removal via filtering is not effective, as a large fraction of injectable particles will be caught on filters designed to remove the bigger particles. We have surprisingly found that milling, for example wet-milling, can advantageously modify particle size and morphology. Particles can be smoothed and large particles removed by continuous-process centrifuging. Alternately, as described above, we have surprisingly found that substantially crystalline (or amorphous sparingly soluble) copper-based particulates that are manufactured by a precipitation process, using conditions known in the art to produce small particles, can be readily milled into an injectable material by wet milling with a milling material such as 0.5 mm diameter zirconium silicate in a matter of minutes.

In another embodiment, the copper-based particulates can have a substantial amount, e.g., at least 0.5% by weight, for example at least 2% by weight, but less than 50% by weight based on the weight of copper of one or more other cations, either dispersed within the substantially crystalline (or amorphous sparingly soluble) copper composition or substantially as a separate phase within the particulate. In a preferred embodiment, the copper-based particulates can have a substantial amount of one or more of magnesium, zinc, or both, wherein these cations are either dispersed within the substantially crystalline (or amorphous sparingly soluble) copper composition or be a separate phase within a particulate. The weight ratio of copper to zinc may range between 99.9:0.1 to 1:1, but is preferably between 99.5:0.5 to 90:10, for example between 99:1 and 94:6. The weight ratio of copper to magnesium may range between 99.9:0.1 to 1:1, but is preferably between 99.5:0.5 to 85:15, for example between 95:5 and 90:10.

In one embodiment of the invention, copper-based particles are precipitated from a mixture of a copper salt solution and a hydroxide (and optionally other anions) in the presence of at least one group 2a metal or salt thereof, such as magnesium or a magnesium salt. In one embodiment, the copper-based particles are precipitated from a mixture comprising at least about 0.05 parts magnesium, for example at least about 0.1 parts magnesium per 9 parts copper. The mixture may comprise at least about 0.25 parts magnesium per 9 parts copper. The mixture may comprise less than about 1.5 parts magnesium, for example, less than about 1.0 parts, or less than about 0.75 parts magnesium per 9 parts copper.

Copper-based particles prepared in accordance with the present invention will comprise a group 2a metal or zinc if such materials (metal ions) were used in preparation of the particles. In another embodiment, the copper-based particles are precipitated from a mixture comprising at least about 0.2 parts magnesium, for example, at least about 0.25 parts magnesium per 22.5 parts copper. The mixture may comprise at least about 0.5 parts magnesium per 22.5 parts copper. The mixture may comprise less than about 3.5 parts magnesium, for example, less than about 2.5 parts magnesium, or less than about 2 parts magnesium per 22.5 parts copper. The parts here merely reflect weight ratios of the cations in the solution to be precipitated, and the parts do not imply concentration.

Alternatively, or in combination with the group 2a metal or salt thereof, the copper-based particles may be precipitated from a solution comprising zinc metal or salt thereof. For example, the mixture may comprise at least about 0.1 parts zinc, for example, at least about 0.25 parts zinc, at least about 1.0 parts zinc, or at least about 2.0 parts zinc per 22.5 parts copper. The mixture may comprise less than about 3.0 parts zinc, for example, less than about 2.5 parts zinc, or less than about 1.5 parts zinc per 22.5 parts copper. Preferably, the mixture additionally comprises at least about 0.25 parts magnesium, for example, at least about 0.5 parts magnesium, at least about 1.0 parts magnesium, or at least about 2 parts magnesium per 22.5 parts copper. The mixture may comprise less than about 5.0 parts magnesium, for example, less than about 2.5 parts magnesium, or less than about 2 parts magnesium per 22.5 parts copper. Table I sets forth exemplary ratios of zinc, magnesium, and copper in accordance with the present invention.

TABLE I

Exemplary Formulations To Precipitate
Mg/Zn-Stabilized Copper Hydroxide

| Formulation | Parts Zinc | Parts Magnesium | Parts Copper |
| --- | --- | --- | --- |
| 1 | 0.5 | 0.5 | 22.5 |
| 2 | 0.75 | 0.75 | 22.5 |
| 3 | 1.5 | 1.5 | 22.5 |
| 4 | 2.5 | 1.0 | 22.5 |
| 5 | 2.5 | 2.5 | 22.5 |

Such mixtures can be used to precipitate copper hydroxides, basic copper carbonate, copper oxychloride, copper borate, and any of the substantially crystalline (or amorphous sparingly soluble) salts described herein.

In alternative embodiments, the particulates can comprise particles that contain a substantially crystalline (or amorphous sparingly soluble) copper composition with between 0.001% and 3%, preferably 0.005% to 0.5%, for example 0.01% to 0.1% by weight of silver, based on the weight of copper, and also optionally the other cations. Silver is expensive but is efficacious against some bio-organisms in very small amounts, and therefore silver is a useful co-cation in a substantially crystalline (or amorphous sparingly soluble) copper-based particulate. A wood treatment containing 0.25 pounds copper per cubic foot would comprise, at a 0.04% silver loading relative to copper, less than 0.2 ounces of silver per one hundred cubic feet of wood. Generally, if silver is incorporated into the substantially crystalline (or amorphous sparingly soluble) copper phase, the substantially crystalline (or amorphous sparingly soluble) copper phase is preferably a copper(I) salt and the silver ions are disposed homogenously through the substantially crystalline (or amorphous sparingly soluble) copper phase, to prevent the minute quantities of silver from being prematurely leached from the wood.

Yet another embodiment of the invention is an effective, long-lasting, environmentally responsible, non-staining/coloring, inexpensive, non-corrosion-inducing, injectable, substantially crystalline (or amorphous sparingly soluble), zinc-based particulate preservative treatment for wood and wood products that is substantially free of hazardous material. This composition can be used independently of the copper-based particulates, but in preferred embodiments is used in combination with one or more copper-based particulates. Modification of the above processes to produce substantially crystalline (or amorphous sparingly soluble) zinc-containing particulates is within the ability of one of ordinary skill in the art, and such modifications will not be described here.

Similarly, modifications of the above processes to produce substantially crystalline (or amorphous sparingly soluble) zinc-containing particulates are within the ability of one of ordinary skill in the art, and such modifications will not be described here.

Milling—

Generally, the simple, inexpensive copper salt precipitation processes provide particles with a size too great for injection. Even for processes that provide very small median diameter particles, such as, a few tenths of a micron in diameter, the precipitation process seems to result in a small fraction of particles that are larger than about 1 micron, and these particles plug up pores and prevent acceptable injectability. The size distribution of the injectable particles must have the vast majority of particles, for example at least 95% by weight, preferably at least 99% by weight, more preferably at least 99.5% by weight, be of an average diameter less than about 1 micron, and advantageously the particles are not rod-shaped with a single long dimension. Average particle diameter is beneficially determined by Stokes Law to a size down to about 0.2 microns. Smaller sizes are beneficially determined by, for example, a dynamic light scattering method or laser scattering method or electron microscopy. Generally, such a particle size and particle size distribution can be achieved by mechanical attrition of particles.

Attrition can be obtained for example 1) by use of a pressure homogenizer such as that manufactured by SMT Ltd. having 400 kg/cm$^2$ of pressure at a flow rate of 1 l/min., though such a system often requires the slurry be processed overnight; by processing in an ultrasonic homogenizer such as is manufactured by Nissei Ltd., though such a method is energy intensive; by wet milling in a sand grinder charged with for example partially stabilized zirconia beads with diameter 0.5 mm; alternately wet milling in a rotary sand grinder with partially stabilized zirconia beads with diameter 0.5 mm and with stirring at for example 1000 rpm; or by use of a wet-ball mill, an attritor (e.g., manufactured by Mitsui Mining Ltd.), a perl mill (e.g., manufactured by Ashizawa Ltd.), or the like. Attrition can be achieved to a lesser degree by centrifugation, but larger particles can be simply removed from the composition via centrifugation. Removing the larger particulates from a composition can provide an injectable formulation. Said particulates can be removed by centrifugation, where settling velocity substantially follows Stokes law. While this process provides injectable slurries, a fraction of the copper-containing particulates that are separated thereby include both large particles as well as a portion of the injectable particles, and generally this material would be recycled by being dissolved and precipitated. Such a process adds an additional cost to forming the injectable copper-containing particulate wood treatment.

The most effective method of modifying the particle size distribution is wet milling. Beneficially all injectable formulations for wood treatment should be wet-milled, even when the "mean particle size" is well within the range considered to be "injectable" into wood. Traditional precipitation techniques are known to produce particles with a median particle size between about 0.2 and 6 microns, depending on the salts used as well as on various reaction conditions. For example, a commercially available copper-based particulate product, a magnesium stabilized form of copper hydroxide (available from Phibro-Tech., Inc.) has a mean particle size of about 200 nm. However, when this material was slurried and injected into wood, there was unacceptable plugging on the face of the wood. Careful examination found the precipitation process used by Phibro-Tech., Inc. resulted in a few weight percent of particles with a size over 1 micron, and this small amount of material was hypothesized to form the start of the plug (where smaller, normally injectable particles were subsequently caught by the plug). Wet milling with 2 mm zirconium silicate media had no effect—wet milling for days resulted in only a marginal decrease in particle size, and the material was still not injectable in commercial quantities.

However, we surprisingly found that a milling process using 0.5 mm high density zirconium silicate grinding media provides further efficient attrition, especially for the removal of particles greater than about 1 micron in the commercially available copper-based particulate product available from Phibro-Tech., Inc. The milling process usually takes on the order of minutes to achieve almost complete removal of particles greater than 1 micron in size. This wet milling process is inexpensive, and all of the precipitate can be used in the injectable copper containing particulate wood treatment. The selection of the milling agents is not critical, and can be zirconia, partially stabilized zirconia, zirconium silicate, and yttrium/zirconium oxide, for example, recognizing that the more dense materials give faster particle size attrition. The size of the milling material is believed to be important, even critical, to obtaining a commercially acceptable process. The milling agent material having a diameter of 2 mm or greater are ineffective, while milling agent material having a diameter of 0.5 mm is effective typically after 15 minutes of milling. We believe the milling agent is advantageously of a diameter less than 1.5 mm, preferably is less than 1 mm in diameter, for example between about 0.1 mm and about 1 mm, or alternately between about 0.3 mm and 0.7 mm.

The original focus on injectability focused on the magnesium stabilized copper hydroxide product available from Phibro-Tech., Inc., as this material started (and ended) with a material that had a median diameter of 0.2 microns. While we originally believed that the milling broke aggregates, possibly fused aggregates, of smaller particles that formed the "greater than about 1 micron fraction" of the above-described product, the milling process was surprisingly equally effective on larger mean diameter particles.

We have surprisingly found that copper-based particulates that are manufactured by a straightforward precipitation process, using conditions known in the art to produce small particles, e.g., particles having a size less than 10 microns, can be readily milled into an injectable material. Therefore, milling other precipitate material with 0.5 mm diameter zirconium silicate (or any comparable product, e.g., a 0.1 mm to 1 mm sized zirconium silicate or zirconium oxide) can mill in a matter of minutes a substantially crystalline (or amorphous sparingly soluble) powder material having a larger initial average size into a product that can be readily injected into wood. Milling with 0.5 mm zirconium silicate media not only quickly reduced further the magnesium stabilized copper hydroxide product, but this grinding medium was also found to be effective on other forms of basic copper compounds such as other stabilized copper hydroxides, copper carbonate, tribasic copper sulfate, copper oxychloride, and copper oxides. The results of milling of a variety of materials with the 0.5 mm milling material described above for 15 minutes are shown in Table 2. Copper hydroxide material with an initial median size of 2.5 microns was quickly milled to an injectable material having a median particle size of 0.3 microns. Additional milling time would doubtless further reduce the median and average particle size. A copper carbonate material having a median size of 3.4 microns was milled to a material having a median size of less than 0.2 microns. FIG. 1 shows the face of wood injected with unmilled product and the face of wood injected with the milled product. In the color photographs the plugging is especially visible. A tribasic copper sulfate material having a median size of 6.2 microns was milled to a material having a median size of less than 0.2 microns. A copper oxychloride material having a median size of 3.3 microns was milled to a material having a median size of 0.4 microns.

sition or be a separate phase within a particulate. Generally, magnesium and zinc co-cations can help stabilize copper hydroxide and prevent its natural transition to copper oxide. We believe if substantial amounts of zinc and especially magnesium are included in the crystalline copper oxide material, it will partially disrupt the crystal and therefore encourage solubility. Copper oxides are less preferred than other substantially crystalline (or amorphous sparingly soluble) copper compounds, because the rate of dissolution is so slow. If the crystalline copper in the particles is more than 60% copper oxide, then preferably the particles have a maximum size of about 50 nanometers, or have a BET surface area of at least 300 m2/gm, or both. The particulates may need special treatments and/or properties to provide a bio-active copper concentration, and are more easily flushed from the wood.

In any of the below-described embodiments, the substantially crystalline (or amorphous sparingly soluble) copper composition in copper-based particulates and/or copper-

TABLE 2

Average Particle size (from Stokes Law Settling) Before and After Milling With 0.5 mm Zirconium Silicate

| Description | | Median PS (microns) | Particle Size Distribution Data | | | | Ref: |
|---|---|---|---|---|---|---|---|
| | | | % <10 um | % <1 um | % <0.4 um | % <0.2 um | |
| Copper Hydroxide, Dettwiler | After Treat | <0.2 | 99.0 | 96.7 | 94.6 | 84.9 | V.216.69 |
| Copper Hydroxide, Dettwiler | Before | <0.2 | 99.7 | 84.0 | 63.9 | 57.1 | V.216.69 |
| Copper Hydroxide, Furness | After Treat | 0.30 | 99.7 | 95.4 | 21.7 | — | V.216.74 |
| Copper Hydroxide, Furness | Before | 2.5 | 99.6 | 8.7 | — | — | V.216.74 |
| Copper Carbonate | After Treat | <0.2 | 99.1 | 97.2 | 96.9 | 87.3 | V.216.77 |
| Copper Carbonate | Before | 3.4 | 98.0 | 1.2 | — | — | V.216.77 |
| Tribasic Copper Sulfate | After Treat | <0.2 | 99.5 | 96.4 | 90.5 | 55.1 | V.216.85 |
| Tribasic Copper Sulfate | Before | 6.2 | 69.5 | 16.5 | — | — | V.216.85 |
| Copper Oxychloride | After Treat | 0.38 | 99.4 | 93.9 | 63.2 | — | V.218.7 |
| Copper Oxychloride | Before | 3.3 | 98.5 | 2.8 | — | — | V.218.7 |

Milling is believed to break up larger particles. It would also break particles having one large dimension, e.g., rod-like particles, which are know to have injection problems. Milling can be combined with, for example, centrifugation to create a more uniform product. Alternatively, milling can be combined with a coating process to form a more stable material.

Specific substantially crystalline (or amorphous sparingly soluble) copper-containing materials and other copper-containing materials useful in embodiments of this invention will be described below. In each instance, the zinc analog is useful for zinc-based particulates. Generally, the tin analogs can also be useful for tin-based particulates.

Copper Oxides—

In one embodiment, the substantially crystalline copper composition in a plurality of copper-based particulates can comprise one or more copper oxides. Of the copper oxides, $Cu_2O$ is preferred over CuO, as the $Cu_2O$ is subject to oxidation by oxygen dissolved in water which appears to increase the kinetics of dissolution. If the copper-based particulate material consists essentially of one or more copper oxides, however, the material will not be sufficiently bioactive. In one variant, the copper oxide material can have a substantial amount of one or more of magnesium, zinc, or both, wherein these cations are either dispersed within the substantially crystalline (or amorphous sparingly soluble) copper compobased particulate material can further comprise one or more copper oxides. Of the copper oxides, CuO is preferred over $Cu_2O$.

Copper Hydroxides—

In a preferred embodiment the substantially crystalline (or amorphous sparingly soluble) copper composition in a plurality of copper-based particulates can comprise or consist essentially of copper hydroxides. In a variant of this, the copper-based particulate material can comprise or consist essentially of copper hydroxides. Of the copper hydroxides, copper hydroxide including CuOH (usually not stable) and/or $Cu(OH)_2$ can be used, though $Cu(OH)_2$ is preferred over CuOH. In a preferred embodiment of any of the above, the substantially crystalline (or amorphous sparingly soluble) copper composition can have a substantial amount of one or more of magnesium, zinc, or both, wherein these cations are either dispersed within the substantially crystalline (or amorphous sparingly soluble) copper composition or be a separate phase within a particulate.

Basic Copper Carbonate—

In another preferred embodiment the substantially crystalline copper composition in a plurality of copper-based particulates can comprise or consist essentially of alkaline (or "basic") copper carbonates. While various compositions comprising copper hydroxide and copper carbonate are envisioned, typically alkaline copper carbonate is $[CuCO_3 \times Cu(OH)_2]$. In a variant of this, the copper-based particulate material can comprise or consist essentially of alkaline copper carbonate. In a preferred embodiment of any of the above, the substantially crystalline (or amorphous sparingly soluble) copper composition can have a substantial amount of one or more of magnesium, zinc, or both, wherein these cations are either dispersed within the substantially crystalline (or amorphous sparingly soluble) copper composition or be a separate phase within a particulate.

Copper Carbonate—

In another embodiment the substantially crystalline copper composition in a plurality of copper-based particulates can comprise or consist essentially of copper carbonate, e.g., $CuCO_3$. In a variant of this, the copper-based particulate material can comprise or consist essentially of alkaline copper carbonate. In a preferred embodiment of any of the above, the substantially crystalline (or amorphous sparingly soluble) copper composition can have a substantial amount of one or more of magnesium, zinc, or both, wherein these cations are either dispersed within the substantially crystalline (or amorphous sparingly soluble) copper composition or be a separate phase within a particulate. Copper carbonate is less preferred than basic copper carbonate, as the OH groups in the latter help keep the pH elevated, thereby reducing copper mobility.

Tribasic Copper Sulfates—

In another preferred embodiment the substantially crystalline copper composition in a plurality of copper-based particulates can comprise or consist essentially of basic copper sulfates. In a variant of this, the copper-based particulate material can comprise or consist essentially of basic copper sulfates. While various compositions comprising copper hydroxide and copper sulfate are envisioned, typically alkaline copper sulfate is $[CuSO_4 \times 3Cu(OH)_2]$. If tribasic copper sulfate is used, the substantially crystalline (or amorphous sparingly soluble) copper composition can additionally advantageously have a substantial amount of one or more of magnesium, zinc, or both, wherein these cations are either dispersed within the substantially crystalline (or amorphous sparingly soluble) copper composition or be a separate phase within a particulate.

Alkaline Copper Nitrates—

In another embodiment the substantially crystalline copper composition in a plurality of copper-based particulates can comprise or consist essentially of alkaline copper nitrates. In a variant of this, the copper-based particulate material can comprise or consist essentially of alkaline copper nitrates. While various compositions comprising copper hydroxide and copper nitrate are envisioned, typically alkaline copper nitrate is $[Cu(NO_3) \times 3Cu(OH)_2]$. If alkaline copper nitrate is used, the substantially crystalline (or amorphous sparingly soluble) copper composition can additionally advantageously have a substantial amount of one or more of magnesium, zinc, or both, wherein these cations are either dispersed within the substantially crystalline (or amorphous sparingly soluble) copper composition or be a separate phase within a particulate. In the most preferred embodiments of this invention, the wood preservative is substantially free of copper nitrates, as the nitrogen, may during the degradation process, eventually act as foodstuff for one or more bio-organisms.

Copper Oxychlorides—

In another preferred embodiment the substantially crystalline copper composition in a plurality of copper-based particulates can comprise or consist essentially of copper oxychlorides. In a variant of this, the copper-based particulate material can comprise or consist essentially of copper oxychlorides. While various compositions comprising copper hydroxide and copper chloride are envisioned, typically copper oxychloride is $[CuCl_2 \times 3Cu(OH_3)]$. In a preferred embodiment of any of the above, the substantially crystalline (or amorphous sparingly soluble) copper composition can have a substantial amount of one or more of magnesium, zinc, or both, wherein these cations are either dispersed within the substantially crystalline (or amorphous sparingly soluble) copper composition or be a separate phase within a particulate.

Copper Borate—

In another preferred embodiment the substantially crystalline copper composition in a plurality of copper-based particulates can comprise or consist essentially of copper borate. Copper borate includes basic copper borate. In a variant of this, substantially crystalline (or amorphous sparingly soluble) copper composition can have a substantial amount of one or more of magnesium, zinc, or both, wherein these cations are either dispersed within the substantially crystalline (or amorphous sparingly soluble) copper composition or be a separate phase within a particulate. Generally, the copper borate is advantageously included in a composition that also comprises copper hydroxide or one or more of the basic copper anion salts, to help moderate pH and reduce solubility of the copper borate.

Copper Ferricyanate—

In any of the above-described embodiments, the substantially crystalline (or amorphous sparingly soluble) copper composition in copper-based particulates and/or copper-based particulate material can further comprise copper ferricyanate. This embodiment includes less preferably copper ferricyanide. Alternatively, the substantially crystalline (or amorphous sparingly soluble) copper composition in the copper-based particulates can comprise or consist essentially of copper ferricyanate, $Cu_2[Fe(CN)_6]$. In another embodiment, the copper-based particulate material can comprise or consist essentially of copper ferricyanate.

Copper Fluorosilicate—

The substantially crystalline (or amorphous sparingly soluble) copper composition in copper-based particulates and/or copper-based particulate material can comprise copper fluorosilicate. Alternatively, the substantially crystalline (or amorphous sparingly soluble) copper composition in the copper-based particulates can comprise or consist essentially of copper fluorosilicate. In another embodiment, the copper-based particulate material can comprise or consist essentially of copper fluorosilicate.

Copper Thiocyanate—

In any of the above-described embodiments, the substantially crystalline copper composition in copper-based particulates and/or copper-based particulate material can further comprise copper thiocyanate, though it is generally difficult to manufacture crystalline copper thiocyanate. Alternatively, the copper composition in the copper-based particulates can comprise or consist essentially of CuSCN. In another embodiment, the copper based particulate material can comprise or consist essentially of CuSCN.

Copper Diphosphate or Copper Pyrophosphate—

In any of the above-described embodiments, the substantially crystalline copper composition in copper-based particulates and/or copper-based particulate material can further comprise copper pyrophosphate, $Cu_2P_2O_7$. Alternatively, the substantially crystalline (or amorphous sparingly soluble) copper composite on in the copper-based particulates can comprise or consist essentially of copper pyrophosphate. In another embodiment, the copper-based particulate material can comprise or consist essentially of copper pyrophosphate.

Copper Cyanate and/or Copper Cyanate—

Copper cyanide, $Cu(CN)_2$, and copper cyanate, $Cu(CNO)$, are each a sparingly soluble copper salt, but they are too dangerous to be useful for copper-based wood preservative treatments. When even a small quantity of copper cyanate and/or copper cyanide is used, the formulation must be basic, that is, contained in an alkaline formulation.

The copper-based particulates can comprise or consist essentially of any of the above listed sparingly soluble copper compounds. In another preferred embodiment the substantially crystalline (or amorphous sparingly soluble) copper composition in the copper-based particulates in a wood preservative formulation can comprise or consist essentially of a plurality of sparingly soluble substantially crystalline (or amorphous sparingly soluble) copper salts selected from copper oxide, copper hydroxides; copper carbonates, alkaline (or "basic") copper carbonates; alkaline copper sulfates; alkaline copper nitrates; copper oxychlorides; copper borates, and mixtures thereof, with the proviso that at least one of the substantially crystalline (or amorphous sparingly soluble) copper salts is not a copper oxide. In a variant of this, the copper-based particulate material can comprise or consist essentially of one or more sparingly soluble substantially crystalline copper salts selected from copper hydroxides; copper carbonates, alkaline (or "basic") copper carbonates; alkaline copper nitrates; alkaline copper sulfates; copper oxychlorides; copper borates, and mixtures thereof. In any of the above, the substantially crystalline (or amorphous sparingly soluble) copper composition can have a substantial amount of one or more of magnesium, zinc, or both, wherein these cations are either dispersed within the substantially crystalline (or amorphous sparingly soluble) copper composition or be a separate phase within a particulate.

In preferred embodiments of the invention, at least some particulates comprise copper hydroxide, basic copper carbonate, or both. In more preferred embodiments, the copper hydroxide comprises between 6 and 20 parts of magnesium per 100 parts of copper, for example between 9 and 15 parts of magnesium per 100 parts of copper. Alternatively, in another more preferred embodiments, the copper hydroxide comprises between 6 and 20 parts total of magnesium and zinc per 100 parts of copper, for example between 9 and 15 parts total of magnesium and zinc per 100 parts of copper. In some embodiments, the basic copper carbonate comprises between 6 and 20 parts of magnesium per 100 parts of copper, for example between 9 and 15 parts of magnesium per 100 parts of copper, or alternatively between 6 and 20 parts total of magnesium and zinc per 100 parts of copper, for example between 9 and 15 parts total of magnesium and zinc per 100 parts of copper. Alternatively or additionally, in a preferred embodiment, the copper hydroxide and/or basic copper carbonate comprises between about 0.01 and about 5 parts of phosphate per 100 parts of copper, for example between 9 and 15 parts of phosphate per 100 parts of copper.

In another preferred embodiment, slurry comprises a sparingly soluble copper salt particulates and also comprises zinc borate particulates. Preferably at least some of the sparingly soluble copper salt-based particulates comprise copper borate. It is known to use a two stage process where a zinc or copper salt is injected into the wood followed by a second step wherein the borax is injected and the insoluble metal borate is formed in situ. Such a complicated, time consuming, and therefore expensive process is not sufficiently cost-effective. As the solubility of copper borate is very pH sensitive, in a preferred embodiment the sparingly soluble copper salts comprise an alkaline material, e.g., copper hydroxide or copper carbonate, to reduce the solubility of the copper borate.

Soluble Substantially Crystalline Copper Salts—

In any of the above-described embodiments, the substantially crystalline copper composition in copper-based particulates and/or copper-based particulate material can further comprise one or more soluble substantially crystalline copper salts, for example copper sulfate, copper fluoroborate; copper fluoride, or mixtures thereof, where the soluble substantially crystalline copper salts phase is stabilized against dissolution. Alternatively, the substantially crystalline copper composition in the copper based particulates can comprise or consist essentially of one or more soluble substantially crystalline copper salts, for example, copper fluoroborate; copper sulfate, copper fluoride, or mixtures thereof, where the soluble substantially crystalline copper salts phase is stabilized against dissolution. Such protection may be provided by encasing the soluble copper salts in a shell or a matrix of sparingly soluble copper salts or in insoluble copper salts, such as copper phosphate.

In another embodiment, the copper-based particles may be essentially free of halogen, which means that the weight percent of halogen in the particles is less than about 2.5%. Preferably, the weight percent of halogen in copper-based particles that are essentially free of halogen is less than about 1%. The copper-based particles may be free of halogen.

Copper Phosphate—

In any of the above-described embodiments, the substantially crystalline copper composition in copper-based particulates and/or copper-based particulate material can further comprise the substantially insoluble copper salt copper phosphate, $Co_3(PO_4)_2$. Alternatively, the substantially crystalline (or amorphous sparingly soluble) copper composition in the copper-based particulates can comprise or consist essentially of $Cu_3(PO_4)_2$. Generally, in preferred embodiments, if $Cu_3(PO_4)_2$ is present it is a coating over other sparingly soluble copper salts, wherein the $Cu_3(PO_4)_2$ provides a fairly inert coating for a period of time before it dissolves or partially dissolves. If there are copper-based-particulates substantially comprising $Cu_3(PO_4)_2$ and/or copper oxide, the particulates should be exceedingly small, e.g., less than about 0.05 microns, preferably less than about 0.04 microns, to provide maximum surface area to help dissolution of the particles, and the wood treatment should contain another type of substantially crystalline (or amorphous sparingly soluble) copper-based particulates, e.g., basic copper carbonate, copper borate, tribasic copper sulfate, copper hydroxides, and the like.

Copper 8-Quinolinolate—

In any of the above-described embodiments, the copper composition in copper-based particulates and/or copper-based particulate material can further comprise the insoluble copper salt copper 8-quinolinolate. Alternatively, the copper composition in the copper-based particulates can comprise or consist essentially of copper 8-quinolinolate. Generally, in preferred embodiments, if copper 8-quinolinolate is present it is a coating over other sparingly soluble copper salts, wherein the copper 8-quinolinolate provides a fairly inert coating for a period of time before it dissolves or partially dissolves. If there are copper-based particulates substantially comprising copper 8-quinolinolate, the particulates should be exceedingly small, e.g., less than about 0.01 microns, preferably less than about 0.005 microns, to provide maximum surface area to help dissolution of the particles.

In any of the above-described embodiments, the composition can further comprise copper quinaldate, copper oxime, or both in particulate form.

In one embodiment, the copper-based particles comprise a substantially crystalline copper compound. At least about 20%, 30%, 50%, or 75% of the weight of the copper-based particles may be composed of the substantially crystalline copper compound. In another embodiment, essentially all (e.g., more than 90%, for example more than 95%) of the weight of the copper-based particles is composed of substantially crystalline copper compound. In preferred embodiments the particle comprises at least about 20%, preferably at least about 30%, and more preferably at least about 50%, for example at least about 75% by weight of one or more sparingly soluble copper salts. In another embodiment, essentially all (e.g., more than 90%, for example more than 95%) of the weight of the copper-based particles is composed of substantially crystalline copper compound(s).

In one embodiment of the invention, the copper-based particles are substantially free of at least one of the halogens, for example, at least one of fluorine, chlorine, bromine, and iodine. Preferably, the weight percent of the at least one halogen in particles that are substantially free of the at least one halogen is less than about 25%, for example, less than about 20%, 15%, 10%, or 5%.

In one embodiment, the copper-based particles are essentially free of at least one of the halogens, for example at least one of fluorine, chlorine, bromine, and iodine. Particles that are essentially free of at least one halogen have less than about 2.5% of the at least one halogen. Preferred particles have less than about 1% of the at least one halogen. In one embodiment, the copper based particles are free of at least one of the halogens.

In another embodiment, the copper-based particles may be substantially free of halogen. Preferably, the weight percent of halogen in copper-based particles that are substantially free of halogen is less than about 25%, for example, less than about 20%, 15%, 10%, or 5%.

Again, the zinc analogs of the above are useful for the zinc-based particulates of the alternate embodiments of the invention. In one embodiment the copper-based particulate material can further comprise one or more of crystalline zinc salts selected from zinc hydroxide; zinc oxides; zinc carbonate; zinc oxychloride; zinc fluoroborate; zinc borate, zinc fluoride, or mixtures thereof. The zinc salts may be in a separate salt phase, or may be mixed CU/Zn salts, or combinations thereof. In preferred embodiments the particle comprises at least about 40%, preferably at least about 60%, and more preferably at least about 80% by weight of one or more substantially crystalline (or amorphous sparingly soluble) copper salts, crystalline zinc salts, or mixtures or combinations thereof.

In one embodiment the copper-based particulate preservative treatment for wood can further comprise zinc-based particulates comprising one or more of crystalline zinc salts selected from zinc hydroxide; zinc oxides; zinc carbonate; zinc oxychloride; zinc fluoroborate; zinc borate, zinc fluoride, or mixtures thereof. The preferred zinc-based substantially crystalline material are zinc hydroxide, zinc borate, zinc carbonate, or mixture thereof, which may be doped with other cations, e.g., from 0.1 to 10% copper, from 0.1 to 10% magnesium, or both, for example, based on the total weight of the cations in the substantially crystalline (or amorphous sparingly soluble) material. In preferred embodiments the particle comprises at least about 40%, preferably at least about 60%, and more preferably at least about 80% by weight of one or more crystalline zinc salts.

Preferred embodiments of the invention comprise particles comprising one or more of copper hydroxide, alkaline copper carbonate, alkaline copper oxychloride, tribasic copper sulfate, copper borate, or mixtures thereof. The most preferred embodiments of the invention comprise particles comprising copper hydroxide, alkaline copper carbonate, copper borate, or mixtures thereof.

Coatings for the Copper-Based and Zinc-Based Particulates.

In any of the above-described embodiments, the substantially crystalline copper composition in copper-based particulates and/or copper-based particulate material can further comprise one or more materials disposed on the exterior of the particles to inhibit dissolution of the underlying substantially crystalline (or amorphous sparingly soluble) copper material at least for a time necessary to prepare the formulation and inject the prepared wood treatment composition. Over time, however, there is unfavorable particle growth via dissolution and precipitation processes and also particle growth via agglomeration. Also, the particulates are very susceptible to premature dissolution if the slurry is formed with an acidic water. In preferred embodiments, either the particulates containing, for example, alkaline copper carbonate, copper hydroxide, copper borate, alkaline copper nitrate, copper oxychloride, tribasic copper sulfate. Additionally or alternatively the acid-soluble particles are coated with a substantially inert coating, for example a trace outer coating of e.g. copper phosphate or copper sulfide, or a coating of a polymeric material such as dispersants, or with a thin hydrophobic coating, or any combination thereof. In one embodiment the particles are treated with a dispersing material which is substantially bound to the particles.

The milled copper-based, zinc-based, and/or tin-based particles described above are readily slurried and injected into wood after the milling process. Generally, however, milling is done well before the particles are slurried and injected. The particles may be shipped in a dry form or in a wet form. The milled particles may be transported to a site as a dry mix or as a concentrated slurry, which is then formed into an injectable slurry, and then after some indeterminate storage time the particles may be injected into wood. Particulates in solution have a tendency to grow over time by 1) the thermodynamically driven tendency of sub-micron particles in solution to grow by a dissolution/reprecipitation process, where there is a greater tendency for small particles to slowly dissolve and for the salts to reprecipitate on the larger crystals. It is not uncommon, in unstabilized slurries, for the median particle size to increase by 50% over a period of a day or two. The goal is to simultaneously achieve the critical particle size, particle size distribution, and particle stability at a cost where the material can be commercially used and at the point where the material will be commercially used. Therefore, it is advantageous to have a coating on the particle to substantially hinder dissolution of the particle while the particle is slurried. However, the coating should not overly hinder dissolution of the particle in the wood matrix. Further, no coating to hinder dissolution is desirable for copper oxides particulates.

Inorganic Coating—

Generally, the discussion focuses on the preferred copper-based particulates, but the compositions and methods are equally applicable to the zinc-based and tin based particulates. The substantially crystalline (or amorphous sparingly soluble) copper-based material, zinc-based material, and/or tin-based material can be stabilized by a partial or full coating of an inorganic salt. The manufacturing process is amenable to the formation of a substantially inert inorganic coating on the particle that will be of such low thickness that the coating will not substantially hinder particle dissolution in the wood. The preferred coatings are very low solubility metal salts of the underlying metal cations, e.g., copper, zinc, or tin. Exemplary very low solubility salts include copper sulfide ($K_{sp}$=6 E-36), copper(II) phosphate ($K_{sp}$=1 E-37), and copper 8-quinolinolate ($K_{sp}$=2 E-30). The selection between sulfide, 8-quinolinolate, and phosphate generally depends on which coating shows the greatest protection for the particular substantially crystalline (or amorphous sparingly soluble) material, at the particular size distribution and particle morphology that may exist. A coating of a very low solubility salt can substantially arrest the dissolution/reprecipitation process by severely limiting the amount of copper that can dissolve. The coating, however, is mechanical protection only. Exposed portions of the underlying substantially crystalline (or amorphous sparingly soluble) copper-, zinc-, or tin-based particulates are subject to dissolution. Further, the inorganic coating is generally at most a few atoms to a few nanometers in depth.

An inorganic coating can be formed during and immediately after the particulate precipitation process, for example by adding after admixing the dissolved copper solution and the dissolved anion solution together to form the "precipitation solution", e.g., after precipitation of the substantially crystalline (or amorphous sparingly soluble) particulates has begun. In one embodiment, the admixed copper-anion solution has a small excess of anions. Precipitation of the desired copper salts is generally fast, but adding a phosphate composition (as acid phosphate, or as a partially neutralized acid phosphate) in an amount to give a concentration between a few hundred ppm and a few percent by weight will cause a layer of copper sulfate to form, for example, between crystals or even over the crystals of the substantially crystalline copper material. Alternately, a source of sulfide or 8-quinolinolate can be added to the precipitation solution. The advantage is the newly formed substantially crystalline (or substantially amorphous) material is fresh and therefore more reactive toward the added phosphate ions than would be an aged precipitate. This is not a preferred mechanism, however, because during milling some of the coating will be abraded away, and some previously unexposed substantially crystalline (or amorphous sparingly soluble) material will now be exposed. Additionally, the amount of material used to get the required concentration of anions in the precipitation solution is much more than is needed to form a coating on particulates.

The particles may be wet-milled using a very fine milling material and a fluid containing a source of sulfate ions, phosphate ions, or less preferably (because of odor and handling problems) sulfide ions. In one preferred embodiment, the wet milling process uses as the milling fluid a composition comprising between a few hundred ppm of phosphate to about 6% phosphate, for example between 0.1% phosphate to 3% phosphate. Small amounts of phosphate will take hours or days to form a completely protective coating, while a more concentrated solution may form a protective coating in minutes. Advantageously the milling liquid has a pH between about 6 and about 9.5, for example between about 7 and about 8.5. This high concentration of phosphate is not wasteful because the milling fluid can be re-used, and also because the milling fluid is a relatively small volume. Such milling in the phosphate-containing milling fluid, for example for a time ranging from 5 minutes to 4 hours, typically from 10 minutes to 30 minutes, will promote the formation of a thin coating of copper phosphate over the substantially crystalline (or amorphous sparingly soluble) copper material. As the coating is probably only a few atoms in thickness, the coating will dissolve in good time within the wood so as not to impair exposure of the underlying substantially crystalline copper material in the wood. Alternatively, a source of sulfide or 8-quinolinolate can be added to the milling liquid. Sulfide is again not preferred, for safety reasons. If sulfide is added the pH should be above 8, preferably above 9. The addition of the 8-quinolinolate is not an inorganic coating, and the adherence of a coating of an organic nature may be beneficial.

In another embodiment, the copper-based particles after milling can be exposed to a rinse solution that contains between a few hundred ppm of phosphate to about 6% phosphate, for example between 0.1% phosphate to 3% phosphate. U.S. Pat. No. 4,404,169 describes a process of producing phosphate-stabilized particulates. Phosphate ions are added to a suspension of copper oxychloride in an aqueous phase. The copper oxychloride is then reacted with alkali metal hydroxide or alkaline earth metal hydroxide, and the cupric hydroxide precipitated as a result of the suspension is washed and then re-suspended and subsequently stabilized by the addition of acid phosphate to adjust a pH value of 7.5 to 9. The suspended copper oxychloride is reacted in the presence of phosphate ions in an amount of 1 to 4 grams per liter of the suspension and at a temperature of 20° C. to 25° C. and the resulting cupric hydroxide is stabilized with phosphate ions in an amount of 3 to 6 grams per liter of the suspension. Advantageously, the rinse liquid has a pH between about 6 and about 9.5, for example between about 7 and about 8.5. After contacting the particles, advantageously for at least a minute or more, this rinse solution can itself be rinsed away with fresh water. Alternatively, a source of sulfide or 8-quinolinolate can be added to the rinse liquid. If sulfide is added, the pH should be above 8, preferably above 9.

In another embodiment, the copper-based particles after milling can be exposed to a rinse solution that contains between a few hundred ppm of phosphate to about 1% phosphate, for example between 0.1% phosphate to 0.5% phosphate ions (by weight of the rinse). After contacting the particles, advantageously, for at least a minute or more, this rinse solution can itself be rinsed away with fresh water, and the particles can be rinsed with a solution comprising a few hundred ppm of soluble copper to about 1% soluble copper, for example between 0.1% phosphate to 0.5% soluble copper ions. This copper-containing solution can be rinsed off with a minimum quantity of water, and the rinsed particulates can be re-exposed to a rinse solution that contains between a few hundred ppm of phosphate to about 1% phosphate, for example, between 0.1% phosphate to 0.5% phosphate ions. Advantageously the fluids have a pH between about 6 and about 9.5, for example between about 7 and about 8.5.

In some embodiments some copper-containing particulates are stabilized with a coating, and some particulates are not subject to such stabilization. For example, advantageously only the very small particulates, e.g., smaller than about 0.05 microns in diameter, are stabilized by a low solubility covering layer.

The invention also embraces embodiments where particles are substantially free of an inorganic coating.

Organic Coating—

Copper-based particles (or zinc-based particles, or tin-based particles, or mixtures thereof) of the invention may be used directly to preserve wood or wood products. The copper-based, zinc-based, or tin-based particles or mixtures thereof may additionally comprise an organic coating, e.g., an organic layer that partially or completely covers the exterior surface area of the particulates. The protective organic layer may additionally function as one or more other active agents, as discussed infra. This organic coating can comprise a variety of materials having a variety of functions over and above being an organic layer acting as a protective layer temporarily isolating the sparingly soluble salt from the aqueous carrier to slow dissolution of particulates in the slurry, including: 1) an organic biocide carrier, 2) a dispersing/anti-aggregation/wettability modifying agent, 3) one or more biocides, or any combinations thereof. The oil coating can comprise for example light oils, dehydrating oils, polymeric films, organic biocides, disbursing agents, anti-coagulating agents, or mixtures thereof.

In one embodiment, at least some of the particulates are coated with an organic protective coating. The particulates may have been previously coated with an inorganic coating. The organic coating should provide a thin layer of organic material that at least partially coats the particulate and for a period of time reduces the tendency of the sparingly soluble copper, zinc, and/or tin salts in the particulates to dissolve in the slurry.

Generally such coatings are extremely thin, with a particulate comprising, for example, between about 0.1% to about 50% by weight, more typically from about 0.5% to about 10%, of the weight of the above-mentioned sparingly soluble salts. The coating may cover only a portion of the exterior surface area, for example only 50% of the external surface area of a particulate.

The hydrocarbon composition can include one or more hydrophobic oils, and/or may comprise an organic compound having one or more polar functional groups which increase adherence of, for example, mono- and/or poly-carboxylic acids that may be at least partially neutralized with a metal such as a fatty acid or a polycarylic polymer, a surfactant and/or a disbursing agent, amphoteric agents, an organic biocide including an amine, azole, triazole, or any other organic biocides, a film-forming polymer such as a sulfonated ionomer, or mixtures thereof. These and other organic and/or organometallic components that form an organic layer will generally be referred to as a "hydrocarbon layer" or "hydrocarbon composition."

An organic coating may be formed by contacting particulates with a hydrocarbon composition containing the materials to be deposited onto the exterior surface of the particle. The contacting may occur in a slurry or may be done with a paste of water-wetted particulates or may be done with dried particulates. The less free water, the easier it is to promote adherence between the hydrocarbon composition to the particulates.

Heating a mixture of particulates and the hydrocarbon composition will also help the hydrocarbon composition wet and adhere to the particulates. Advantageously, in one embodiment most of the solvent of the hydrocarbon composition is volatile and is removed prior to injection of the particulates into the wood. This will leave a thin layer of a more concentrated biocide in heavier oils and/or binders than was found in the hydrocarbon/biocide composition. The organic coating generally becomes more adherent if the coated particulates are allowed to age, and/or are subjected to heat, for example, to 35° C. or above for a period of an hour, for example.

Incorporating some solvents, typically polar solvents, e.g., at least 10%, for example, at least 30% or at least 50% by weight of solvents such as one or more of alcohols, amides, ketones, esters, ethers, glycols, and such into the particulates may help the hydrocarbon layer composition wet the particulates, and will allow thinner hydrocarbon layers to be deposited. Solvents are lower molecular weight and higher volatility than oils, and solvents may be stripped from the organic coating before slurrying the particles or during kiln drying of the wood. The hydrocarbon composition may therefore comprise optional solvents and/or diluents, for example, a mixture of an oily or oil-type organochemical compound and a solvent of low volatility and/or a polar organochemical solvent or solvent mixture. Organochemical oils which are preferably employed are oily or oil-type solvents with an evaporation number of above 35 and a flash point of above 30° C., preferably above 45° C. Such water-insoluble, oily and oil-type solvents of low volatility which are used are suitable mineral oils or their aromatic fractions or mineral-oil containing solvent mixtures, preferably white spirit, petroleum and/or alkyl benzene. Mineral oils include those with a boiling range of from 170 to 220° C., spindle oil with a boiling range of from 250 to 350 v, petroleum and aromatics with a boiling range of from 160 to 280° C., oil of turpentine and the like. In one embodiment, liquid aliphatic hydrocarbons with a boiling range of from 180 to 210° C. or high-boiling mixtures of aromatic and aliphatic hydrocarbons with a boiling range of 180 to 220° C. and/or spindle oil and/or monochloronaphthalene are used, for example, a monochloronaphthalene. The organic oily or oil-type solvents of low volatility and with an evaporation number of above 35 and a flash point of above 30° C., preferably above 45° C., can be replaced in part by organochemical solvents of high or medium volatility, with the proviso that the preferred solvent mixture also has an evaporation number of above 35 and a flashpoint of above 30° C., preferably 45° C., and that the biocides and/or other compounds are soluble or emulsifiable in this solvent/oil mixture. In one embodiment, aliphatic organochemical solvents which contain hydroxyl and/or ester and/or ether groups are used, such as, for example, glycol ethers, esters or the like. Advantageously the hydrocarbon mixture comprises binders to wet and adhere to the particulate, for example, synthetic resins binding drying oils including linseed oil, and also binders comprising, an acrylate resin, a vinyl resin, for example polyvinyl acetate, polyester resin, polycondensation or polyaddition resin, polyurethane resin, alkyd resin or modified alkyd resin, preferably of medium oil length, phenol resin, hydrocarbon resin such as indene/coumarone resin, silicone resin, drying vegetable and/or drying oils and/or physically drying binders based on a natural and/or synthetic resin. Pertinent agricultural drying oils include linseed, soybean, canola, rapeseed, sunflower, tung and castor oils.

This organic coating can comprise a variety of materials having a variety of functions, including, but not limited to, surface-active agents and organic biocides.

Surface-Active Agents—

Agents improving the suspension of the particulates include dispersants such as phenyl sulfonates, alkylnaphthalene sulfonates and polymerized naphthalene sulfonates, polyacrylic acids and their salts, polyacrylamides, polyalkoxydiamine derivatives, polyethylene oxides, polypropylene oxide, polybutylene oxide, taurine derivatives and their mixtures, and sulfonated lignin derivatives. Surfactants include anionic surfactants, cationic surfactants, nonionic surfactants, or combinations thereof. Polyethyleneimine can act as a surfactant or a stabilizer and will also chelate copper. Dispersants can be used at 0.1% to 50%, preferably 0.5% to 20% or 5-10% of the particulate product.

Organic Biocides—

As previously stated, the particles may be combined with one or more additional moldicides or more generally biocides, to provide added biocidal activity to the wood or wood products. Preferred preservative treatments comprise copper-based particles having one or more additional organic biocide(s) that are bound, such as by adsorption, to a surface of the particles. Wood and wood products may be impregnated substantially homogeneously with (a) copper-based particles of the invention and (b) a material having a preservative function, such as a material bound to the surface of the copper-based particles. By substantially homogeneously we mean averaged over a volume of at least one cubic inch, as on a microscopic scale there will be volumes having particulates disposed therein and other volumes within the wood that do not have particulates therein. Thus, the distribution of preservative function within the wood or wood product is preferably not heterogeneous.

The absolute quantity of organic biocides is very low. In general, the biocides are present in a use concentration of from 0.1% to 20%, preferably 1% to 5%, based on the weight of the copper salts. The sparingly soluble copper-salt particulates of this invention are typically expected to be added to wood in an amount equal to or less than 0.25 pounds as copper per cubic foot. The organic biocide(s) at a 4% loading relative to the copper are present at about 0.16 ounces or about 3 to 4 milliliters of biocide per cubic foot. The organic biocides are often insoluble in water, which is the preferred fluid carrier for injecting the wood preservative treatment into wood, so getting adequate distribution of the biocide within the wood matrix is problematic. In prior art formulations, the wood preservative may be, for example, admixed in a large excess of oil, and the oil emulsified with water and admixed with the soluble copper for injection into the wood. Problems arise if the injection is delayed, or if the slurry has compounds which break the emulsion, and the like.

The greatest benefit is that a portion or all of the organic biocides incorporated into the wood preservative treatment can advantageously be coated on to the particulates. By adhering the biocides on particulates, a more even distribution of biocide in ensured, and the copper is disposed with the biocide and therefore is best positioned to protect the biocide from those bio-organisms which may degrade or consume the biocide. Finally, a formulation with biocide adhering to particulates does not face the instability problems that emulsions face.

Generally, so little of the organic biocide is needed that it is dissolved in and diluted with sufficient hydrocarbon material to make the phase of appreciable size. The organic material/biocide mixture can be contacted with particulates in a slurry, though it may be difficult to have the hydrocarbon phase adhere to the particulates. Pretreating the particulates with a coating of for example 8-quinolinolate will greatly increase the likelihood of the biocide absorbing on the particulate. The particulates may be concentrated, for example, to an at least 40% by weight particulates in water slurry before admixing in with the hydrocarbon/biocide composition.

The biocides can be any of the known organic biocides. Exemplary materials having a preservative function include materials having at least one of one or more: azoles; triazoles; imidazoles; pyrimidinyl carbinoles; 2-amino-pyrimidines; morpholines; pyrroles; phenylamides; benzimidazoles; carbamates; dicarboximides; carboxamides; dithiocarbamates; dialkyldithiocarbamates; N-halomethylthio-dicarboximides; pyrrole carboxamides; oxinecopper, guanidines; strobilurines; nitrophenol derivatives; organo phosphorous derivatives; polyoxins; pyrrolethioamides; phosphonium compounds; polymeric quaternary ammonium borates; succinate dehydrogenase inhibitors; formaldehyde-releasing compounds; naphthalene derivatives; sulfenamides; aldehydes; quaternary ammonium compounds; amine oxides, nitrosoamines, phenol derivatives; organo-iodine derivatives; nitrites; quinolines such as 8-hydroxyquinoline including their Cu salts; phosphoric esters; organosilicon compounds; pyrethroids; nitroimines and nitromethylenes; and mixtures thereof.

Exemplary biocides include Azoles such as azaconazole, bitertanol, propiconazole, difenoconazole, diniconazole, cyproconazole, epoxiconazole, fluquinconazole, flusiazole, flutriafol, hexaconazole, imazalil, imibenconazole, ipconazole, tebuoonazole, tetraconazole, fenbuconazole, metconazole, myclobutanil, perfurazoate, penconazole, bromuconazole, pyrifenox, prochloraz, triadimefon, triadlmenol, triffumizole or triticonazole; pyrimidinyl carbinoles such as ancymidol, fenarimol or nuarimol; chlorothalonil; chlorpyriphos; N-cyclohexyldiazeniumdioxy; dichlofluanid; 8-hydroxyquinoline (oxine); isothiazolone; imidacloprid; 3-iodo-2-propynylbutylcarbamate tebuconazole; 2-(thiocyanomethylthio) benzothiazole (Busan 30); tributyltin oxide; propiconazole; synthetic pyrethroids; 2-aminopyrimidines such as bupirimate, dimethirimol or ethirimol; morpholines such as dodemorph, fenpropidin, fenpropimorph, spiroxanin or tridemorph; anilinopyrimdines such as cyprodinil, pyrimethanil or mepanipyrim; pyrroles such as fenpiclonil or fludioxonil; phenylamides such as benalaxyl, furalaxyl, metalaxyl, R-metalaxyl, ofurace or oxadixyl; benzimidazoles such as benomyl, carbendazim, debacarb, fuberidazole or thiabendazole; dicarboximides such as chlozolinate, dichlozoline, iprdine, myclozoline, procymidone or vinclozolin; carboxamides such as carboxin, fenfuram, flutolanil, mepronil, oxycarboxin or thifluzamide; guanidines such as guazatne, dodine or iminoctadine; strobilurines such as azoxystrobin, kresoxim-methyl, metominostrobin, SSF-129, methyl 2-[(2-trifluoromethyl)pyrid-yloxymethyl]-3-methoxycacrylate or 2-[α{[(α-methyl-3-trifluoromethyl-benzyl)imino]oxy}-o-tolyl]glyoxylic acid-methylester-o-methyloxime (trifloxystrobin); dithiocarbamates such as ferbam, mancozeb, maneb, metiram, propineb, thiram, zineb, or ziram; N-halomethylthio-dicarboximides such as captafol, captan, dichlofluanid, fluorormide, folpet or tolfluanid; nitrophenol derivatives such as dinocap or nitrothal-isopropyl; organo phosphorous derivatives such as edifenphos, iprobenphos, isoprothiolane, phosdiphen, pyrazophos or toclofosmethyl; and other compounds of diverse structures such as aciberolar-S-methyl, anilazine, blasticidin-S, chinomethionat, chloroneb, chlorothalonil, cymoxanil, dichlone, dicomezine, dicloran, diethofencarb, dimethomorph, dithianon, etridiazole, famoxadone, fenamidone, fentin, ferimzone, fluazinam, flusuffamide, fenhexamid, fosetyl-alurinium, hymexazol, kasugamycin, methasuifocarb, pencycuron, phthalide, polyoxins, probenazole, propamocarb, pyroquilon, quinoxyfen, quintozene, sulfur, triazoxide, tricyclazole, triforine, validamycin, (S)-5-methyl-2-methylthio-5-phenyl-3-phenylamino-3,5-dihydroimidazol-4-one (RPA 407213), 3,5-dichloro-N-(3-chloro-1-ethyl-1-methyl-2oxopropyl)-4-methylbenzamide (RH7281), N-alkyl-4,5-dimethyl-2-timethylsilylthiophene-3-carboxamide (MON 65500), 4-chloro-4-cyano-N,N-dimethyl-5-p-tolylimidazole-1-sulfonamide (IKF-916), N-(1-cyano-1,2-dimethylpropyl)-2-(2,4-dichlorophenoxy)-propionamide (AC 382042), or iprovalicarb (SZX 722). Also included are the biocides including pentachlorophenol, petroleum oils, phenothrin, phenthoate, phorate, as well as trifluoromethylpyrrole carboxamides and trifluoromethylpyrrolethioamides described in U.S. Pat. No. 6,699,818; Triazoles such as amitrole, azocylotin, bitertanol, fenbuconazole, fenchlorazole, fenethanil, fluquinconazole, flusilazole, flutriafol, imibenconazole, isozofos, myclobutanil, metconazole, epoxyconazole, paclobutrazol, (±)-cis-1-(4-chlorophenyl)-2-(1H-1,2,4-triazol-1-yl)-cycloheptanol, tetraconazole, triadimefon, triadimenol, triapenthenol, triflumizole, triticonazole, uniconazole and their metal salts and acid adducts; Imidazoles such as Imazalil, pefurazoate, prochloraz, triflumizole, 2-(1-tert-butyl)-1-(2-chlorophenyl)-3-(1,2,4-triazol-1-yl)-propan-2-ol, thiazolecarboxanilides such as 2',6'-dibromo-2-methyl-4-trifluoromethoxy-4'-trifluoromethyl-1,3-thiazole-5-carboxanilide; fungicides such as azaconazole, bromuconazole, cyproconazole, dichlobutrazol, diniconazole, hexaconazole, metconazole, penconazole, epoxyconazole, methyl(E)-methoximino[a-(o-tolyloxy)-otolyl)]acetate, methyl (E)-2-{2-[6-(2-cyanophenoxy)-pyrimidin-4-yloxy]phenyl}-3-methoxyacrylate, methfuroxam, carboxin, fenpiclonil, 4(2,2-difluoro-1,3-benzodioxol-4-yl)-1Hpyrrole-3-carbonitrile, butenafine, and 3-iodo-2-propynyl-n-butylcarbamate (IPBC); triazoles such as described in U.S. Pat. Nos. 5,624,916, 5,527,816, and 5,462,931; the biocides described in U.S. Pat. No. 5,874,025; 5-[(4-chlorophenyl) methyl]-2,2-dimethyl-1-(1H-1,2,4-triazol-1-yl-methyl)cyclopentanol; Methyl(E)-2-[2-[6-(2-cyanophenoxy)pyrimidin-4-yloxy]phenyl]3-methoxyacrylate; methyl(E)-2-[2-[6-(2-thioamidophenoxy)pyrimidin-4-yloxy]phenyl]-3-methoxyacrylate; methyl(E)-2-[2-[6-(2-fluorophenoxy) pyrimidin-4-yloxy]phenyl]-3-methoxyacrylate; methyl(E)-2-[2-[6-(2,6-difluorophenoxy)pyrimidin-4-yloxy]phenyl]-3-methoxyacrylate; methyl(E)-2-[2-[3-(pyrimidin-2-yloxy) phenoxy]phenyl]-3-methoxyacrylate; methyl(E)-2-[2-[3-(5-methylpyrimidin-2-yloxy)-phenoxy]phenyl]-3-methoxyacrylate; methyl(E)-2-[2-[3-(phenylsulphonyloxy) phenoxy]phenyl]-3-methoxyacrylate, methyl(E)-2-[2-[3-(4-nitrophenoxy)phenoxy]phenyl]-3-methoxyacrylate; methyl (E)-2-[2-phenoxyphenyl]-3-methoxyacrylate; methyl(E)-2-[2-(3,5-dimethylbenzoyl)pyrrol-1-yl]-3-methoxyacrylate; methyl(E)-2-[2-(3-methoxyphenoxy)phenyl]-3-methoxyacrylate; methyl(E)-2[2-(2-phenylethen-1-yl)-phenyl]-3-methoxyacrylate; methyl(E)-2-[2-(3,5-dichlorophenoxy) pyridin-3-yl]-3-methoxyacrylate; methyl(E)-2-(2-(3-(1,1,2,2tetrafluoroethoxy) phenoxy)phenyl)-3-methoxyacrylate; methyl(E)-2-(2-[3-(alphahydroxybenzyl)phenoxy]phenyl)-3-methoxyacrylate; methyl(E)-2-(2-(4-phenoxypyridin2-yloxy)phenyl)-3-methoxyacrylate; methyl(E)-2-[2-(3-n-propyloxyphenoxy)phenyl]-3-methoxyacrylate; methyl(E)-2-[2-(3-isopropyloxyphenoxy)phenyl]-3-methoxyacrylate; methyl(E)-2-[2-[3-(2-fluorophenoxy) phenoxy]phenyl]-3-methoxyacrylate; methyl(E)-2-[2-(3ethoxyphenoxy) phenyl]-3-methoxyacrylate; methyl(E)-2-[2-(4-tert-butylpyridin-2-yloxy)phenyl]-3-methoxyacrylate; methyl(E)-2-[2-[3-(3-cyanophenoxy)phenoxy]phenyl]-3-methoxyacrylate; methyl(E)-2-[2-[(3-methylpyridin-2-yloxymethyl)phenyl]-3-methoxyacrylate; methyl(E)-2-[2-[6-(2-methylphenoxy) pyrimidin-4-yloxy]phenyl]-3-methoxyacrylate; methyl(E)2-[2-(5-bromopyridin-2-yloxymethyl)phenyl]-3-methoxyacrylate; methyl(E)-2-[2-(3-(3iodopyridin-2-yloxy) phenoxy)phenyl]-3-methoxyacrylate; methyl(E)-2-[2-[6-(2-chloropyridin-3-yloxy)pyrimidin-4-yloxy]phenyl]-3-methoxyacrylate; (E),(E)-methyl-2-[2-(5,6-dimethylpyrazin2-ylmethoximinomethyl)phenyl]-3-methoxyacrylate; (E)-methyl-2-{2-[6-(6-methylpyridinyloxy)pyrimidin-4-yloxy]phenyl}-3-methoxyacrylate; (E),(E)-methyl-2-{2-[(3-methoxyphenyl) methyloximinomethyl]phenyl}-3-methoxyacrylate; (E)-methyl-2-{2-[(6-(2azidophenoxy)-pyrimidin-4-yloxy] phenyl}-3-methoxyacrylate; (E),(E)-methyl-2-{2-[(6-phenylpyrimidin-4-yl)-methyloximinomethyl]phenyl}-3-methoxyacrylate; (E),(E)-methyl-2-{2-[(4-chlorophenyl)-methyloximinomethyl]phenyl}-3-methoxyacrylate; (E)-methyl-2-{2-[6-(2-npropylphenoxy)-1,3,5-triazin-4-yloxy] phenyl}-3-methoxyacrylate; (E),(E)-methyl-2-{2-[(3-nitrophenyl)methyloximinomethyl]phenyl}-3-methoxyacrylate; Succinate dehydrogenase inhibitors such as Fenfuram, furcarbanil, cyclafluramid, furmecyclox, seedvax, metsulfovax, pyrocarbolid, oxycarboxin, shirlan, mebenil (mepronil), benodanil, and flutolanil; Benzimidazoles, such as carbendazim, benomyl, furathiocarb, fuberidazole, thiophonatmethyl, thiabendazole or their salts; Morpholine derivatives, such as tridemorph, fenpropimorph, falimorph, dimethomorph, dodemorph; aldimorph, fenpropidine and their arylsulphonates, such as, for example, p-toluenesulphonic acid and p-dodecylphenylsulphonic acid; Benzothiazoles, such as 2-mercaptobenzothiazole; Benzamides, such as 2,6-dichloro-N-(4-trifluoromethylbenzyl)-benzamide; Formaldehyde and formaldehyde-releasing compounds, such as benzyl alcohol mono(poly)-hemiformal, oxazolidine, hexa-hydro-S-triazines, Nmethylolchloroacetamide, paraformadehyde, nitropyrin, oxolinic acid, tecloftalam; Tris-N(cyclohexyldiazeneiumdioxy)-aluminium; N-(cyclohexyldiazeneiumdioxy)-tributyltin; N-octylisothiazolin-3-one; 4,5-trimethylene-isothiazolinone; 4,5-benzoisothiazolinone; Nmethylolchloroacetamide; Pyrethroids, such as allethrin, alphamethrin, bioresmethrin, byfenthrin, cycloprothrin, cyfluthrin, decamethrin, cyhalothrin, cypermethrin, deltamethrin, alpha-cyano-3-phenyl-2-methylbenzyl 2,2-dimethyl-3-(2-chloro-2-trifluoromethylvinyl)cyclopropanecarboxylate, fenpropathrin, fenfluthrin, fenvalerate, flucythrinate, flumethrin, fluvalinate, permethrin, resmethrin and tralomethrin; Nitroimines and nitromethylenes, such as 1-[(6-chloro-3-pyridinyl)-methyl]-4,5-dihydro-N-nitro-1H-imidazol-2-amine (imidacloprid), and N-[(6-chloro-3-pyridyl)methyl]-N2-cyano-NJ-methylacetamide (NI25); Quaternary ammonium compounds, such as didecyldimethylammonium salts, benzyldimethyltetradecylammonium chloride, benzyldimethyldodecylammonium chloride, and didecyldimethaylammonium chloride; Phenol derivatives, such as tribromophenol, tetrachlorophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol and their alkali metal and alkaline earth metal salts; iodine derivatives, such as diiodomethyl p-tolyl sulphone, 3-iodo-2-propynyl alcohol, 4-chloro-phenyl-3-iodopropargyl formal, 3-bromo-2,3diiodo-2-propenyl ethylcarbamate, 2,3,3-triiodoallyl alcohol, 3-bromo-2,3-diiodo-2-propenyl alcohol, 3-iodo-2-propynyl n-butylcarbamate, 3-iodo-2-propynyl n-hexylcarbamate, 3-iodo-2-propynyl cyclohexylcarbamate, 3-iodo-2-propynyl phenylcarbamate; Microbicides having an activated halogen group, such as chloroacetamide, bronopol, bronidox, tectamer, such as 2bromo-2-nitro-1,3-propanediol, 2-bromo-4'-hydroxy-acetophenone, 2,2-dibromo-3-nitrilepropionamide, 1,2-dibromo-2,4-dicyanobutane, β-bromo-β-nitrostyrene; and combinations thereof. These are merely exemplary of a few classes of the known and useful biocides, and the list could easily extend for pages.

The preferred biocides are oil-soluble, and include quaternary ammonium compounds including, for example, didecyldimethylammonium salts; azoles/triazoles including, for example, N-alkylated tolytriazoles, metconazole, imidacloprid, hexaconazole, azaconazole, propiconazole, tebuconazole, cyproconazole, bromoconazole, and tridemorph tebuconazole; moldicides; HDO available commercially by BASF, or mixtures thereof. Biocides such as tebuconazole are quite soluble in common organic solvents, while others such as chlorothalonil possess only low solubility.

To apply the biocide to particulates, the biocide/hydrocarbon composition is admixed, taking care that the biocide is dispersed and preferably solubilized in the hydrocarbon composition. The biocide/hydrocarbon composition can be prepared in a manner known per se, for example, by mixing the active compounds with the solvent or diluent, emulsifier, dispersant and/or binder or fixative, water repellant, and, if appropriate, dyes and pigments and other processing auxiliaries. Then, the biocide/hydrocarbon composition is admixed with particulates, where the particulates can be suspended in a slurry, be wet, or be dry. The composition is mixed to aid the wetting of and distribution of the biocide/hydrocarbon composition to particulates. The composition may be heated, for example to about 40° C., and is also beneficially allowed to sit for a period ranging from minutes to hours. The mixture can then be incorporated into a slurry or be dried or formulated into a stable concentrated slurry for shipping.

In an alternative embodiment, the biocide/hydrocarbon composition is applied as a spray or aerosol onto individual particles, such as particles suspended in a gas stream. These coated particulates are then treated to prevent coalescence by, for example, drying the oil to remove tackiness, or coating the particle with other adjuvants such as anticoagulants, wettability agents, dispersibility agents, and the like. Such a product can be stored, shipped, and sold as a dry pre-mix.

In another embodiment, the particles are wetted with a light hydrocarbon material, which may or may not contain biocide, and the hydrocarbon material is then substantially removed by washing or drying, leaving a very thin layer of hydrocarbon residue that may range, for example, from 1 to 30 nanometers thick. Such a very thin layer will have negligible tackiness and negligible weight, but will protect the particulate from dissolution and will discourage coagulation in the slurry.

Alternate Organic Biocide Carrier—

In another embodiment, only a fraction of the particulates, be they copper-based, zinc-based, or tin-based, may be coated with the hydrocarbon/biocide combination. Some precipitation techniques are known to produce salts having high porosity, and these high porosity salts can absorb a substantial quantity of the biocide therein without forming a tacky coating.

In another embodiment, the organic biocide/hydrocarbon composition is contacted with a porous inert particulate carrier, for example 0.1 micron in diameter high porosity alumina, silica, zeolites, diatomaceous earth, attapulgite clay, or the like. Such material is readily available. For example, U.S. Pat. No. 5,527,423 disclosed alumina with a maximum particle size below 0.3 microns, having high porosity as evidenced by a BET surface area of several hundred square meters per gram, and shows this material can be made into a stable slurry. Preferred zeolites include Ag, Zn or Cu-containing zeolites, which themselves have a biocidal activity. These carrier materials are inexpensive, they do not contribute bio-nourishment as does the polymeric nanoparticles, and the rigid alumina/silica/zeolite/diatom/clay particulates will hold the biocides within the pores thereof during preparation of the slurry and injection of the slurry, or for example during admixing with glue and/or resins to make wood composites. Therefore, such inert carrier/organic biocide particulates and, additionally or alternatively, biocidal zeolite/organic biocide particulates would be useful even with the soluble copper wood preservative treatments in commercial use today. Such particulates advantageously have a solid, typically insoluble, crystalline structure that is advantageously between about 0.01 to about 0.3 microns in average diameter, for example, between about 0.05 to about 0.2 microns in average diameter. A method of manufacturing said particulates is to pull a vacuum on a quantity of dry carrier material, and then introduce thereto a composition comprising a major portion (e.g., 50% to 90%) of solvent(s), advantageously a minor portion (e.g., 5% to 48%) of oil(s), and including between 1% and 40% of organic biocides. The composition is mixed with the inert carrier and pressure may be exerted to fill the pores of the inert carrier material with the composition. Then, the solvents and optionally some of the oils may be removed by drying, heat, or by vacuum. Assuming 30% effective porosity in an alumina carrier is filled to one third with a hydrocarbon/biocide composition having 20% by weight of biocide, the total amount of biocide carrier material needed to treat 100 cubic feet of wood would be about 1 to 2 cups of alumina.

Beneficially, organic biocide is slowly leached from the particulates. The biocide formulation in an inert particulate carrier advantageously comprises oils to help transport biocide from the center of the particulate to the exterior of the particulate, and/or may include binders to increase the tenacity of the biocide to the particulates. These particulates will protect the biocide dispersed within the pores thereof, and will reduce the leach rate of the biocide. These particulates are an improvement over emulsions in that they ensure a stable formulation and uniform dispersion of the organic biocides in wood. The carrier material, for example alumina, can be milled with the same equipment used to mill the copper salt containing particulates. These biocide-containing polymers can then be slurried with the copper-based particulates of the current invention and both solids can be injected. The advantage of this process is that the carrier, for example, alumina, can be separately prepared and treated so that the alumina will not be tacky, by, for example, driving off the lighter oils and leaving only a very thin layer of biocide within the pores of the carrier. A second advantage is that the alumina/biocide can be used as a filler in a premix, thereby encouraging mixing properties.

An exemplary preservative of the invention comprises a flowable material comprising copper-based particles of the invention. Exemplary flowable materials include liquids, emulsions, slurries, and suspensions.

In one embodiment, a preservative of the invention comprises one or more materials additional to the copper-based particles, the additional materials preferably also providing a preservative function. For example, an exemplary preservative comprises an emulsion comprising the copper-based particles, where at least one phase of the emulsion may comprise one or more materials having a preservative function. Exemplary materials having a preservative function include materials having at least one of one or more triazole groups, one or more quaternary amine groups, and one or more nitroso-amine group. Mixtures of these materials may be used. Preferred preservative materials inhibit organisms that may be resistant to copper-based preservatives. Biocides useful in wood or wood product preservation are preferred materials. Preferred preservatives comprise copper-based particles comprising one or more materials having a preservative function that are bound, such as by adsorption, to a surface of the particles. Wood and wood products may be impregnated substantially homogeneously with (a) copper based particles of the invention and (b) a material having a preservative function, such as a material bound to the surface of the copper-based particles. Thus, the distribution of preservative function within the wood or wood product is made more heterogeneous by being absorbed onto the particulates.

Finally, in one embodiment the wood preservative treatment may comprise a portion of the organic biocide coated on the copper-based particulates and another portion of the organic biocide with a particulate inert carrier. The carrier particulates containing organic biocides and/or the copper-based particulates may be treated to reduce tackiness.

Injectable Slurry

In a variation of the invention, the slurry comprises: a liquid carrier; injectable solid particulates comprising one or more organic biocides; and one or more soluble copper salts or complexes including the soluble copper treatments described in the prior art. The injectable particulates can be copper-based particulates, zinc-based particulates, tin-based particulates, inert carrier-based particulates, bioactive zeolite-based particulates, or mixtures thereof. The particulates in this variant of the invention are primarily carriers for the organic biocides. An exemplary particle comprises copper hydroxide having an average particle diameter of less than about 500 nanometers, for example less than about 250 nanometers, or less than about 200 nanometers, as measured by Stokes Law. Preferably, the average particle diameter is at least 25 nanometers, for example, at least 50 nanometers. In one embodiment of the invention, the particles have a surface area of at least about 10 m$^2$/gram of particles, for example, at least about 40 m$^2$/gram of particles, for example, at least about 75 m$^2$/gram of particles, for example about 80 m$^2$/gram of particles. The particle size distribution of the particulates in one embodiment is such that at least about 30% by weight of the particulates have an average diameter between about 0.07 microns and about 0.5 microns, or preferably at least about 50% by weight of the particulates have an average diameter between about 0.1 microns and about 0.4 microns.

In another variation of the invention the slurry comprises: a liquid carrier; injectable solid particulates comprising a slightly soluble copper salt; and particulates comprising metallic copper and/or zinc. An exemplary particle having an average particle diameter of less than about 500 nanometers, for example, less than about 250 nanometers, or less than about 200 nanometers, as measured by Stokes Law, and the average particle diameter is at least 25 nanometers, for example, at least 50 nanometers. The particle size distribution of the particulates in one embodiment is such that at least about 30% by weight of the particulates have an average diameter between about 0.02 microns and about 0.4 microns, or preferably at least about 50% by weight of the particulates have an average diameter between about 0.05 microns and about 0.3 microns. The metallic copper and/or metallic zinc particulates have both a minor biocidal effect and also an anti-corrosion effect. The amount of metal, either copper, zinc, or both, in the anticorrosion metallic particulates can range from about 1 part to about 25 parts per 100 parts of particulates comprising slightly soluble copper salts. The metal-containing particulates in this variant of the invention are primarily anti-corrosion additives, though they will have some biocidal effect. Further, organic biocides can be readily coated onto these metal-containing particulates. In one embodiment of this variant, the slurry comprises: A) a liquid carrier; B) injectable solid particulates comprising metallic copper and/or metallic zinc and also one or more organic biocides, and either C-1) one or more soluble copper salts or complexes including the soluble copper treatments described in the prior art, C-2) one or more injectable particulates comprising slightly soluble salts of copper and/or zinc, or C-3) both.

The copper-based particulates can comprise or consist essentially of any sparingly soluble substantially crystalline (or sparingly soluble amorphous) copper salts. In one embodiment the substantially crystalline (or amorphous sparingly soluble) copper salts in the copper-based particulates comprise or consist essentially of one or more copper salts selected from copper hydroxides; copper carbonates (e.g., "yellow" copper carbonate); basic (or "alkaline") copper carbonates; basic copper sulfates including particularly tribasic copper sulfate; basic copper nitrates; copper oxychlorides (basic copper chlorides); copper borates; basic copper borates; copper ferricyanate; copper fluorosilicate; copper thiocyanate; copper diphosphate or copper pyrophosphate, copper cyanate; and mixtures thereof. In one embodiment, the copper based particles comprise a substantially crystalline copper compound. At least about 20%, 30%, 50%, or 75% of the weight of the copper-based particles may be composed of the substantially crystalline copper compound(s).

In a preferred embodiment, the substantially crystalline (or amorphous sparingly soluble) copper salts in the copper-based particulates comprise or consist essentially of one or more copper salts selected from copper hydroxides; copper carbonates, basic (or "alkaline") copper carbonates; basic copper sulfates including particularly tribasic copper sulfate; basic copper nitrates; copper oxychlorides (basic copper chlorides); copper borates, basic copper borates, and mixtures thereof. In one embodiment, the copper-based particles comprise a substantially crystalline copper compound. At least about 20%, 30%, 50%, or 75% of the weight of the copper-based particles may be composed of the substantially crystalline copper compound.

In another embodiment the substantially crystalline (or amorphous sparingly soluble) copper salts in the copper-based particulates in a wood preservative formulation can comprise or consist essentially of a plurality of sparingly soluble substantially crystalline (or amorphous sparingly soluble) copper salts selected from copper oxide, copper hydroxides; copper carbonates, alkaline (or "basic") copper carbonates; alkaline copper sulfates; alkaline copper nitrates; copper oxychlorides; copper borates, basic copper borates, and mixtures thereof, with the proviso that at least one of the substantially crystalline (or amorphous sparingly soluble) copper salts is not a copper oxide. Of the copper oxides, Cu$_2$O is preferred over CuO. In a variant of this, the copper-based particulate material can comprise or consist essentially of one or more sparingly soluble substantially crystalline copper salts selected from copper hydroxides; copper carbonates, alkaline (or "basic") copper carbonates; alkaline copper nitrates; alkaline copper sulfates; copper oxychlorides; copper borates, basic copper borates, and mixtures thereof. In one embodiment, the copper-based particles comprise a substantially crystalline copper compound. At least about 20%, 30%, 50%, or 75% of the weight of the copper-based particles may be composed of the substantially crystalline copper compound(s).

In any of the above, the substantially crystalline (or amorphous sparingly soluble) copper composition can have a substantial amount of one or more of magnesium, zinc, or both, wherein these cations are either dispersed within the substantially crystalline (or amorphous sparingly soluble) copper composition, or be a separate phase within a particulate. In preferred embodiments of the invention, at least some particulates comprise copper hydroxide, basic copper carbonate, or both. In more preferred embodiments, the copper hydroxide comprises between 6 and 20 parts of magnesium per 100 parts of copper, for example between 9 and 15 parts of magnesium per 100 parts of copper. Alternatively, in another more preferred embodiments, the copper hydroxide comprises between 6 and 20 parts total of magnesium and zinc per 100 parts of copper, for example between 9 and 15 parts total of magnesium and zinc per 100 parts of copper. In some embodiments, the basic copper carbonate comprises between 6 and 20 parts of magnesium per 100 parts of copper, for example between 9 and 15 parts of magnesium per 100 parts of copper, or alternatively between 6 and 20 parts total of magnesium and zinc per 100 parts of copper, for example between 9 and 15 parts total of magnesium and zinc per 100 parts of copper. Alternatively or additionally, in a preferred embodiment, the copper hydroxide and/or basic copper carbonate comprises between about 0.01 and about 5 parts of phosphate per 100 parts of copper, for example between 9 and 15 parts of phosphate per 100 parts of copper.

In another preferred embodiment, the slurry comprises a sparingly soluble copper salt particulates and also comprises zinc borate particulates. Preferably, at least some of the sparingly soluble copper salt-based particulates comprise copper borate. It is known to use a two stage process where a zinc or copper salt is injected into the wood followed by a second step, wherein the borax is injected and the insoluble metal borate is formed in situ. Such a complicated, time-consuming, and therefore expensive process in not sufficiently cost-effective. As the solubility of copper borate is very pH sensitive, in a preferred embodiment the sparingly soluble copper salts comprise an alkaline material, e.g., copper hydroxide or copper carbonate, to reduce the solubility of the copper borate. The zinc borate loading can range from 0.025% to 0.5%, for example, independent of the copper loading in the wood.

In any of the above-described embodiments, the substantially crystalline copper composition in copper-based particulates and/or copper-based particulate material can further comprise one or more soluble substantially crystalline copper salts, for example copper sulfate, copper fluoroborate; copper fluoride, or mixtures thereof, where the soluble substantially crystalline copper salts phase is stabilized against dissolution.

In any of the above-described embodiments, the substantially crystalline copper composition in copper-based particulates and/or copper-based particulate material can further comprise the substantially insoluble copper salt copper phosphate, $Cu_3(PO_4)_2$. In any of the above-described embodiments, the copper composition in copper-based particulates and/or copper-based particulate material can further comprise the insoluble copper salt copper 8-quinolinolate. In any of the above-described embodiments, the composition can further comprise copper quinaldate, copper oxime, or both in particulate form. If there are copper-based particulates substantially comprising $Cu_3(PO_4)_2$ and/or copper oxide and/or copper 8-quinolinolate, the particulates should be exceedingly small, e.g., less than about 0.07 microns, preferably less than about 0.05 microns, to provide maximum surface area to help dissolution of the particles, and the wood treatment should contain another type of substantially crystalline (or amorphous sparingly soluble) copper-based particulates, e.g., basic copper carbonate, basic copper borate, tribasic copper sulfate, copper hydroxides, and the like.

The zinc analogs of the above are useful for the zinc-based particulates of the alternate embodiments of the invention. In one embodiment the copper-based particulate material can further comprise one or more of crystalline zinc salts selected from zinc hydroxide; zinc oxides; zinc carbonate; zinc oxychloride; zinc fluoroborate; zinc borate, zinc fluoride, or mixture thereof. The zinc salts may be in a separate salt phase, or may be mixed Cu/Zn salts, or combinations thereof. In preferred embodiments the particle comprises at least about 40%, preferably at least about 60%, and more preferably at least about 80% by weight of one or more substantially crystalline (or amorphous sparingly soluble) copper salts, crystalline zinc salts, or mixtures or combinations thereof.

In one embodiment the copper-based particulate preservative treatment for wood can further comprise zinc-based particulates comprising one or more of crystalline zinc salts selected from zinc hydroxide; zinc oxides; zinc carbonate; zinc oxychloride; zinc fluoroborate; zinc borate, zinc fluoride, or mixture thereof. The preferred zinc-based substantially crystalline material are zinc hydroxide, zinc borate, zinc carbonate, or mixture thereof, which may be doped with other cations, e.g., from 0.1 to 10% copper, from 0.1 to 10% magnesium, or both, for example, based on the total weight of the cations in the substantially crystalline (or amorphous sparingly soluble) material. In preferred embodiments, the particle comprises at least about 40%, preferably at least about 60%, and more preferably at least about 80% by weight of one or more crystalline zinc salts.

Preferred embodiments of the invention comprise particles comprising one or more of copper hydroxide, alkaline copper carbonate, alkaline copper oxychloride, tribasic copper sulfate, copper borate, or mixtures thereof. The most preferred embodiments of the invention comprise particles comprising copper hydroxide, alkaline copper carbonate, copper borate, alkaline copper borate, or mixtures thereof.

In preferred embodiments of this invention the slurry comprises: a liquid carrier; sparingly soluble (and preferably substantially crystalline) copper based particulates, sparingly soluble (and preferably substantially crystalline) zinc-based particulates, sparingly soluble (and preferably substantially crystalline) tin-based particulates, or mixtures thereof; and optionally the slurry also advantageously contains one or more organic biocides, one or more corrosion inhibiting agents, and optionally other ingredients including those discussed herein. The particulates, and the sparingly soluble salts forming the core thereof, have been previously discussed. The organic biocides can be in the form of a solution with the carrier (for water soluble biocides); an emulsion; a coating on the sparingly soluble copper based, zinc-based, and/or tin-based particulates; a coating on and/or in other injectable solid particulates; or any combination thereof. In one embodiment substantially all (e.g., greater than 99% by weight) of the copper-based, zinc-based particulates, and/or tin-based particulates of preferred preservatives have a diameter smaller than 0.4 microns (400 nanometers). Such particles may be insufficiently large to scatter enough light to discolor wood or wood products treated with the particles. In another embodiment, exemplary wood preservatives comprise copper-based particles having a size distribution in which at least 50% of particles have a diameter smaller than about 0.5 µm, 0.25 µm, 0.2 µm, or 0.15 µm.

An exemplary preservative of the invention comprises sparingly soluble copper salt (e.g., copper hydroxide) or sparingly soluble zinc salt particles having an average particle diameter of less than about 500 nanometers, for example less than about 250 nanometers, or less than about 200 nanometers. In a preferred embodiment, the average particle diameter is at least 25 nanometers, for example, at least 50 nanometers. In a most preferred embodiment, the sparingly soluble (and preferably substantially crystalline) copper based particulates, sparingly soluble (and preferably substantially crystalline) zinc-based particulates, and/or sparingly soluble (and preferably substantially crystalline) tin-based particulates advantageously have a median particle size below about 0.6 microns, preferably between about 0.1 and about 0.4 microns. The particle size distribution of the particulates is such that less than about 1% by weight, preferably less than about 0.5% by weight, of the particulates have an average diameter greater than 1 micron. Preferably, the particle size distribution of the particulates is such that less than about 1% by weight, preferably less than about 0.5% by weight, of the particulates have an average diameter greater than about 0.6 microns. In one embodiment the particle size distribution of the particulates is such that at least about 30% by weight of the particulates have an average diameter between about 0.07 microns and about 0.5 microns. In a preferred embodiment, the particle size distribution of the particulates is such that at least about 50% by weight of the particulates have an average diameter between about 0.1 microns and about 0.4 microns.

In preferred embodiments of this invention, the slurry is substantially free of alkanolamines, e.g., the slurry comprises less than 1% alkanolamines, preferably less than 0.1% alkanolamines, or is totally free of alkanolamines.

In preferred embodiments of this invention, the slurry is substantially free of amines, e.g., the slurry comprises less than 1% amines, preferably less than 0.1% amines, or is totally free of amines, with the proviso that amines whose primary function is as an organic biocide are excluded.

In preferred embodiments of this invention, the slurry is substantially free of ammonium compounds (e.g., ammonium hydroxide), e.g., the slurry comprises less than 1% ammonia, preferably less than 0.1% ammonia, or is totally free of ammonium compounds, with the proviso that ammonium compounds whose primary function is as an organic biocide are excluded. In another embodiment, the composition comprises an amount of ammonium hydroxide to keep the pH of the liquid carrier between about 7 and about 10, for example between about 7.5 and 9, or between about 8 and about 8.5.

In preferred embodiments of this invention, the slurry is substantially free of solvents, e.g., the slurry comprises less than 1% organic solvents, preferably less than 0.1% organic solvents, or is totally free of organic solvents.

The slurry contains sparingly soluble (and preferably substantially crystalline) copper based particulates, sparingly soluble (and preferably substantially crystalline) zinc-based particulates, sparingly soluble (and preferably substantially crystalline) tin-based particulates, or mixtures thereof. The sparingly soluble materials may have a fraction of additional cations, e.g., zinc and/or magnesium. The particulates may have an organic coating covering at least a portion of the exterior of at least a fraction of the particulates. For example, the particles can be wetted with an oil or solvent comprising e.g., linseed oil, turpentine, and/or pine oil, and typically the oil or solvent will include at least a portion of the organic biocides. In another embodiment, the slurry will alternately or additionally comprise inert metal oxide carrier particulates having organic biocide associated therewith. The particulates may have an inorganic coating covering at least a portion of the exterior of at least a fraction of the particulates. The inorganic coating in one preferred embodiment comprises copper phosphate formed by having phosphate absorb onto the sparingly soluble copper salt.

The loading of the particulates in the slurry will depend on a variety of factors, including the desired copper loading in the wood, the porosity of the wood, and the dryness of the wood. Calculating the amount of copper-based particulates and/or other particulates in the slurry is well within the skill of one of ordinary skill in the art. Generally, the desired copper loading into wood is between 0.025 and about 0.5 pounds copper per cubic foot of wood.

In a preferred embodiment, the liquid carrier consists essentially of water and, optionally, one or more additives to aid particulate dispersion, pH maintenance, interfacial tension (surfactants), and anticoagulants. In another embodiment, the carrier consists essentially of water and, optionally, one or more additives to aid particulate dispersion, pH maintenance, interfacial tension (surfactants), anticoagulants, and oil-in-water emulsion of oil containing organic biocides dissolved therein.

Advantageously, the pH of the liquid carrier is between about 7 and about 9, for example, between about 7.5 to about 8.5. The pH can be adjusted with sodium hydroxide, potassium hydroxide, alkaline earth oxides, methoxides, or hydroxides; or less preferably ammonium hydroxide. The pH of the injectable slurry is typically between pH 6 and 11, preferably between 7 and 10, for example, between 7.5 and about 9.5. Acidic pH slurries are not preferred because several of the sparingly soluble copper salts of this invention have a higher solubility at lower pH. Therefore, delays in preparing the slurry, injecting the slurry, and removing the water carrier may result in undesired dissolution of sparingly soluble material from the particulates. The pH can be adjusted to the desired pH with alkali or alkaline earth oxides, methoxides, or hydroxides, or less preferably ammonium hydroxide. Alkaline earth bases are less preferred because if carbon dioxide or carbonates are present in solution, there is a possibility of precipitation, for example, of calcite. Such precipitation may create undesired plugging of the wood during injection. The preferred ingredients to increase the pH is an alkali hydroxide, e.g., sodium hydroxide or potassium hydroxide. The pH modifying agent may be provided in the form of a preferably aqueous solution comprising at least one hydroxide salt.

The slurry is beneficially buffered, by, for example, adding phosphoric acid or salts thereof in an amount sufficient to give a phosphate content of between about 5 ppm and about 500 ppm. An alternative buffer comprises an alkali bicarbonate and alkali carbonate. The higher concentrations of phosphates may be beneficial if the particulates do not have any coatings formed thereon, as the soluble phosphate ions will discourage dissolution of the copper salts from the particulates into the liquid carrier. The salts of metal phosphates are extremely insoluble, for example, the solubility product constant of copper phosphate is about 1 E-37, so in pure water this amount of phosphate would limit the copper ion concentration to a negligible quantity. The phosphate ions would therefore discourage dissolution and re-precipitation of the copper, zinc, tin, or any combination thereof. This phosphate may also allow an existing phosphate-based coating to repair after damage by for example abrasion with other particles or abrasion while being handled. Finally, the presence of phosphate ions will slow the leach rate of copper from the wood. On the other hand, the bioactive efficacy of copper phosphate is probably very low, for the same reasons that the efficacy of copper oxides is low. The solubilized copper ions are believed to be bioactive and therefore contribute to the bioactivity of the formulation, and the solubility of copper phosphate is very low. Therefore, it is desirable that any copper phosphate coating on the particulates be so thin as to be short-lived in the wood. Excessive soluble phosphate may not allow the phosphate coating to readily break down in the wood, and this could impair the bioactivity of the particulates. Also, if the mixing tank has, for example, a residual salts from previous injection of soluble materials, then the phosphates can result in unwanted precipitates forming. For this reason the concentration of phosphates in the liquid carrier is beneficially kept below 1000 ppm, for example below 500 ppm or below 100 ppm.

In one embodiment the slurry comprises between 50 and 800 ppm of one or more scale precipitation inhibitors, particularly organophosphonates. Alternately or additionally the slurry may contain between about 50 and about 2000 ppm of one or more chelators. Both of these additives are meant to inhibit precipitation of salts such as calcium carbonate and the like, where the source of calcium may be from the water used to make up the slurry. The preferred inhibitors are hydroxyethylidene diphosphonic acid (HEDP), diethylenetriaminepentamethylenephosphonic acid (DTPMP), and/or 2-phosphonobutane-1,2,4-tricarboxylic acid (PBTC). If the preservative is in a slurry concentrate, the slurry should comprise between 10 mmoles and 100 mmoles/L of HEDP, or between 30 mmoles and 170 mmoles/L of PBTC or DTPMP. Mixtures of inhibitors are preferred, as concentrates may have more inhibitor than can readily be solubilized therein. If the preservative is in a solid form, the preservative should comprise between about 0.1 to about 1 mole HEDP per kg of particulates, or between about 0.17 to about 2 mole PBTe and/or DTPMP per kg of particulates.

In one embodiment of the invention, a precipitate comprising copper-based particles is prepared in the presence of a material that inhibits precipitation of at least one of calcium and magnesium. Alternatively, a material that inhibits precipitation of at least one of calcium and magnesium is added to a mixture comprising copper-based particles of the invention. In one embodiment, the precipitation inhibitor is a chelator comprising having at least one ethylene diamine compound, such as an ethylenediamine-tetramethylene compound or ethylenediaminetetracetate compound. An acid, such as a phosphonic or acetic acid, of the ethylenediamine compound may be used. Salts of the ethylenediamine compound may also be used. In one embodiment, the precipitation inhibitor comprises at least one and preferably at least two phosphonic groups. The precipitation inhibitor may comprise a phosphonic acid or salt of a phosphonic acid. The precipitation inhibitor may comprise at least one of a hydroxyethylidene diphosphonic acid and an aceto diphosphonic acid. A suitable phosphonate may be synthesized from phosphorous acid by reaction with formaldehyde and either ammonia or amines. A wood preservative of the invention may include at least one of a ethylenediamine tetra methylenephosphonic acid, a hexamethylenediamine tetra methylenephosphonic acid, a diethylenetriamine penta methylenephosphonic acid, and a 1-hydroxy ethane diphosphonic acid.

In some embodiments of the invention, the sparingly soluble (and preferably substantially crystalline) copper based particulates, sparingly soluble (and preferably substantially crystalline) zinc-based particulates, sparingly soluble (and preferably substantially crystalline) tin-based particulates, or mixtures thereof, are used in conjunction with a liquid carrier comprising soluble copper, for example, any of the soluble copper formulations discussed in the background, including, for example, a copper monoethanolamine carbonate complex, copper monoethanolamine borate complex, copper azole borate, or copper citrate. Advantageously, this soluble copper material is kept separate from the particulate slurry or paste of this invention until the injectable slurry is formulated. If such material is admixed into a concentrated slurry or paste for shipping and storage, then beneficially the particulates have one or more protective coating layers thereon to minimize copper dissolution of the particulates.

In some embodiments of the invention, the sparingly soluble (and preferably substantially crystalline) copper based particulates, sparingly soluble (and preferably substantially crystalline) zinc-based particulates, sparingly soluble (and preferably substantially crystalline) tin-based particulates, or mixtures thereof, are used in conjunction with a liquid carrier comprising one or more soluble borate salts. Soluble borates can be added in an amount from about 5 ppm to about 2000 ppm in the slurry, where less than 5 ppm has little effect and more than 2000 ppm is cost-prohibitive. Borates have both a biocidal activity and a fire retardant activity.

In some embodiments of the invention, the sparingly soluble (and preferably substantially crystalline) copper based particulates, sparingly soluble (and preferably substantially crystalline) zinc-based particulates, sparingly soluble (and preferably substantially crystalline) tin-based particulates, or mixtures thereof, are used in conjunction with a liquid carrier comprising one or more soluble chromate salts. Soluble chromates can be added in an amount from about 5 ppm to about 2000 ppm in the slurry, where less than 5 ppm has little effect and more than 2000 ppm is cost-prohibitive. Chromates have both a biocidal activity and may have a corrosion-reducing activity.

Increased corrosion of metal fillings has been observed in formulations using soluble copper preservatives, as opposed to the prior art CCA formulations. The slurry, having a slightly basic pH and having very low amine content, is expected to reduce the corrosion rate over that seen with soluble copper. There are additional treatment that can help reduce corrosion. The presence of small quantities of buffered phosphate may further reduce corrosion. Eliminating certain sparingly soluble salts such as the oxychlorides will remove chloride, which will reduce corrosion from that source. Finally, some of the injectable particulates can comprise at least a portion of reduced metallic zinc or copper. The particulates are advantageously sized about the same as for the injectable particulates comprising the sparingly soluble, usually substantially crystalline copper salts. Indeed, in addition to being useful in slurries of this invention, corrosion of metallic fittings may be somewhat alleviated by incorporating metallic copper and/or zinc particulates in the soluble copper solution preservatives of the prior art. Metallic zinc and copper are not considered to be substantially crystalline, nor are they considered to be sparingly soluble salts. The amount of these anti-corrosion metallic particulates can range from about 1 part to about 25 parts per 100 parts of copper in the sparingly soluble copper salts.

Contact with air can facilitate oxidation of certain sparingly soluble copper salts, for example, copper hydroxide (especially in very small particulate form, and especially if not coated and/or if not containing a stabilizer such as magnesium ions, to form into copper oxides). This transition is generally not preferred because copper oxide has such limited solubility that it may not be sufficiently bioactive. The concentrated slurry or paste may comprise one or more antioxidants. Soluble sulfite salts between 5 ppm and 100 ppm in the liquid carrier is a useful inexpensive antioxidant.

If the wood preservative treatment will comprise organic biocides, these biocides may be partially or fully coated onto the sparingly soluble (and preferably substantially crystalline) copper based particulates, sparingly soluble (and preferably substantially crystalline) zinc-based particulates, sparingly soluble (and preferably substantially crystalline) tin-based particulates, or mixtures thereof. Preferred preservative materials inhibit organisms that may be resistant to copper-based preservatives. Moldicides useful in wood or wood product preservation are also preferred organic biocides. Alternatively or additionally, these biocides may be partially or fully coated onto the available surface area of an inert particulate carrier. If the biocides are to be added to the slurries as an emulsion, the organic biocides are beneficially kept separate from the concentrated slurry or paste of this invention until the injectable slurry is formulated.

The slurry can advantageously contain one or more additives to aid wetting, for example surfactants. Surfactants may be in solution, or alternatively may bind to the surface. When bound to the surface these surfactants function as disbursing agents. A dispersing agent may be combined with the precipitated copper-based particles. Alternatively, copper-based particles may be formed in the presence of the dispersing agent. Preferred dispersing agents include a surface active portion that interacts with the copper-based particle and a second preferably different portion, which operates to inhibit irreversible agglomeration of the copper based particles. For example, a polyacrylate dispersing agent may include at least one carboxyl group capable of associating, such as electrostatically, with a copper-based particle and a second, hydrophobic portion that may operate to inhibit the permanent agglomeration of the copper based particles. Exemplary dispersing agents may include at least one of a surfactant, a polyacrylate, a polysaccharide, a polyaspartic acid, a polysiloxane, and a zwitterionic compound. Exemplary compounds useful as dispersing agents are disclosed in for example, Kirk-Othmer, Encyclopedia of Chemical Technology, 3rd Edition, Vol. 22 (John Wiley & Sons, 1983); Napper, Polymeric Stabilization of Colloidal Dispersion (Academic Press, 1983); and Rosen, Surfactants & Interfacial Phenomena, 2nd edition (John Wiley & Sons, 1989), all of which are incorporated herein by reference. In one embodiment of the invention, the copper-based particles may comprise a polymer. In this embodiment, the ratio of the weight of copper present in the particles to polymer present in the particles may be at least about 1 to 1, for example at least about 2 to 1, 4 to 1, 5 to 1, 7 to 1, or at least about 10 to 1. For example, if ratio of the weight of copper present in the particles to the weight of polymer present in the particles is at least about 2 to 1, the particles comprise at least about twice as much copper by weight as polymer. Another aspect of the invention relates to a preservative useful for wood or wood products, the preservative preferably comprising a preferably aqueous suspension of copper based particles. If a dispersing agent is present in the suspension, the ratio of the weight of copper present in the copper-based particles of the suspension to the weight of dispersing agent present in the suspension may be at least about 1 to 1, for example at least about 5 to 1, 10 to 1, 15 to 1, 20 to 1 or at least about 30 to 1.

In one embodiment, the dispersing agent is substantially free of phosphate ion. For example, the dispersing agent may be substantially free of trisodium phosphate. The dispersing agent may be substantially free of silicates, sodium carbonate and ammonia. By substantially free of one or more particular dispersing agents, it is meant that the weight percent of the one or more dispersing agent relative to the copper-based particles is less than 3%. In one embodiment, the weight percent of the one or more particular dispersing agents relative to the copper-based particles is less than about 2%, such as less than about 1%, for example, less than about 0.5%. In one embodiment, the dispersing agent is free of at least one of phosphate ion, trisodium phosphate, silicates, sodium carbonate, and ammonia.

Dispersing agents aid particulate dispersion and to prevent aggregation of particulates. Sub-micron sized particulates have a tendency to form much larger aggregates. Aggregates as used herein are physical combinations of a plurality of similarly-sized particles, often brought together by VanDerWaal's forces or electrostatic forces. By similarly-sized we mean the particles forming the aggregate have diameters that are generally within a factor of five of each other. Such aggregates are not desired in the compositions of this invention. If aggregates are allowed to form, they often can age into a stable aggregate that can not be readily broken up by mechanical agitation, for example by vigorous stirring of a slurry. Such aggregates may grow to a size where the aggregates are not readily injectable, or may be of a size to make the aggregates visible, therefor giving undesired color. In preferred embodiments of the invention at least 30%, preferably at least 60%, more preferably at least 90% by weight of the substantially crystalline copper-based particulates in a slurry are mono-disbursed, e.g., are not in aggregates. To prevent particulates from agglomerating, the concentrated slurry or paste may comprise cationic, anionic, and/or non-ionic surfactants; emulsifiers such as gelatine, casein, gum arabic, lysalbinic acid, and starch; and/or polymers, such as polyvinyl alcohols, polyvinyl pyrrolidones, polyalkylene glycols and polyacrylates, in quantities of 0.1 to 20% by weight, based on the weight of the particulates.

Another aspect of the invention relates to a preservative useful for wood or wood products, the preservative preferably comprising a preferably aqueous suspension of copper based particles. The suspension may be stabilized by a suspension-stabilizing amount of a dispersing agent. Preferred dispersing agents include a surface active portion that interacts with the copper-based particle and a second, preferably different portion, which operates to inhibit irreversible agglomeration of the copper-based particles. For example, a polyacrylate dispersing agent may include at least one carboxyl group capable of associating, such as electrostatically, with a copper-based particle and a second, hydrophobic portion that may operate to inhibit the permanent agglomeration of the copper-based particles. Exemplary dispersing agents may include at least one of a surfactant, a polyacrylate, a polysaccharide, a polyaspartic acid, a polysiloxane, or a zwitterionic compound. If a dispersing agent is present in the suspension, the ratio of the weight of copper present in the copper-based particles of the suspension to the weight of dispersing agent present in the suspension may be at least about 1 to 1, for example at least about 5 to 1, 10 to 1, 15 to 1, 20 to 1 or at least about 30 to 1.

The slurry formulations mentioned can be prepared in a manner known per se, for example by mixing the active compounds with the liquid carrier, and including emulsifier, dispersants and/or binders or fixative, and other processing auxiliaries. Particulates can be provided in a concentrated slurry, in a very concentrated paste, as dry particulates, as coated dry particulates, as part of a dry pre-mix, or any combination thereof.

Slurry Concentrate—

If the wood preservative is to be manufactured, stored, or transported in a wetted form, it is beneficial that it be in a concentrated form to minimize the volume and increased handling expense. Preferably the concentrated slurry or paste comprises between 5% and 80% by weight, for example between about 15% and 40%, of sparingly soluble (and preferably substantially crystalline) copper based particulates, sparingly soluble (and preferably substantially crystalline) zinc-based particulates, sparingly soluble (and preferably substantially crystalline) tin-based particulates, or mixtures thereof, with the remainder of the concentrated slurry or paste being a fluid carrier. The concentrated slurry or paste may further comprise solid particulates that are carriers for one or more organic biocides, solid particulates comprising metallic copper and/or zinc as corrosion inhibitors, or both. The fluid carrier beneficially comprises one or more additives as discussed for the slurry, including anti-oxidants; surfactants; disbursing agents; other biocidal salts and compounds; chelators; corrosion inhibitors, e.g., phosphates or metallic zinc or copper particulates; pH modifiers and/or buffers; and the like. The concentration of these additives will depend in part on the degree to which the slurry concentrate is expected to be diluted to make a commercially useful injectable slurry having the proper copper loading.

The moisture content of the copper-based particles of the invention may be reduced, such as by drying. A dispersing agent may be used to inhibit irreversible agglomeration of reduced moisture particles of the invention. The reduced moisture particles may be diluted, such as by hydration with water or combination with another liquid. Generally, dilution is with water, beneficially fresh water.

Another aspect of the invention relates to an agglomeration comprising a plurality of copper-based particles and, optionally, a dispersing agent. The agglomeration may also include one or more materials in addition to the copper-based particles that also provide a wood or wood product preservative function. The agglomeration may have a liquid content (excluding any additional preservative material that may be present) of less than about 75% by weight, for example, of less than about 50%, less than about 25%, less than about 15%, or less than about 5% by weight. The liquid may be water. The agglomeration may be diluted and/or dispersed with mixing or agitation, such as mechanically or ultrasonically.

As in the injectable slurry itself, the particle size distribution of the particulates is such that less than about 1% by weight, preferably less than about 0.5% by weight, of the particulates have an average diameter greater than 1 micron. Preferably the particle size distribution of the particulates is such that less than about 1% by weight, preferably less than about 0.5% by weight, of the particulates have an average diameter greater than about 0.6 microns. The particle size distribution of the particulates is such that at least about 30% by weight of the particulates have an average diameter between about 0.07 microns and about 0.5 microns. In a preferred embodiment, the particle size distribution of the particulates is such that at least about 50% by weight of the particulates have an average diameter between about 0.1 microns and about 0.4 microns.

The pH of the wood preservative in the form of a concentrate or paste is in general between pH about 6 and about 13, preferably between about 7 and about 10.5, for example, between about 7.5 and about 9.5. The pH can be adjusted to the desired pH with alkali or alkaline earth oxides, methoxides, or hydroxides; or less preferably ammonium hydroxide. The preferred ingredient to increase the pH is an alkali hydroxide such as sodium hydroxide. The concentrated slurry or paste is beneficially buffered, for example, by adding phosphoric acid in an amount sufficient to give a phosphate content of between about 10 ppm and about 1000 ppm.

If the wood preservative comprises organic biocides, these biocides may be partially or fully coated onto the sparingly soluble (and preferably substantially crystalline) copper based particulates, sparingly soluble (and preferably substantially crystalline) zinc-based particulates, sparingly soluble (and preferably substantially crystalline) tin-based particulates, or mixtures thereof. Alternatively, or additionally, these organic biocides may be partially or fully coated onto the surface area of an inert particulate carrier. If the organic biocides are to be added to the slurries as an emulsion, the organic biocides are beneficially kept separate from the concentrated slurry or paste of this invention until the injectable slurry is formulated.

Dry Particulates and Dry Mix for Slurry—

The particulates are preferably sold as a dry component. The dry component can be simply the copper-based, zinc-based, and/or tin based particulates, which may be coated or uncoated. If coated, the coating can be inorganic, organic, or both. The particulates advantageously comprise one or more additives such as are described as being present in the slurry, including, for example, inert particulates having organic biocides thereon; anti-oxidants; surfactants; disbursing agents; other biocidal salts and compounds; chelators; corrosion inhibitors, e.g., phosphates or metallic zinc or copper particulates; pH modifiers; and/or buffers, such as carboxylic acid salts, or inorganic salts, such as phosphate salts and the like. The additives can be coated onto the sparingly soluble copper based particulates and/or can be a second particulate.

The dry-mix material advantageously has, in addition to dry particulates discussed above, all necessary components in a single mix, and each component is present in a range that is useful when the dry mix is formed into an injectable slurry. The dry-mix material may optionally, but preferably, incorporate a granulating material, which is a material that, when wet, holds a plurality of particulates together in the form of a granule, but that dissolves and releases the individual particulates on being admixed with the liquid carrier. Granules are preferred over sub-micron-sized particulates because of dust problems and also the ease of measuring and handling a granular mixture. Granulating agents can be simple soluble salts, for example alkali carbonates, that are sprayed onto or otherwise admixed with the particulate material. Several additives to a slurry can be also used as granulating agents.

One embodiment of the invention relates to a dry-mix material having a copper content of at least about 8% by weight. A preferred material includes a plurality of copper-based particles, which may be in the form of granules. The material may be shipped, such as in granular form, to a location where the material will be prepared for use as a wood preservative. The dry-mix material may also comprise at least one of a wetting agent; a dispersing agent; a diluent, which may be a particulate comprising organic biocides thereon; an antifoaming agent; and an additional material having a biocide function.

One embodiment of the invention relates to a dry-mix material having a copper content of at least about 15% by weight. A preferred dry-mix material includes a plurality of copper based particles, which may be in the form of granules. The dry-mix material also comprises at least one of a wetting agent, a dispersing agent, a diluent, an antifoaming agent, or an additional material having a biocide function. In one embodiment, the dry-mix material is a granular material comprising about 50% to about 70%, for example about 58%, copper hydroxide or other sparingly soluble copper salts, about 10% to about 25%, for example about 18%, of a dispersing agent, such as Borrespersse NA, about 1% to about 8%, e.g., about 4%, of a wetting agent, such as Morwet EP, and about 10% to about 30% filler, e.g., about 20% attapulgite clay, such as Diluex A.

In one embodiment, the dry-mix material is a granular material comprising about 40% to about 80% by weight of a sparingly soluble copper salt, e.g., copper hydroxide, about 5% to about 30% of a dispersing agent, such as Borrespersse NA, about 1% to about 10% of a wetting agent, such as Morwet EP, and about 5% to about 30% of a inert particulate filler which may additionally comprise organic biocides absorbed thereon, e.g., attapulgite clay, such as Diluex A. In one embodiment, the dry-mix material is a granular material comprising about 58% copper hydroxide, about 18% of a dispersing agent, such as Borrespersse NA, about 4% of a wetting agent, such as Morwet EP, and about 20% attapulgite clay, such as Diluex A.

Another aspect of the invention relates to dry-mix material comprising a copper content of at least about 15%, for example, at least about 20%, such as at least about 30% by weight. In one embodiment, the dry-mix material may have a copper content of about 35% by weight. The dry-mix material has a copper content of less than about 50%, for example, less than about 45%, such as less than about 40% by weight. The dry-mix material may comprise a plurality of granules each comprising a plurality of copper-based particles. The copper-based particles may be associated with a dispersing agent.

In one embodiment, the dry-mix material comprises A) about 30% to about 70% by weight of a slightly soluble copper salt, e.g., copper hydroxide, for example, about 35% to about 65%, such as about 38% to about 61% of the slightly soluble copper salt; B) about 10% to about 35% by weight, such as about 15% to about 30% of at least one dispersing agent, e.g., lignosulfonates or polyacrylates; C) about 2.5% to about 20% by weight, such as about 5% to about 15% of at least one wetting agent, for example, a surfactant, e.g., Morwet EP available from Barton Solvents, Inc.; D) about 5% to about 25% by weight, such as about 10% to about 20% of at least one diluent, for example soluble and insoluble diluents, such as those used in agricultural products, e.g., clay, such as an attapulgite clay, or particulate carrier particles comprising organic biocide; E) about 0.05% to about 7.5% by weight, such as about 0.1% to about 5%, of at least one antifoam agent; and optionally F) about 2.5% to about 25%, alternatively less than about 7.5%, such as less than about 5% by weight, of water.

The dry-mix material may be shipped in granular form. The dry-mix material of the invention offers reduced shipping costs and improved ease of handling compared to known preservative materials. A user may receive the dry-mix material as a flowable material comprising a plurality of copper-based particles. The dry-mix material may be diluted, for example, with water or another liquid. The copper-based particles of the dry-mix material may be injected into wood and/or wood materials as a preservative. Mechanical agitation and/or mixing may be used to disperse the granules in the liquid. Upon dispersing the material, wood or wood products may be treated with the dispersed material, such as by subjecting the wood or wood products to vacuum and or pressure in the presence of the dispersed material. Upon dispersing granules of the material, dispersed copper-based particles preferably remain suspended for at least about 30 minutes without further agitation, preferably, even in standard hard water having a hardness of about 342 ppm. Once dispersed, about fifty percent of the dispersed copper-based particles may have diameters less than about 1 micron, for example, less than about 0.5 micron, such as less than about 0.25 micron. In one embodiment, about 50% of the dispersed copper-based particles have diameters less than about 0.2 micron, for example, about 50% of the dispersed copper-based particles have diameters of about 0.1 micron.

The copper-based material may comprise additional material providing a wood preservative and/or biocide function. For example, in one embodiment, the additional material comprises a plurality of copper-based particles and a co-biocide. Exemplary co-biocides may include, for example, one or more of a triazole compound, a quaternary amine, and a nitrosoamine.

Leaching Data

One object of the invention is to provide an effective, injectable copper-based particulate preservative treatment that has leaching characteristics similar to CCA. It is known that copper arsenate ($Cu_3(AsO_4)_2$) injected as a molecular layer is effective as a preservative. Therefore, the particulate preservative should provide a copper concentration roughly similar (for example, about the same to within a factor of three times) to that provided by copper arsenate treatment. Generally, leach rate tests involve high-leaching medium flow rates so the leaching medium can not easily dissolve the sparingly soluble salts, and therefore measured leach rates of particulates are expected to be low compared to leach rates from more soluble salts. By "leach rate similar to CCA," we mean the leach rate using the AWPA Standard Method E11-97 (1997), determined as percent of copper leached per hour. For a particulate inhibitor injected into wood is within a factor of about 2 above, preferably within a factor of about 1.5 above, to within a factor of 5 below, preferably within a factor of about 3 below, more preferably within a factor of about 2 below, the percent of copper leached from CCA-treated wood at 240 hours using the AWPA Standard Method E11-97 (1997), by using a test extending to at least 300 hours duration. Another object of the invention is to provide an effective, injectable copper-based particulate preservative treatment that retains more than 94% of the injected copper in a 14 day standard leach test.

Advantageously the copper-based particulate is an effective preservative. To be effective, the copper-based particles comprise one or more sparingly soluble copper salts that release a small but effective concentration of soluble copper when wetted with water. If the copper salts have too high a solubility, the copper is quickly leached out of the wood and contaminates the environment rather than protecting the wood. If the copper salts have too Iowa solubility, the copper salts (and copper oxides) are not bioactive. The dissolution rate/leach rate of the sparingly soluble copper salts used in the particulates will be a function of 1) the solubility of the sparingly soluble copper salt(s) in the leaching medium; 2) the surface area of the sparingly soluble copper salts available to contact the leaching medium; 3) the lattice energy of the crystal which must be overcome to dissolve the crystal; and 4) the flow characteristics of the leaching medium in the wood matrix, especially boundary layer effects. Each of these properties plays a role in every flowrate scenario, but some are more dominant than others at certain times. We believe the leach rates will be governed primarily by the solubility of the sparingly soluble salts and by boundary layer effects of the copper and counterions diffusing from the particulates in regimes where the leaching medium is moving extremely slowly, e.g., less than a few millimeters per day. At intermediate leachant flow rates, we believe the leach rate of copper will depend primarily on the available surface area. At higher rates, such as found in the standard test methods typically used by industry, the leach rates will be governed more by the available surface area of the sparingly soluble salts and by the lattice energy of the crystal.

Generally, surface area is known be an important factor. This is because, as the sparingly copper salts exist as approximate point sources within the wood matrix, the leaching medium typically does not contact a sufficient amount of particulates for a sufficient time to become saturated with the sparingly soluble copper salts. Dissolution is a function not only of the pH of the water within the wood and the solubility product of the particular salts in water, but also of dynamic conditions. Since the copper is present in the wood as particulates, dissolution of copper will also be restricted by the low surface area of the particles. Larger particulates will reduce the leaching rate in most leaching regimes. The dissolution of larger particulates is more dependent on surface effects than is the dissolution of smaller particulates, in part because the available surface area is lower for larger particulates. At low flow rates, boundary layer effects may multiply the effects of lower surface area, but at typical leaching regimes boundary layer effects may be minimized if the flow of the leaching medium through the wood matrix is turbulent.

The easiest way to alter surface area is to change particle size. In a simplistic model, reducing the average particle size by one half will increase the available surface area by about a factor of 2. If the particulates become too small, e.g., below about 0.02 microns (20 nanometers) in diameter or below about 10 nanometers in diameter, for many of the sparingly soluble copper salts, we believe the leaching medium will always approximate being saturated by the sparingly soluble copper salts and the available surface area will approach that of a monolayer, giving leaching properties of an injected soluble copper. The crystals may then dissolve too quickly if subjected to a high leaching regime for an extended period of time. Further, we believe that high leachant flow rates may dislodge and remove from the wood matrix very small particulates. For this reason in preferred embodiments of the invention at least about 30% or more of the sparingly soluble salts are present as particulates having a diameter greater than about 0.1 microns.

Generally, the available surface area can be further reduced by the presence of one or more coatings, be they organic, inorganic, or both. The coatings must be designed to have a coverage and efficiency such that at least a bioactive amount of copper is leached from the sparingly soluble copper salts in the particulates. In some embodiments, the coating is dissolved over a period of time, thereby allowing the available surface area of the sparingly soluble copper salts to increase with time. This is advantageous because newly-installed wood generally does not need biocides to be released until the bio-organisms invade or contact the wood, and this usually takes some time.

The solubility of the sparingly soluble copper salts can be estimated based on values of the solubility product constant. However, the presence of ions such as phosphate in the wood matrix will reduce solubility, while the presence of acids in the leachant will greatly increase solubility of most of the preferred sparingly soluble salts. At low flow rates, the pH of the leaching medium will be modified by the dissolution of the copper hydroxides and the copper carbonates. The isoelectric point of copper hydroxide is at about pH 11, making copper hydroxide a very effective base. The presence of other salts, for example phosphate ions, can further hinder leach rates by temporarily holding the solubilized copper, reducing the flow rate of copper through the wood matrix. At high leaching medium flow rates, however, such as are used in standard leaching tests, the flow rates are such that the presence of hydroxides, phosphates, and the like are minimized.

Generally, the leach rate of copper from particulates of sparingly soluble copper salts disposed in a wood matrix is dependent on particle size (and hence particle size distribution), leaching medium flow rates through the wood matrix, and a variety of other factors. The copper based particulates of the invention advantageously have a low leach rate at both relatively high leaching medium flow rates and at relatively low leaching medium flow rates, because the copper-based particulates have 1) a wide distribution of particle sizes, 2) sparingly soluble salts of differing solubilities, or 3) both.

Examples

Figure 3:
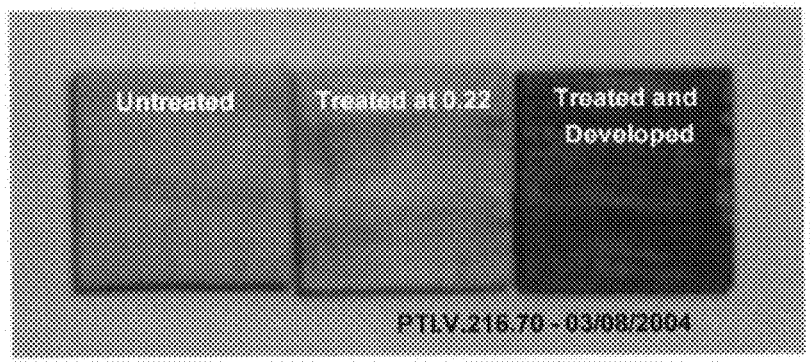
FIG. 3 is a photograph of a sliced interior section of wood block, untreated, treated, and treated and developed.

We have successfully injected slurries comprising submicron-sized particles of various sparingly soluble copper salts into standard 1 inch cubes of Southern yellow pine. Copper development by calorimetric agents (dithio-oxamide/ammonia) showed the copper to be fully penetrated across the block in the sapwood portion. FIG. 3 shows the penetration of injected particulate copper hydroxide developed with dithio-oxamide in the third picture. The stain corresponds to copper. Subsequent acid leaching and quantitative analysis of the copper from two blocks showed that loadings of 95% and 104% of expectation, or essentially 100% average of expectation had occurred. At 100% loading, values of 0.22 lbs of copper per cubic foot would be obtained.

[Leaching data from wood preserved with a prior art soluble solution of copper MEA and from a slurry of injected copper hydroxide particulates of this invention was measured following the AWPA Standard Method E11-97. The total copper leached from wood preserved with copper-MEA-carbonate is 5.7% at 6 hours, 8.5% at 24 hours, 11% at 48 hours, 22% at 96 hours, 36% at 144 hours, 49% at 192 hours, 62% at 240 hours, 69% at 288 hours, and 76% at 336 hours. The amount of copper leached from copper hydroxide particulates was 0.4% at 6 hours, 0.6% at 24 hours, 0.62% at 48 hours, 1.0% at 96 hours, 1.6% at 144 hours, 2.1% at 192 hours, 3.2% at 240 hours, 3.4% at 288 hours, and 3.7% at 336 hours.

Figure 2:
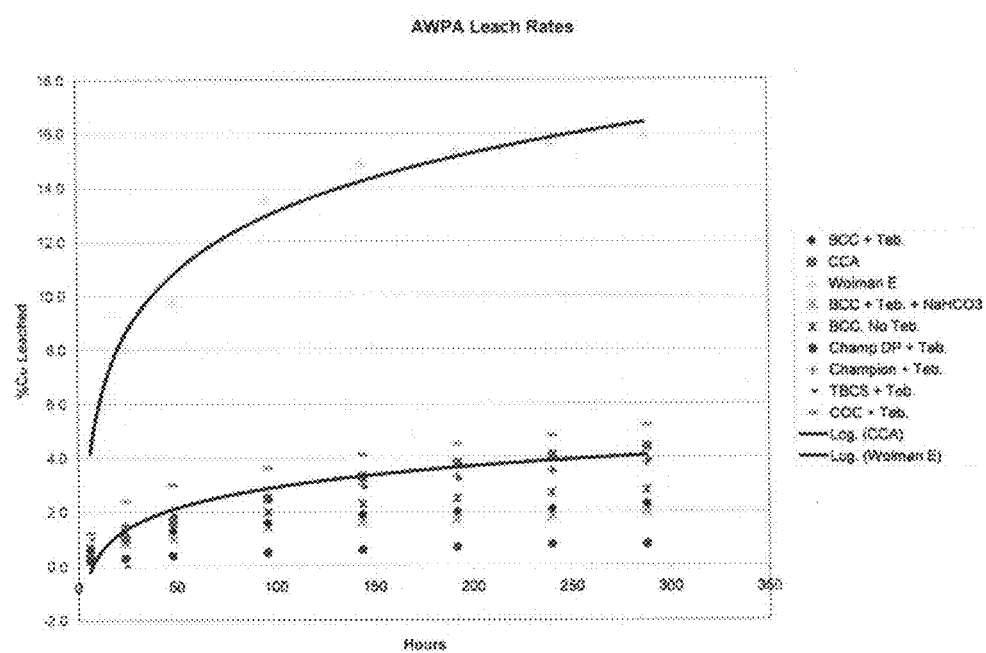
FIG. 2 is a graph demonstrating copper leaching data for selected compositions.

Leaching data from wood was measured using the AWPA Standard Method E11-97 for the following preservative treatments, where unless specified the tebuconazole (TEB) concentration was added as an emulsion at 3% of the weight of the added copper: A) TEB and injected basic copper carbonate particulates; B) traditionally CCA-treated wood (as a control); C) TEB and copper methanolamine carbonate (as a control, believed to approximate the currently available Wolman E treatment); D) TEB and injected basic copper carbonate particulates with sodium bicarbonate buffer; E) injected basic copper carbonate particulates; F) TEB and injected copper hydroxide particulates modified with zinc and magnesium; G) about 5% TEB and injected copper hydroxide particulates modified with phosphate coating; and H) TEB and injected tribasic copper sulfate particulates; I) TEB and injected copper oxychloride particulates. The leaching data for the various particulate slurries and from two controls are shown in FIG. 2.

Using the copper leach rate of CCA as a standard, and viewing the total leached copper at 96 and 240 hours as representative, the leach rate ratios given by the "total leached copper to total CCA-leached copper" is given in Table 3 below:

| Ex. | Description of Preservative System | 96 hr. ration to CCA | 240 hr. ration to CCA |
|---|---|---|---|
| A | 3% TEB and basic copper carbonate particulates | 0.67:1 | 0.51:1 |
| C | 3% TEB and copper MEA carbonate (comparative) | 5.2:1 | 3.85:1 |
| D | 3% TEB and basic copper carbonate particulates with sodium bicarbonate buffer | 0.54:1 | 0.46:1 |
| E | basic copper carbonate particulates | 0.77:1 | 0.63:1 |
| F | 3% TEB and copper hydroxide with Zn and Mg particulates | 0.2:1 | 0.19:1 |
| G | 5% TEB and copper hydroxide particulates modified with phosphate coating | 1.0:1 | 0.88:1 |
| H | 3% TEB and tribasic copper sulfate particulates | 0.96:1 | 0.88:1 |
| I | 3% TEB and copper oxychloride particulates | 1.4:1 | 1.17:1 |

Of the sparingly soluble salts used, the leach rate in descending order is copper MEA carbonate (comparative)>> copper oxychloride>tribasic copper sulfate and/or copper hydroxide with phosphate>basic copper carbonate>copper hydroxide with Zn and Mg. The isoelectric point of copper oxychloride is about 5 to 5.5, and the isoelectric point of tribasic copper sulfate is about 6 to 6.5. As these materials are very poor bases, the higher leach rates from the materials is consistent with expected higher solubility at lower pH values.

The presence of TEB reduced leach rates from basic copper carbonate by about 20%, most likely due to TEB partially coating particulates.

A buffering system, sodium bicarbonate, reduced the leach rates from TEB/basic copper carbonate by about 10% relative to a preservative without the buffer.

Surprisingly, the phosphate material in the copper hydroxide did not appear to show any protective value at all. The reason for this is not clear. Copper hydroxide with magnesium and zinc ions showed the lowest leach rates.

Method of Preserving Wood

Another aspect of the invention relates to wood or a wood product comprising copper based particles and, optionally, one or more additional materials having a preservative function, injected into the wood or wood product. An exemplary piece of wood comprising copper-based particles has a volume of at least about 6 cm$^3$, for example, at least about 100 cm$^3$, such as at least about 1,000 cm$^3$.

The material of this invention is useful for wood, and also for wood composites. Preferred wood composites have the preservative of this invention either mixed with the wood particles before bonding, or preferably injected into the wood particulates and dried prior to bonding. Exemplary wood products include oriented strand board (OSB), particle board (PB), medium density fiberboard (MDF), plywood, laminated veneer lumber (LVL), laminated strand lumber (LSL), hardboard, and the like.

In one embodiment, the wood or wood product has a surface, a thickness, a width, and a length. Preferably, the wood or wood product comprises a homogenous distribution of copper based particles of the invention. In one embodiment, the volume number density of the copper based particles 5 cm from the surface, and preferably throughout the interior of the wood or wood product, is at least about 50%, for example, at least about 60%, at least about 70%, or at least about 75% of the volume number density of the copper-based particles about 1 cm from the surface.

Wood or wood products comprising copper-based particles in accordance with the present invention may be prepared by subjecting the wood to vacuum and/or pressure in the presence of a flowable material comprising the copper-based particles. A pre-injection of carbon dioxide followed by vacuum and then injection of the slurry is a preferred method of injecting the slurry into wood. Injection of particles into the wood or wood product from a flowable material comprising the particles may require longer pressure treatments than would be required for liquids free of such particles. Pressures of, for example, at least about 75 psi, 100 psi, or 150 psi may be used. Exemplary flowable materials include liquids comprising copper-based particles, emulsions comprising copper-based particles, and slurries comprising copper-based particles.

The invention claimed is:

1. A method of preserving wood comprising:
   injecting the wood with a wood preservative composition which comprises a plurality of milled particles comprising a sparingly soluble copper salt,
   wherein less than 0.5% by weight of the particles have an average diameter greater than 1 micron, and at least 80% by weight of the particles have an average diameter greater than 0.03 microns.

2. The method of claim 1, wherein greater than 98% by weight of the particles have a diameter of less than 0.5 microns.

3. The method of claim 1, wherein at least 50% by weight of the particles have a diameter greater than 80 nanometers.

4. The method of claim 1, wherein at least 80% of the particles have a diameter between 0.05 microns and 0.4 microns.

5. The method of claim 1, wherein the sparingly soluble copper salt is substantially crystalline.

6. The method of claim 5, wherein the sparingly soluble copper salt is selected from the group consisting of copper borate, basic copper borate, copper carbonate, basic copper carbonate, tribasic copper sulfate, copper oxychloride, alkaline copper nitrate, copper ferricyanate, copper fluorosilicate, copper thiocyanate, copper diphosphate, copper boride, copper phosphate, copper hydroxide and mixtures thereof.

7. The method of claim 1, wherein the particles comprise a sparingly soluble zinc salt.

8. The method of claim 7, wherein the copper salt comprises zinc cations which are dispersed within the copper salt.

9. The method of claim 7, wherein the sparingly soluble zinc salt is selected from the group consisting of zinc hydroxide, zinc carbonate, zinc chloride, zinc cyanide, zinc fluoride, zinc phosphate, zinc diphosphate, zinc oxide, zinc sulfate and mixtures thereof.

10. The method of claim 1, wherein the sparingly soluble copper salt comprises between 6 and 20 parts of magnesium per 100 parts of copper.

11. The method of claim 10, wherein the magnesium is magnesium hydroxide or magnesium carbonate.

12. The method of claim 1, wherein the composition comprises at least one organic biocide.

13. The method of claim 12, wherein at least a portion of the organic biocide is coated on the milled particles.

14. The method of claim 1, wherein the composition comprises less than 35% by weight of one or more polymers.

15. A method of preserving wood comprising:
   injecting the wood with a wood preservative composition suspended in an aqueous carrier, wherein the composition comprises: a plurality of milled particles comprising a sparingly soluble copper salt; and one or both of an alkanolamine and ammonia,
   wherein the alkanolamine or ammonia, or both, are each in an amount less than 1% by weight of the composition and the aqueous carrier.

16. The method of claim 15, wherein the sparingly soluble copper salt is substantially crystalline.

17. The method of claim 16, wherein the sparingly soluble copper salt is selected from the group consisting of copper borate, basic copper borate, copper carbonate, basic copper carbonate, tribasic copper sulfate, copper oxychloride, alkaline copper nitrate, copper ferricyanate, copper fluorosilicate, copper thiocyanate, copper diphosphate, copper boride, copper phosphate, copper hydroxide and mixtures thereof.

18. The method of claim 15, wherein the alkanolamine or ammonia, or both, are each in an amount less than 0.1% by weight of the composition and the aqueous carrier.

19. The method of claim 15, wherein the alkanolamine or ammonia, or both, are each in an amount less than 1% by weight of the copper.

20. The method of claim 15, wherein the composition comprises at least one organic biocide.

21. The method of claim 20, wherein said organic biocide is an amine present in an amount which is not part of the amount of alkanolamine present in the amount of less than 1% by weight of the composition and the aqueous carrier.

22. The method of claim 20, wherein at least a portion of the organic biocide is coated on the milled particles.

23. A method of preserving wood comprising:
   injecting the wood with a wood preservative composition suspended in an aqueous carrier, wherein the composition comprises: a plurality of milled particles comprising a sparingly soluble copper salt; and one or more dispersing agents, wherein the ratio of the copper to the one or more dispersing agents is about 1:1 or is greater than about 1:1.

24. The method of claim 23, wherein the sparingly soluble copper salt is substantially crystalline.

25. The method of claim 24, wherein the sparingly soluble copper salt is selected from the group consisting of copper borate, basic copper borate, copper carbonate, basic copper carbonate, tribasic copper sulfate, copper oxychloride, alkaline copper nitrate, copper ferricyanide, copper ferricyanate, copper fluorosilicate, copper thiocyanate, copper diphosphate, copper boride, copper phosphate, copper hydroxide and mixtures thereof.

26. The method of claim 23, wherein the ratio of the copper to the one or more dispersing agents is about 5:1.

27. The method of claim 23, wherein the ratio of the copper to the one or more dispersing agents is about 15:1.

28. The method of claim 23, wherein the ratio of the copper to the one or more dispersing agents is about 20:1.

29. The method of claim 23, wherein the ratio of the copper to the one or more dispersing agents is about 30:1.

30. The method of claim 23, wherein the one or more dispersing agents are selected from the group consisting of a surfactant, a polyacrylate, a polysaccharide, a polyaspartic acid, a polysiloxane, a zwitterionic compound and combinations thereof.

31. The method of claim 23, wherein the one or more dispersing agents are selected from the group consisting of surfactants, emulsifiers, polymers and combinations thereof.

32. The method of claim 31, wherein the one or more dispersing agents are in an amount of 0.1 to 20% by weight of the particles.

33. The method of claim 31, wherein the surfactants are selected from the group consisting of cationic surfactants, anionic surfactants and non-ionic surfactants.

34. The method of claim 31, wherein the emulsifiers are selected from the group consisting of gelatine, casein, gum arabic, lysalbinic acid, starch and combinations thereof.

35. The method of claim 31, wherein the polymers are selected from the group consisting of polyvinyl alcohols, polyvinyl pyrrolidones, polyalkylene glycols, polyacrylates and combinations thereof.

* * * * *